(12) United States Patent
Brumbley et al.

(10) Patent No.: US 7,754,943 B2
(45) Date of Patent: Jul. 13, 2010

(54) TRANSGENIC PLANTS USED AS A BIOREACTOR SYSTEM

(75) Inventors: Stevens Michael Brumbley, Redbank Plains (AU); Matthew Peter Purnell, Tarragindi (AU); Barrie Fong Chong, Wynnum West (AU); Lars Arved Petrasovits, West End (AU); Lars Keld Nielsen, Brisbane (AU); Richard Bruce McQualter, Kallangur (AU)

(73) Assignee: BSES Limited, Indooroopilly (AU)

( * ) Notice: Subject to any disclaimer, the term of this patent is extended or adjusted under 35 U.S.C. 154(b) by 652 days.

(21) Appl. No.: 10/520,882

(22) PCT Filed: Jul. 11, 2003

(86) PCT No.: PCT/AU03/00903

§ 371 (c)(1),
(2), (4) Date: Nov. 16, 2005

(87) PCT Pub. No.: WO2004/006657

PCT Pub. Date: Jan. 22, 2004

(65) Prior Publication Data

US 2006/0259998 A1    Nov. 16, 2006

Related U.S. Application Data

(60) Provisional application No. 60/394,869, filed on Jul. 11, 2002.

(51) Int. Cl.
C12N 15/31 (2006.01)
C12N 15/52 (2006.01)
C12N 15/82 (2006.01)
A01H 5/00 (2006.01)
A01H 5/10 (2006.01)

(52) U.S. Cl. ............ 800/288; 800/298; 435/419; 435/468

(58) Field of Classification Search ............ None
See application file for complete search history.

(56) References Cited

U.S. PATENT DOCUMENTS 6,091,002 A * 7/2000 Asrar et al. ........... 800/288
6,475,734 B1 * 11/2002 Liebergesell et al. ........ 435/6

FOREIGN PATENT DOCUMENTS

WO   00/52183 A1   9/2000
WO   01/23596 A2   4/2001

OTHER PUBLICATIONS

Van der Liej, F. et al. (Canadian Journal of Microbiology, 1995; vol. 41, Supplement 1: 222-238).*
Bohmert et al., "Transgenic *Arabidopsis* plants can accumulate polyhydroxybutryate to up to 4% of their fresh weight," *Planta* 211: 841-845, 2000.

Brumbley et al., "Application for Biotechnology for Future Sugar Industry Diversification," *Proceedings of the Conference of the Australian Society of Sugar Cane Technologies*, Apr. 29 to May 1, 2002, 24: 40-46, pp. 41 to 43.
Hahn et al., "Peroxisomes as Sites for Synthesis of Polyhydroxyalkanoates in Transgenic Plants," *Biotechnology Progress* 15: 1053-1057, 1999.
International Search Report for PCT/AU03/00903, mailed Oct. 31, 2003, 5 pages.
Karr et al., "Analysis of Poly-β-Hydroxybutyrate in *Rhizobium japonicum* Bacteroids by Ion-Exclusion High-Pressure Liquid Chromatography and UV Detection," *Applied and Environmental Microbiology* 46(6): 1339-1344, Dec. 1983.
Katz et al., "Cloning and Expression of the Tyrosinase Gene from *Streptomyces antibioticus* in *Streptomyces lividans*," *Journal of General Microbiology* 129: 2703-2714, 1983.
Kim et al., "Isolation of stress-related genes of rubber particles and latex in fig tree (*Ficus carica*) and their expressions by abiotic stress or plant hormone treatments," *Plant Cell Physiol.* 44(4): 412-414, Apr. 2003.
Knight et al., "The *sfr6* Mutation in *Arabidopsis* Suppresses Low-Temperature Induction of Genes Dependent on the CRT/DRE Sequence Motif," *The Plant Cell* 11: 875-886, May 1999.

(Continued)

*Primary Examiner*—Russell Kallis
(74) *Attorney, Agent, or Firm*—Seed IP Law Group PLLC

(57) ABSTRACT

The present invention relates generally to the use of plants as bioreactors for the production of molecules having useful properties such as inter alia polymers, metabolites, proteins, pharmaceuticals and nutraceuticals. More particularly, the present invention contemplates the use of grasses, and even more particularly C4 grasses, such as sugar-cane, for the production of a range of compounds such as, for example, polyhydroxyalkanoates, pHBA, vanillin, indigo, adipic acid, 2-phenylethanol, 1,3-propane-diol, sorbitol, fructan polymers and lactic acid as well as other products including, inter alia, other plastics, silks, carbohydrates, therapeutic and nutraceutic proteins and antibodies. The present invention further extends to transgenic plants and, in particular, transgenic C4 grass plants, capable of producing the compounds noted above and other products, and to methods for generating such plants. The ability to utilize the high growth rate and efficient carbon fixation of C4 grasses is advantageous, in that it obviates the significant growth penalties observed in other plants, and results in high yields of desired product without necessarily causing concomitant deleterious effects on individual plants. In addition, the C4 grass, sugarcane, is particularly advantageous, as in addition to the features common to all C4 grasses, this plant accumulates sucrose. This sucrose store provides a ready supply of carbon based compounds and energy which may further obviate any deleterious effects on the growth of the plant associated with the production of the product. The present invention provides, therefore, a bioreactor system comprising a genetically modified plant designed to produce particular metabolic or biosynthetic products of interest.

18 Claims, 16 Drawing Sheets

OTHER PUBLICATIONS

Mayer et al., "Rerouting the Plant Phenylpropanoid Pathway by Expression of a Novel Enoyl-CoA Hydratase/Lyase Enzyme Function," *The Plant Cell* 13: 1669-1682, Jul. 2001.

Mekhedov et al., "An unusual seed-specific 3-ketoacyl-ACP synthase associated with the biosynthesis of petroselinic acid in coriander," *Plant Mol Biol.* 47(4); 507-518, Nov. 2001.

Niu et al., "Benzene-free synthesis of adipic adic," *Biotechnol Prog.* 18(2): 201-211, Mar.-Apr. 2002.

Ostle et al., "Nile Blue A as a Fluorescent Stain for Poly-β-Hydroxybutyrate," *Applied and Environmental Microbiology* 44(1): 238-241, Jul. 1982.

Ow et al., "Transient and Stable Expression of the Firefly Luciferase Gene in Plant Cells and Transgenic Plants," *Science* 234(4778): 856-859, Nov. 14, 1986.

Poirier et al., "Polyhydroxybutyrate, a Biodegradable Thermoplastic, Produced in Transgenic Plants," *Science* 256(5056): 520-523, Apr. 24, 1992.

Prasad et al., "Heat and Osmotic Stress Responses of Probiotic *Lactobacillus rhamnosus* HN001 (DR20) in Relation to Viability after Drying," *Applied and Environmental Microbiology* 69(2): 917-925, Feb. 2003.

Prasher et al., "Cloning and expression of the cDNA coding for aequorin, a bioluminescent calcium-binding protein," *Biochem Biophys Res Commun.* 126(3): 1259-1268, Feb. 15, 1985.

Salomon et al., "Genetic identification of functions of TR-DNA transcripts in octopine crown galls," *The EMBO Journal* 3(1): 141-146, 1984.

Siebert et al., "Genetic Engineering of Plant Secondary Metabolism," *Plant Physiol.* 112: 811-819, 1996.

Snell et al., "Polyhydroxyalkanoate Polymers and Their Production in Transgenic Plants," *Metabolic Engineering* 4(1): 29-40, Jan. 2002.

Steinbüchel et al., "Physiology and molecular genetics of poly(beta-hydroxy-alkanoic acid) synthesis in *Alcaligenes eutrophus*," *Mol Microbiol.* 5(3): 535-542, Mar. 1991.

Sticher et al., "Systemic acquired resistance," *Annu Rev Phytopathol.* 35: 235-270, 1997.

Sutcliffe, "Nucleotide sequence of the ampicillin resistance gene of *Escherichia coli* plasmid pBR322," *Proc. Natl. Acad. Sci. USA* 75(8): 3737-3741, Aug. 1978.

Taguchi et al., "Analysis of mutational effects of a polyhydroxybutyrate (PHB) polymerase on bacterial PHB accumulation using an in vivo assay system," *FEMS Microbiol Lett.* 198(1): 65-71, Apr. 20, 2001.

Thillet et al., "Site-directed Mutagenesis of Mouse Dihydrofolate Reductase," *The Journal of Biological Chemistry* 263(25): 12500-12508, Sep. 5, 1988.

Verpoorte et al., "Engineering secondary metabolite production in plants," *Curr Opin Biotechnol.* 13(2): 181-187, Apr. 2002.

Zukowski et al., "Chromogenic identification of genetic regulatory signals in *Bacillus subtilis* based on expression of a cloned *Pseudomonas* gene," *Proc. Natl. Acad. Sci. USA* 80: 1101-1105, Feb. 1983.

* cited by examiner

SEQUENCE LISTING

```
<160> NUMBER OF SEQ ID NOS: 56

<210> SEQ ID NO 1
<211> LENGTH: 1182
<212> TYPE: DNA
<213> ORGANISM: Rastonia Eutropia
<220> FEATURE:
<221> NAME/KEY: CDS
<222> LOCATION: (1)..(1182)

<400> SEQUENCE: 1 atg act gac gtt gtc atc gta tcc gcc gcc cgc acc gcg gtc ggc aag      48
Met Thr Asp Val Val Ile Val Ser Ala Ala Arg Thr Ala Val Gly Lys
1               5                   10                  15 ttt ggc ggc tcg ctg gcc aag atc ccg gca ccg gaa ctg ggt gcc gtg      96
Phe Gly Gly Ser Leu Ala Lys Ile Pro Ala Pro Glu Leu Gly Ala Val
                20                  25                  30 gtc atc aag gcc gcg ctg gag cgc gcc ggc gtc aag ccg gag cag gtg     144
```

```
                Val Ile Lys Ala Ala Leu Glu Arg Ala Gly Val Lys Pro Glu Gln Val
                             35                  40                  45 agc gaa gtc atc atg ggc cag gtg ctg acc gcc ggt tcg ggc cag aac         192
Ser Glu Val Ile Met Gly Gln Val Leu Thr Ala Gly Ser Gly Gln Asn
 50                  55                  60 ccc gca cgc cag gcc gcg atc aag gcc ggc ctg ccg gcg atg gtg ccg         240
Pro Ala Arg Gln Ala Ala Ile Lys Ala Gly Leu Pro Ala Met Val Pro
 65                  70                  75                  80 gcc atg acc atc aac aag gtg tgc ggc tcg ggc ctg aag gcc gtg atg         288
Ala Met Thr Ile Asn Lys Val Cys Gly Ser Gly Leu Lys Ala Val Met
                     85                  90                  95 ctg gcc gcc aac gcg atc atg gcg ggc gac gcc gag atc gtg gtg gcc         336
Leu Ala Ala Asn Ala Ile Met Ala Gly Asp Ala Glu Ile Val Val Ala
                    100                 105                 110 ggc ggc cag gaa aac atg agc gcc gcc ccg cac gtg ctg ccg ggc tcg         384
Gly Gly Gln Glu Asn Met Ser Ala Ala Pro His Val Leu Pro Gly Ser
                    115                 120                 125 cgc gat ggt ttc cgc atg ggc gat gcc aag ctg gtc gac acc atg atc         432
Arg Asp Gly Phe Arg Met Gly Asp Ala Lys Leu Val Asp Thr Met Ile
130                 135                 140 gtc gac ggc ctg tgg gac gtg tac aac cag tac cac atg ggc atc acc         480
Val Asp Gly Leu Trp Asp Val Tyr Asn Gln Tyr His Met Gly Ile Thr
145                 150                 155                 160 gcc gag aac gtg gcc aag gaa tac ggc atc aca cgc gag gcg cag gat         528
Ala Glu Asn Val Ala Lys Glu Tyr Gly Ile Thr Arg Glu Ala Gln Asp
                    165                 170                 175 gag ttc gcc gtc ggc tcg cag aac aag gcc gaa gcc gcg cag aag gcc         576
Glu Phe Ala Val Gly Ser Gln Asn Lys Ala Glu Ala Ala Gln Lys Ala
                    180                 185                 190 ggc aag ttt gac gaa gag atc gtc ccg gtg ctg atc ccg cag cgc aag         624
Gly Lys Phe Asp Glu Glu Ile Val Pro Val Leu Ile Pro Gln Arg Lys
                    195                 200                 205 ggc gac ccg gtg gcc ttc aag acc gac gag ttc gtg cgc cag ggc gcc         672
Gly Asp Pro Val Ala Phe Lys Thr Asp Glu Phe Val Arg Gln Gly Ala
210                 215                 220 acg ctg gac agc atg tcc ggc ctc aag ccc gcc ttc gac aag gcc ggc         720
Thr Leu Asp Ser Met Ser Gly Leu Lys Pro Ala Phe Asp Lys Ala Gly
225                 230                 235                 240 acg gtg acc gcg gcc aac gcc tcg ggc ctg aac gac ggc gcc gcc gcg         768
Thr Val Thr Ala Ala Asn Ala Ser Gly Leu Asn Asp Gly Ala Ala Ala
                    245                 250                 255 gtg gtg gtg atg tcg gcg gcc aag gcc aag gaa ctg ggc ctg acc ccg         816
Val Val Val Met Ser Ala Ala Lys Ala Lys Glu Leu Gly Leu Thr Pro
                    260                 265                 270 ctg gcc acg atc aag agc tat gcc aac gcc ggt gtc gat ccc aag gtg         864
Leu Ala Thr Ile Lys Ser Tyr Ala Asn Ala Gly Val Asp Pro Lys Val
                    275                 280                 285 atg ggc atg ggc ccg gtg ccg gcc tcc aag cgc gcc ctg tcg cgc gcc         912
Met Gly Met Gly Pro Val Pro Ala Ser Lys Arg Ala Leu Ser Arg Ala
                    290                 295                 300 gag tgg acc ccg caa gac ctg gac ctg atg gag atc aac gag gcc ttt         960
Glu Trp Thr Pro Gln Asp Leu Asp Leu Met Glu Ile Asn Glu Ala Phe
305                 310                 315                 320 gcc gcc cag gcg ctg gcg gtg cac cag cag atg ggc tgg gac acc tcc        1008
Ala Ala Gln Ala Leu Ala Val His Gln Gln Met Gly Trp Asp Thr Ser
                    325                 330                 335 aag gtc aat gtg aac ggc ggc gcc atc gcc atc ggc cac ccg atc ggc        1056
Lys Val Asn Val Asn Gly Gly Ala Ile Ala Ile Gly His Pro Ile Gly
                    340                 345                 350
```

```
gcg tcg ggc tgc cgt atc ctg gtg acg ctg ctg cac gag atg aag cgc    1104
Ala Ser Gly Cys Arg Ile Leu Val Thr Leu Leu His Glu Met Lys Arg
        355                 360                 365 cgt gac gcg aag aag ggc ctg gcc tcg ctg tgc atc ggc ggc ggc atg    1152
Arg Asp Ala Lys Lys Gly Leu Ala Ser Leu Cys Ile Gly Gly Gly Met
    370                 375                 380 ggc gtg gcg ctg gca gtc gag cgc aaa taa                            1182
Gly Val Ala Leu Ala Val Glu Arg Lys
385                 390
```

<210> SEQ ID NO 2
<211> LENGTH: 393
<212> TYPE: PRT
<213> ORGANISM: Rastonia Eutropia

<400> SEQUENCE: 2

```
Met Thr Asp Val Val Ile Val Ser Ala Ala Arg Thr Ala Val Gly Lys
1               5                   10                  15

Phe Gly Gly Ser Leu Ala Lys Ile Pro Ala Pro Glu Leu Gly Ala Val

Ala Ala Gln Ala Leu Ala Val His Gln Gln Met Gly Trp Asp Thr Ser
                325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
        355                 360                 365

Arg Asp Ala Lys Lys Gly Leu Ala Ser Leu Cys Ile Gly Gly Met
    370                 375                 380

Gly Val Ala Leu Ala Val Glu Arg Lys
385                 390

<210> SEQ ID NO 3
<211> LENGTH: 1280
<212> TYPE: DNA
<213> ORGANISM: Rastonia Eutropia

<400> SEQUENCE: 3
ggatccatga ctgacgttgt catcgtatcc gccgcccgca ccgcggtcgg caagtttggc      60
ggctcgctgg ccaagatccc ggcaccggaa ctgggtgccg tggtcatcaa ggccgcgctg     120
gagcgcgccg gcgtcaagcc ggagcaggtg agcgaagtca tcatgggcca ggtgctgacc     180
gccggttcgg gccagaaccc cgcacgccag gccgcgatca aggccggcct gccggcgatg     240
gtgccggcca tgaccatcaa caaggtgtgc ggctcgggcc tgaaggccgt gatgctggcc     300
gccaacgcga tcatggcggg cgacgccgag atcgtggtgg ccggcggcca ggaaaacatg     360
agcgccgccc cgcacgtgct gccgggctcg cgcgatggtt ccgcatgggc gatgccaag     420
ctggtcgaca ccatgatcgt cgacggcctg tgggacgtgt acaaccagta ccacatgggc     480
atcaccgccg agaacgtggc caaggaatac ggcatcacac gcgaggcgca ggatgagttc     540
gccgtcggct cgcagaacaa ggccgaagcc gcgcagaagg ccgcaagtt tgacgaagag     600
atcgtcccgg tgctgatccc gcagcgcaag gcgacccgg tggccttcaa gaccgacgag     660
ttcgtgcgcc agggcgccac gctggacagc atgtccggcc tcaagcccgc cttcgacaag     720
gccggcacgg tgaccgcggc caacgcctcg ggcctgaacg acgcgccgc cgcggtggtg     780
gtgatgtcgg cggccaaggc caaggaactg gccctgaccc cgctggccac gatcaagagc     840
tatgccaacg ccggtgtcga tcccaaggtg atgggcatgg gccggtgcc ggcctccaag     900
cgcgccctgt cgcgcgccga gtggaccccg caagacctgg acctgatgga gatcaacgag     960
gcctttgccg cccaggcgct ggcggtgcac cagcagatgg gctggacac ctccaaggtc    1020
aatgtgaacg gcggcgccat cgccatcggc cacccgatcg gcgcgtcggg ctgccgtatc    1080
ctggtgacgc tgctgcacga gatgaagcgc cgtgacgcga agaagggcct ggcctcgctg    1140
tgcatcggcg gcggcatggg cgtggcgctg gcagtcgagc gcaaataagg aaggggtttt    1200
ccggggccgc gcgcggttgg cgcggacccg gcgacgataa cgaagccaat caaggagtgg    1260
acatgactca gggggtacc                                                  1280

<210> SEQ ID NO 4
<211> LENGTH: 738
<212> TYPE: DNA
<213> ORGANISM: Rastonia Eutropia
<220> FEATURE:
<221> NAME/KEY: CDS
<222> LOCATION: (1)..(738)

<400> SEQUENCE: 4

```
atg act cag cgc att gcg tat gtg acc ggc ggc atg ggt ggt atc gga        48
Met Thr Gln Arg Ile Ala Tyr Val Thr Gly Gly Met Gly Gly Ile Gly
1               5                   10                  15 acc gcc att tgc cag cgg ctg gcc aag gat ggc ttt cgt gtg gtg gcc        96
Thr Ala Ile Cys Gln Arg Leu Ala Lys Asp Gly Phe Arg Val Val Ala
            20                  25                  30 ggt tgc ggc ccc aac tcg ccg cgc cgc gaa aag tgg ctg gag cag cag       144
Gly Cys Gly Pro Asn Ser Pro Arg Arg Glu Lys Trp Leu Glu Gln Gln
        35                  40                  45 aag gcc ctg ggc ttc gat ttc att gcc tcg gaa ggc aat gtg gct gac       192
Lys Ala Leu Gly Phe Asp Phe Ile Ala Ser Glu Gly Asn Val Ala Asp
    50                  55                  60 tgg gac tcg acc aag acc gca ttc gac aag gtc aag tcc gag gtc ggc       240
Trp Asp Ser Thr Lys Thr Ala Phe Asp Lys Val Lys Ser Glu Val Gly
65                  70                  75                  80 gag gtt gat gtg ctg atc aac aac gcc ggt atc acc cgc gac gtg gtg       288
Glu Val Asp Val Leu Ile Asn Asn Ala Gly Ile Thr Arg Asp Val Val
                85                  90                  95 ttc cgc aag atg acc cgc gcc gac tgg gat gcg gtg atc gac acc aac       336
Phe Arg Lys Met Thr Arg Ala Asp Trp Asp Ala Val Ile Asp Thr Asn
            100                 105                 110 ctg acc tcg ctg ttc aac gtc acc aag cag gtg atc gac ggc atg gcc       384
Leu Thr Ser Leu Phe Asn Val Thr Lys Gln Val Ile Asp Gly Met Ala
        115                 120                 125 gac cgt ggc tgg ggc cgc atc gtc aac atc tcg tcg gtg aac ggg cag       432
Asp Arg Gly Trp Gly Arg Ile Val Asn Ile Ser Ser Val Asn Gly Gln
    130                 135                 140 aag ggc cag ttc ggc cag acc aac tac tcc acc gcc aag gcc ggc ctg       480
Lys Gly Gln Phe Gly Gln Thr Asn Tyr Ser Thr Ala Lys Ala Gly Leu
145                 150                 155                 160 cat ggc ttc acc atg gca ctg gcg cag gaa gtg gcg acc aag ggc gtg       528
His Gly Phe Thr Met Ala Leu Ala Gln Glu Val Ala Thr Lys Gly Val
                165                 170                 175 acc gtc aac acg gtc tct ccg ggc tat atc gcc acc gac atg gtc aag       576
Thr Val Asn Thr Val Ser Pro Gly Tyr Ile Ala Thr Asp Met Val Lys
            180                 185                 190 gcg atc cgc cag gac gtg ctc gac aag atc gtc gcg acg atc ccg gtc       624
Ala Ile Arg Gln Asp Val Leu Asp Lys Ile Val Ala Thr Ile Pro Val
        195                 200                 205 aag cgc ctg ggc ctg cca gaa gag atc gcc tcg atc tgc gcc tgg ttg       672
Lys Arg Leu Gly Leu Pro Glu Glu Ile Ala Ser Ile Cys Ala Trp Leu
    210                 215                 220 tcg tcg gag gag tcc ggt ttc tcg acc ggc gcc gac ttc tcg ctc aac       720
Ser Ser Glu Glu Ser Gly Phe Ser Thr Gly Ala Asp Phe Ser Leu Asn
225                 230                 235                 240 ggc ggc ctg cat atg ggc                                                738
Gly Gly Leu His Met Gly
                245
```

<210> SEQ ID NO 5
<211> LENGTH: 246
<212> TYPE: PRT
<213> ORGANISM: Rastonia Eutropia

<400> S

-continued

```
        35                  40                  45

Lys Ala Leu Gly Phe Asp Phe Ile Ala Ser Glu Gly Asn Val Ala Asp
    50                  55                  60

Trp Asp Ser Thr Lys Thr Ala Phe Asp Lys Val Lys Ser Glu Val Gly
65                  70                  75                  80

Glu Val Asp Val Leu Ile Asn Asn Ala Gly Ile Thr Arg Asp Val Val
                85                  90                  95

Phe Arg Lys Met Thr Arg Ala Asp Trp Asp Ala Val Ile Asp Thr Asn
            100                 105                 110

Leu Thr Ser Leu Phe Asn Val Thr Lys Gln Val Ile Asp Gly Met Ala
        115                 120                 125

Asp Arg Gly Trp Gly Arg Ile Val Asn Ile Ser Ser Val Asn Gly Gln
    130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
                165                 170                 175

Thr Val Asn Thr Val Ser Pro Gly Tyr Ile Ala Thr Asp Met Val Lys
            180                 185                 190

Ala Ile Arg Gln Asp Val Leu Asp Lys Ile Val Ala Thr Ile Pro Val
        195                 200                 205

Lys Arg Leu Gly Leu Pro Glu Glu Ile Ala Ser Ile Cys Ala Trp Leu
    210                 215                 220

Ser Ser Glu Glu Ser Gly Phe Ser Thr Gly Ala Asp Phe Ser Leu Asn
225                 230                 235                 240

Gly Gly Leu His Met Gly
                245

<210> SEQ ID NO 6
<211> LENGTH: 783
<212> TYPE: DNA
<213> ORGANISM: Rastonia Eutropia

<400> SEQUENCE: 6
ggatccatga ctcagcgcat tgcgtatgtg accggcggca tgggtggtat cggaaccgcc      60
atttgccagc ggctggccaa ggatggcttt cgtgtggtgg ccggttgcgg ccccaactcg     120
ccgcgccgcg aaaagtggct ggagcagcag aaggccctgg gcttcgattt cattgcctcg     180
gaaggcaatg tggctgactg ggactcgacc aagaccgcat tcgacaaggt caagtccgag     240
gtcggcgagg ttgatgtgct gatcaacaac gccggtatca cccgcgacgt ggtgttccgc     300
aagatgaccc gcgccgactg ggatgcggtg atcgacacca acctgacctc gctgttcaac     360
gtcaccaagc aggtgatcga cggcatggcc gaccgtggct ggggccgcat cgtcaacatc     420
tcgtcggtga acgggcagaa gggccagttc ggccagacca actactccac cgccaaggcc     480
ggcctgcatg gcttcaccat ggcactggcg caggaagtgg cgaccaaggg cgtgaccgtc     540
aacacggtct ctccgggcta tatcgccacc gacatggtca aggcgatccg ccaggacgtg     600
ctcgacaaga tcgtcgcgac gatcccggtc aagcgcctgg gcctgccaga agagatcgcc     660
tcgatctgcg cctggttgtc gtcggaggag tccggtttct cgaccggcgc cgacttctcg     720
ctcaacggcg gcctgcatat gggctgacct gccggcctgg ttccaccagt cggcaggggt     780
acc                                                                   783

<210> SEQ ID NO 7
```

```
<211> LENGTH: 1767
<212> TYPE: DNA
<213> ORGANISM: Rastonia Eutropia
<220> FEATURE:
<221> NAME/KEY: CDS
<222> LOCATION: (1)..(1767)

<400> SEQUENCE: 7 atg gcg acc ggc aaa ggc gcg gca gct tcc acg cag gaa ggc aag tcc         48
Met Ala Thr Gly Lys Gly Ala Ala Ala Ser Thr Gln Glu Gly Lys Ser
1               5                   10                  15 caa cca ttc aag gtc acg ccg ggg cca ttc gat cca gcc aca tgg ctg         96
Gln Pro Phe Lys Val Thr Pro Gly Pro Phe Asp Pro Ala Thr Trp Leu
            20                  25                  30 gaa tgg tcc cgc cag tgg cag ggc act gaa ggc aac ggc cac gcg gcc        144
Glu Trp Ser Arg Gln Trp Gln Gly Thr Glu Gly Asn Gly His Ala Ala
        35                  40                  45 gcg tcc ggc att ccg ggc ctg gat gcg ctg gca ggc gtc aag atc gcg        192
Ala Ser Gly Ile Pro Gly Leu Asp Ala Leu Ala Gly Val Lys Ile Ala
    50                  55                  60 ccg gcg cag ctg ggt gat atc cag cag cgc tac atg aag gac ttc tca        240
Pro Ala Gln Leu Gly Asp Ile Gln Gln Arg Tyr Met Lys Asp Phe Ser
65                  70                  75                  80 gcg ctg tgg cag gcc atg gcc gag ggc aag gcc gag gcc acc ggt ccg        288
Ala Leu Trp Gln Ala Met Ala Glu Gly Lys Ala Glu Ala Thr Gly Pro
                85                  90                  95 ctg cac gac cgg cgc ttc gcc ggc gac gca tgg cgc acc aac ctc cca        336
Leu His Asp Arg Arg Phe Ala Gly Asp Ala Trp Arg Thr Asn Leu Pro
            100                 105                 110 tat cgc ttc gct gcc gcg ttc tac ctg ctc aat gcg cgc gcc ttg acc        384
Tyr Arg Phe Ala Ala Ala Phe Tyr Leu Leu Asn Ala Arg Ala Leu Thr
        115                 120                 125 gag ctg gcc gat gcc gtc gag gcc gat gcc aag acc cgc cag cgc atc        432
Glu Leu Ala Asp Ala Val Glu Ala Asp Ala Lys Thr Arg Gln Arg Ile
    130                 135                 140 cgc ttc gcg atc tcg caa tgg gtc gat gcg atg tcg ccc gcc aac ttc        480
Arg Phe Ala Ile Ser Gln Trp Val Asp Ala Met Ser Pro Ala Asn Phe
145                 150                 155                 160 ctt gcc acc aat ccc gag gcg cag cgc ctg ctg atc gag tcg ggc ggc        528
Leu Ala Thr Asn Pro Glu Ala Gln Arg Leu Leu Ile Glu Ser Gly Gly
                165                 170                 175 gaa tcg ctg cgt gcc ggc gtg cgc aac atg atg gaa gac ctg aca cgc        576
Glu Ser Leu Arg Ala Gly Val Arg Asn Met Met Glu Asp Leu Thr Arg
            180                 185                 190 ggc aag atc tcg cag acc gac gag agc gcg ttt gag gtc ggc cgc aat        624
Gly Lys Ile Ser Gln Thr Asp Glu Ser Ala Phe Glu Val Gly Arg Asn
        195                 200                 205 gtc gcg gtg acc gaa ggc gcc gtg gtc ttc gag aac gag tac ttc cag        672
Val Ala Val Thr Glu Gly Ala Val Val Phe Glu Asn Glu Tyr Phe Gln
    210                 215                 220 ctg ttg cag tac aag ccg ctg acc gac aag gtg cac gcg cgc ccg ctg        720
Leu Leu Gln Tyr Lys Pro Leu Thr Asp Lys Val His Ala Arg Pro Leu
225                 230                 235                 240 ctg atg gtg ccg ccg tgc atc aac aag tac tac atc ctg gac ctg cag        768
Leu Met Val Pro Pro Cys Ile Asn Lys Tyr Tyr Ile Leu Asp Leu Gln
                245                 250                 255 ccg gag agc tcg ctg gtg cgc cat gtg gtg gag cag gga cat acg gtg        816
Pro Glu Ser Ser Leu Val Arg His Val Val Glu Gln Gly His Thr Val
            260                 265                 270 ttt ctg gtg tcg tgg cgc aat ccg gac gcc agc atg gcc ggc agc acc        864
Phe Leu Val Ser Trp Arg Asn Pro Asp Ala Ser Met Ala Gly Ser Thr
```

-continued

```
           275                 280                 285
tgg gac gac tac atc gag cac gcg gcc atc cgc gcc atc gaa gtc gcg        912
Trp Asp Asp Tyr Ile Glu His Ala Ala Ile Arg Ala Ile Glu Val Ala
    290                 295                 300 cgc gac atc agc ggc cag gac aag atc aac gtg ctc ggc ttc tgc gtg        960
Arg Asp Ile Ser Gly Gln Asp Lys Ile Asn Val Leu Gly Phe Cys Val
305                 310                 315                 320 ggc ggc acc att gtc tcg acc gcg ctg gcg gtg ctg gcc gcg cgc ggc       1008
Gly Gly Thr Ile Val Ser Thr Ala Leu Ala Val Leu Ala Ala Arg Gly
                325                 330                 335 gag cac ccg gcc gcc agc gtc acg ctg ctg acc acg ctg ctg gac ttt       1056
Glu His Pro Ala Ala Ser Val Thr Leu Leu Thr Thr Leu Leu Asp Phe
            340                 345                 350 gcc gac acg ggc atc ctc gac gtc ttt gtc gac gag ggc cat gtg cag       1104
Ala Asp Thr Gly Ile Leu Asp Val Phe Val Asp Glu Gly His Val Gln
            355                 360                 365 ttg cgc gag gcc acg ctg ggc ggc ggc gcc ggc gcg ccg tgc gcg ctg       1152
Leu Arg Glu Ala Thr Leu Gly Gly Gly Ala Gly Ala Pro Cys Ala Leu
370                 375                 380 ctg cgc ggc ctt gag ctg gcc aat acc ttc tcg ttc ttg cgc ccg aac       1200
Leu Arg Gly Leu Glu Leu Ala Asn Thr Phe Ser Phe Leu Arg Pro Asn
385                 390                 395                 400 gac ctg gtg tgg aac tac gtg gtc gac aac tac ctg aag ggc aac acg       1248
Asp Leu Val Trp Asn Tyr Val Val Asp Asn Tyr Leu Lys Gly Asn Thr
                405                 410                 415 ccg gtg ccg ttc gac ctg ctg ttc tgg aac ggc gac gcc acc aac ctg       1296
Pro Val Pro Phe Asp Leu Leu Phe Trp Asn Gly Asp Ala Thr Asn Leu
            420                 425                 430 ccg ggg ccg tgg tac tgc tgg tac ctg cgc cac acc tac ctg cag aac       1344
Pro Gly Pro Trp Tyr Cys Trp Tyr Leu Arg His Thr Tyr Leu Gln Asn
            435                 440                 445 gag ctc aag gta ccg ggc aag ctg acc gtg tgc ggc gtg ccg gtg gac       1392
Glu Leu Lys Val Pro Gly Lys Leu Thr Val Cys Gly Val Pro Val Asp
450                 455                 460 ctg gcc agc atc gac gtg ccg acc tat atc tac ggc tcg cgc gaa gac       1440
Leu Ala Ser Ile Asp Val Pro Thr Tyr Ile Tyr Gly Ser Arg Glu Asp
465                 470                 475                 480 cat atc gtg ccg tgg acc gcg gcc tat gcc tcg acc gcg ctg ctg gcg       1488
His Ile Val Pro Trp Thr Ala Ala Tyr Ala Ser Thr Ala Leu Leu Ala
                485                 490                 495 aac aag ctg cgc ttc gtg ctg ggt gcg tcg ggc cat atc gcc ggt gtg       1536
Asn Lys Leu Arg Phe Val Leu Gly Ala Ser Gly His Ile Ala Gly Val
            500                 505                 510 atc aac ccg ccg gcc aag aac aag cgc agc cac tgg act aac gat gcg       1584
Ile Asn Pro Pro Ala Lys Asn Lys Arg Ser His Trp Thr Asn Asp Ala
            515                 520                 525 ctg ccg gag tcg ccg cag caa tgg ctg gcc ggc gcc atc gag cat cac       1632
Leu Pro Glu Ser Pro Gln Gln Trp Leu Ala Gly Ala Ile Glu His His
530                 535                 540 ggc agc tgg tgg ccg gac tgg acc gca tgg ctg gcc ggg cag gcc ggc       1680
Gly Ser Trp Trp Pro Asp Trp Thr Ala Trp Leu Ala Gly Gln Ala Gly
545                 550                 555                 560 gcg aaa cgc gcc gcg ccc gcc aac tat ggc aat gcg cgc tat cgc gca       1728
Ala Lys Arg Ala Ala Pro Ala Asn Tyr Gly Asn Ala Arg Tyr Arg Ala
                565                 570                 575 atc gaa ccc gcg cct ggg cga tac gtc aaa gcc aag gca                   1767
Ile Glu Pro Ala Pro Gly Arg Tyr Val Lys Ala Lys Ala
            580                 585
```

<210> SEQ ID NO 8
<211> LENGTH: 589
<212> TYPE: PRT
<213> ORGANISM: Rastonia Eutropia

<400> SEQUENCE: 8

```
Met Ala Thr Gly Lys Gly Ala Ala Ala Ser Thr Gln Glu Gly Lys Ser
1               5                   10                  15

Gln Pro Phe Lys Val Thr Pro Gly Pro Phe Asp Pro Ala Thr Trp Leu
            20                  25                  30

Glu Trp Ser Arg Gln Trp Gln Gly Thr Glu Gly Asn Gly His Ala Ala
        35                  40                  45

Ala Ser Gly Ile Pro Gly Leu Asp Ala Leu Ala Gly Val Lys Ile Ala
    50                  55                  60

Pro Ala Gln Leu Gly Asp Ile Gln Gln Arg Tyr Met Lys Asp Phe Ser
65                  70                  75                  80

Ala Leu Trp Gln Ala Met Ala Glu Gly Lys Ala Glu Ala Thr Gly Pro
                85                  90                  95

Leu His Asp Arg Arg Phe Ala Gly Asp Ala Trp Arg Thr Asn Leu Pro
            100                 105                 110

Tyr Arg Phe Ala Ala Ala Phe Tyr Leu Leu Asn Ala Arg Ala Leu Thr
        115                 120                 125

Glu Leu Ala Asp Ala Val Glu Ala Asp Ala Lys Thr Arg Gln Arg Ile
    130                 135                 140

Arg Phe Ala Ile Ser Gln Trp Val Asp Ala Met Ser Pro Ala Asn Phe
145                 150                 155                 160

Leu Ala Thr Asn Pro Glu Ala Gln Arg Leu Leu Ile Glu Ser Gly Gly
                165                 170                 175

Glu Ser Leu Arg Ala Gly Val Arg Asn Met Met Glu Asp Leu Thr Arg
            180                 185                 190

Gly Lys Ile Ser Gln Thr Asp Glu Ser Ala Phe Glu Val Gly Arg Asn
        195                 200                 205

Val Ala Val Thr Glu Gly Ala Val Val Phe Glu Asn Glu Tyr Phe Gln
    210                 215                 220

Leu Leu Gln Tyr Lys Pro Leu Thr Asp Lys Val His Ala Arg Pro Leu
225                 230                 235                 240

Leu Met Val Pro Pro Cys Ile Asn Lys Tyr Tyr Ile Leu Asp Leu Gln
                245                 250                 255

Pro Glu Ser Ser Leu Val Arg His Val Val Glu Gln Gly His Thr Val
            260                 265                 270

Phe Leu Val Ser Trp Arg Asn Pro Asp Ala Ser Met Ala Gly Ser Thr
        275                 280                 285

Trp Asp Asp Tyr Ile Glu His Ala Ala Ile Arg Ala Ile Glu Val Ala
    290                 295                 300

Arg Asp Ile Ser Gly Gln Asp Lys Ile Asn Val Leu Gly Phe Cys Val
305                 310                 315                 320

Gly Gly Thr Ile Val Ser Thr Ala Leu Ala Val Leu Ala Ala Arg Gly
                325                 330                 335

Glu His Pro Ala Ala Ser Val Thr Leu Leu Thr Thr Leu Leu Asp Phe
            340                 345                 350

Ala Asp Thr Gly Ile Leu Asp Val Phe Val Asp Glu Gly His Val Gln
        355                 360                 365

Leu Arg Glu Ala Thr Leu Gly Gly Gly Ala Gly Ala Pro Cys Ala Leu
    370                 375                 380
```

-continued

```
Leu Arg Gly Leu Glu Leu Ala Asn Thr Phe Ser Phe Leu Arg Pro Asn
385                 390                 395                 400

Asp Leu Val Trp Asn Tyr Val Val Asp Asn Tyr Leu Lys Gly Asn Thr
            405                 410                 415

Pro Val Pro Phe Asp Leu Leu Phe Trp Asn Gly Asp Ala Thr Asn Leu
        420                 425                 430

Pro Gly Pro Trp Tyr Cys Trp Tyr Leu Arg His Thr Tyr Leu Gln Asn
    435                 440                 445

Glu Leu Lys Val Pro Gly Lys Leu Thr Val Cys Gly Val Pro Val Asp
    450                 455                 460

Leu Ala Ser Ile Asp Val Pro Thr Tyr Ile Tyr Gly Ser Arg Glu Asp
465                 470                 475                 480

His Ile Val Pro Trp Thr Ala Ala Tyr Ala Ser Thr Ala Leu Leu Ala
            485                 490                 495

Asn Lys Leu Arg Phe Val Leu Gly Ala Ser Gly His Ile Ala Gly Val
        500                 505                 510

Ile Asn Pro Pro Ala Lys Asn Lys Arg Ser His Trp Thr Asn Asp Ala
    515                 520                 525

Leu Pro Glu Ser Pro Gln Gln Trp Leu Ala Gly Ala Ile Glu His His
    530                 535                 540

Gly Ser Trp Trp Pro Asp Trp Thr Ala Trp Leu Ala Gly Gln Ala Gly
545                 550                 555                 560

Ala Lys Arg Ala Ala Pro Ala Asn Tyr Gly Asn Ala Arg Tyr Arg Ala
            565                 570                 575

Ile Glu Pro Ala Pro Gly Arg Tyr Val Lys Ala Lys Ala
        580                 585

<210> SEQ ID NO 9
<211> LENGTH: 1800
<212> TYPE: DNA
<213> ORGANISM: Rastonia Eutropia

<400> SEQUENCE: 9
ggatccatgg cgaccggcaa aggcgcggca gcttccacgc aggaaggcaa gtcccaacca      60
ttcaaggtca cgccggggcc attcgatcca gccacatggc tggaatggtc ccgccagtgg     120
cagggcactg aaggcaacgg ccacgcggcc gcgtccggca ttccgggcct ggatgcgctg     180
gcaggcgtca agatcgcgcc ggcgcagctg gtgatatcc agcagcgcta catgaaggac      240
ttctcagcgc tgtggcaggc catggccgag ggcaaggccg aggccaccgg tccgctgcac     300
gaccggcgct cgccggcga cgcatggcgc accaacctcc catatcgctt cgctgccgcg      360
ttctacctgc tcaatgcgcg cgccttgacc gagctggccg atgccgtcga ggccgatgcc     420
aagacccgcc agcgcatccg cttcgcgatc tcgcaatggg tcgatgcgat gtcgcccgcc     480
aacttccttg ccaccaatcc cgaggcgcag cgcctgctga tcgagtcggg cggcgaatcg     540
ctgcgtgccg gcgtgcgcaa catgatggaa gacctgacac gcggcaagat ctcgcagacc     600
gacgagagcg cgtttgaggt cggccgcaat gtcgcggtga ccgaaggcgc cgtggtcttc     660
gagaacgagt acttccagct gttgcagtac aagccgctga ccgacaaggt gcacgcgcgc     720
ccgctgctga tggtgccgcc gtgcatcaac aagtactaca tcctggacct gcagccggag     780
agctcgctgg tgccgccatgt ggtggagcag ggacatacgg tgtttctggt gtcgtggcgc     840
aatccggacg ccagcatggc cggcagcacc tgggacgact acatcgagca cgcggccatc     900
cgcgccatcg aagtcgcgcg cgacatcagc ggccaggaca agatcaacgt gctcggcttc     960
```

```
tgcgtgggcg gcaccattgt ctcgaccgcg ctggcggtgc tggccgcgcg cggcgagcac      1020
ccggccgcca gcgtcacgct gctgaccacg ctgctggact tgccgacac  gggcatcctc      1080 gacgtctttg tcgacgaggg ccatgtgcag ttgcgcgagg ccacgctggg cggcggcgcc      1140
ggcgcgccgt gcgcgctgct gcgcggcctt gagctggcca ataccttctc gttcttgcgc      1200
ccgaacgacc tggtgtggaa ctacgtggtc gacaactacc tgaagggcaa cacgccggtg      1260
ccgttcgacc tgctgttctg gaacggcgac gccaccaacc tgccggggcc gtggtactgc      1320
tggtacctgc gccacaccta cctgcagaac gagctcaagg taccgggcaa gctgaccgtg      1380
tgcggcgtgc cggtggacct ggccagcatc gacgtgccga cctatatcta cggctcgcgc      1440
gaagaccata tcgtgccgtg gaccgcggcc tatgcctcga ccgcgctgct ggcgaacaag      1500
ctgcgcttcg tgctgggtgc gtcgggccat atcgccggtg tgatcaaccc gccggccaag      1560
aacaagcgca gccactggac taacgatgcg ctgccggagt cgccgcagca atggctggcc      1620
ggcgccatcg agcatcacgg cagctggtgg ccggactgga ccgcatggct ggccgggcag      1680
gccggcgcga aacgcgccgc gcccgccaac tatggcaatg cgcgctatcg cgcaatcgaa      1740
cccgcgcctg gcgatacgt  caaagccaag gcatgacgct tcaatcgaat tggggtacc       1800
```

<210> SEQ ID NO 10
<211> LENGTH: 1428
<212> TYPE: DNA
<213> ORGANISM: Rastonia Eutropia
<220> FEATURE:
<221> NAME/KEY: CDS
<222> LOCATION: (1)..(1428)

<400> SEQUENCE: 10

```
atg gct tct atg ata tcc tct tcc gct gtg aca aca gtc agc cgt gcc       48
Met Ala Ser Met Ile Ser Ser Ser Ala Val Thr Thr Val Ser Arg Ala
1               5                   10                  15 tct agg ggg caa tcc gcc gca atg gct cca ttc ggc ggc ctc aaa tcc       96
Ser Arg Gly Gln Ser Ala Ala Met Ala Pro Phe Gly Gly Leu Lys Ser
            20                  25                  30 atg act gga ttc cca gtg aag aag gtc aac act gac att act tcc att      144
Met Thr Gly Phe Pro Val Lys Lys Val Asn Thr Asp Ile Thr Ser Ile
        35                  40                  45 aca agc aat ggt gga aga gta aag tgc atg cag gtg tgg cct cca att      192
Thr Ser Asn Gly Gly Arg Val Lys Cys Met Gln Val Trp Pro Pro Ile
    50                  55                  60 gga aag aag aag ttt gag act ctt tcc tat ttg cca cca ttg acc aga      240
Gly Lys Lys Lys Phe Glu Thr Leu Ser Tyr Leu Pro Pro Leu Thr Arg
65                  70                  75                  80 gat tcc cgg gtg act gac gtt gtc atc gta tcc gcc gcc cgc acc gcg      288
Asp Ser Arg Val Thr Asp Val Val Ile Val Ser Ala Ala Arg Thr Ala
                85                  90                  95 gtc ggc aag ttt ggc ggc tcg ctg gcc aag atc ccg gca ccg gaa ctg      336
Val Gly Lys Phe Gly Gly Ser Leu Ala Lys Ile Pro Ala Pro Glu Leu
            100                 105                 110 ggt gcc gtg gtc atc aag gcc gcg ctg gag cgc gcc ggc gtc aag ccg      384
Gly Ala Val Val Ile Lys Ala Ala Leu Glu Arg Ala Gly Val Lys Pro
        115                 120                 125 gag cag gtg agc gaa gtc atc atg ggc cag gtg ctg acc gcc ggt tcg      432
Glu Gln Val Ser Glu Val Ile Met Gly Gln Val Leu Thr Ala Gly Ser
    130                 135                 140 ggc cag aac ccc gca cgc cag gcc gcg atc aag gcc ggc ctg ccg gcg      480
Gly Gln Asn Pro Ala Arg Gln Ala Ala Ile Lys Ala Gly Leu Pro Ala
145                 150                 155                 160
```

-continued

| | |
|---|---|
| atg gtg ccg gcc atg acc atc aac aag gtg tgc ggc tcg ggc ctg aag<br>Met Val Pro Ala Met Thr Ile Asn Lys Val Cys Gly Ser Gly Leu Lys<br>                                      165                      170                      175 | 528 |
| gcc gtg atg ctg gcc gcc aac gcg atc atg gcg ggc gac gcc gag atc<br>Ala Val Met Leu Ala Ala Asn Ala Ile Met Ala Gly Asp Ala Glu Ile<br>            180                          185                          190 | 576 |
| gtg gtg gcc ggc ggc cag gaa aac atg agc gcc gcc ccg cac gtg ctg<br>Val Val Ala Gly Gly Gln Glu Asn Met Ser Ala Ala Pro His Val Leu<br>      195                          200                          205 | 624 |
| ccg ggc tcg cgc gat ggt ttc cgc atg ggc gat gcc aag ctg gtc gac<br>Pro Gly Ser Arg Asp Gly Phe Arg Met Gly Asp Ala Lys Leu Val Asp<br>210                          215                          220 | 672 |
| acc atg atc gtc gac ggc ctg tgg gac gtg tac aac cag tac cac atg<br>Thr Met Ile Val Asp Gly Leu Trp Asp Val Tyr Asn Gln Tyr His Met<br>225                      230                          235                      240 | 720 |
| ggc atc acc gcc gag aac gtg gcc aag gaa tac ggc atc aca cgc gag<br>Gly Ile Thr Ala Glu Asn Val Ala Lys Glu Tyr Gly Ile Thr Arg Glu<br>                      245                          250                          255 | 768 |
| gcg cag gat gag ttc gcc gtc ggc tcg cag aac aag gcc gaa gcc gcg<br>Ala Gln Asp Glu Phe Ala Val Gly Ser Gln Asn Lys Ala Glu Ala Ala<br>            260                          265                          270 | 816 |
| cag aag gcc ggc aag ttt gac gaa gag atc gtc ccg gtg ctg atc ccg<br>Gln Lys Ala Gly Lys Phe Asp Glu Glu Ile Val Pro Val Leu Ile Pro<br>      275                          280                          285 | 864 |
| cag cgc aag ggc gac ccg gtg gcc ttc aag acc gac gag ttc gtg cgc<br>Gln Arg Lys Gly Asp Pro Val Ala Phe Lys Thr Asp Glu Phe Val Arg<br>          290                          295                          300 | 912 |
| cag ggc gcc acg ctg gac agc atg tcc ggc ctc aag ccc gcc ttc gac<br>Gln Gly Ala Thr Leu Asp Ser Met Ser Gly Leu Lys Pro Ala Phe Asp<br>305                      310                          315                      320 | 960 |
| aag gcc ggc acg gtg acc gcg gcc aac gcc tcg ggc ctg aac gac ggc<br>Lys Ala Gly Thr Val Thr Ala Ala Asn Ala Ser Gly Leu Asn Asp Gly<br>                      325                          330                          335 | 1008 |
| gcc gcc gcg gtg gtg gtg atg tcg gcg gcc aag gcc aag gaa ctg ggc<br>Ala Ala Ala Val Val Val Met Ser Ala Ala Lys Ala Lys Glu Leu Gly<br>            340                          345                          350 | 1056 |
| ctg acc ccg ctg gcc acg atc aag agc tat gcc aac gcc ggt gtc gat<br>Leu Thr Pro Leu Ala Thr Ile Lys Ser Tyr Ala Asn Ala Gly Val Asp<br>      355                          360                          365 | 1104 |
| ccc aag gtg atg ggc atg ggc ccg gtg ccg gcc tcc aag cgc gcc ctg<br>Pro Lys Val Met Gly Met Gly Pro Val Pro Ala Ser Lys Arg Ala Leu<br>          370                          375                          380 | 1152 |
| tcg cgc gcc gag tgg acc ccg caa gac ctg gac ctg atg gag atc aac<br>Ser Arg Ala Glu Trp Thr Pro Gln Asp Leu Asp Leu Met Glu Ile Asn<br>385                      390                          395                      400 | 1200 |
| gag gcc ttt gcc gcc cag gcg ctg gcg gtg cac cag cag atg ggc tgg<br>Glu Ala Phe Ala Ala Gln Ala Leu Ala Val His Gln Gln Met Gly Trp<br>                      405                          410                          415 | 1248 |
| gac acc tcc aag gtc aat gtg aac ggc ggc gcc atc gcc atc ggc cac<br>Asp Thr Ser Lys Val Asn Val Asn Gly Gly Ala Ile Ala Ile Gly His<br>            420                          425                          430 | 1296 |
| ccg atc ggc gcg tcg ggc tgc cgt atc ctg gtg acg ctg ctg cac gag<br>Pro Ile Gly Ala Ser Gly Cys Arg Ile Leu Val Thr Leu Leu His Glu<br>      435                          440                          445 | 1344 |
| atg aag cgc cgt gac gcg aag aag ggc ctg gcc tcg ctg tgc atc ggc<br>Met Lys Arg Arg Asp Ala Lys Lys Gly Leu Ala Ser Leu Cys Ile Gly<br>450                      455                          460 | 1392 |
| ggc ggc atg ggc gtg gcg ctg gca gtc gag cgc aaa<br>Gly Gly Met Gly Val Ala Leu Ala Val Glu Arg Lys<br>465                      470                        475 | 1428 |

<210> SEQ ID NO 11
<211> LENGTH: 476
<212> TYPE: PRT
<213> ORGANISM: Rastonia Eutropia

<400> SEQUENCE: 11

```
Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Lys Lys Val Asn Thr Asp Ile Thr Ser Ile
            35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Ser Arg Val Thr Asp Val Ile Val Ser Ala Ala Arg Thr Ala
                85                  90                  95

Val Gly Lys Phe Gly Gly Ser Leu Ala Lys Ile Pro Ala Pro Glu Leu
                100                 105                 110

Gly Ala Val Ile Lys Ala Ala Leu Glu Arg Ala Gly Val Lys Pro
            115                 120                 125

Glu Gln Val Ser Glu Val Ile Met Gly Gln Val Leu Thr Ala Gly Ser
            130                 135                 140

Gly Gln Asn Pro Ala Arg Gln Ala Ala Ile Lys Ala Gly Leu Pro Ala
145                 150                 155                 160

Met Val Pro Ala Met Thr Ile Asn Lys Val Cys Gly Ser Gly Leu Lys
                165                 170                 175

Ala Val Met Leu Ala Ala Asn Ala Ile Met Ala Gly Asp Ala Glu Ile
                180                 185                 190

Val Val Ala Gly Gly Gln Glu Asn Met Ser Ala Ala Pro His Val Leu
            195                 200                 205

Pro Gly Ser Arg Asp Gly Phe Arg Met Gly Asp Ala Lys Leu Val Asp
    210                 215                 220

Thr Met Ile Val Asp Gly Leu Trp Asp Val Tyr Asn Gln Tyr His Met
225                 230                 235                 240

Gly Ile Thr Ala Glu Asn Val Ala Lys Glu Tyr Gly Ile Thr Arg Glu
                245                 250                 255

Ala Gln Asp Glu Phe Ala Val Gly Ser Gln Asn Lys Ala Glu Ala Ala
            260                 265                 270

Gln Lys Ala Gly Lys Phe Asp Glu Glu Ile Val Pro Val Leu Ile Pro
            275                 280                 285

Gln Arg Lys Gly Asp Pro Val Ala Phe Lys Thr Asp Glu Phe Val Arg
            290                 295                 300

Gln Gly Ala Thr Leu Asp Ser Met Ser Gly Leu Lys Pro Ala Phe Asp
305                 310                 315                 320

Lys Ala Gly Thr Val Thr Ala Ala Asn Ala Ser Gly Leu Asn Asp Gly
                325                 330                 335

Ala Ala Ala Val Val Met Ser Ala Ala Lys Ala Lys Glu Leu Gly
            340                 345                 350

Leu Thr Pro Leu Ala Thr Ile Lys Ser Tyr Ala Asn Ala Gly Val Asp
            355                 360                 365

Pro Lys Val Met Gly Met Gly Pro Val Pro Ala Ser Lys Arg Ala Leu
```

-continued

```
                            370                 375                 380
Ser Arg Ala Glu Trp Thr Pro Gln Asp Leu Asp Leu Met Glu Ile Asn
385                 390                 395                 400

Glu Ala Phe Ala Ala Gln Ala Leu Ala Val His Gln Gln Met Gly Trp
                405                 410                 415

Asp Thr Ser Lys Val Asn Val Asn Gly Gly Ala Ile Ala Ile Gly His
            420                 425                 430

Pro Ile Gly Ala Ser Gly Cys Arg Ile Leu Val Thr Leu Leu His Glu
        435                 440                 445

Met Lys Arg Arg Asp Ala Lys Lys Gly Leu Ala Ser Leu Cys Ile Gly
450                 455                 460

Gly Gly Met Gly Val Ala Leu Ala Val Glu Arg Lys
465                 470                 475

<210> SEQ ID NO 12
<211> LENGTH: 1529
<212> TYPE: DNA
<213> ORGANISM: Rastonia Eutropia

<400> SEQUENCE: 12
ggatccccat ggcttctatg atatcctctt ccgctgtgac aacagtcagc cgtgcctcta      60
gggggcaatc cgccgcaatg gctccattcg gcggcctcaa atccatgact ggattcccag     120
tgaagaaggt caacactgac attacttcca ttacaagcaa tggtggaaga gtaaagtgca     180
tgcaggtgtg gcctccaatt ggaaagaaga agtttgagac tctttcctat ttgccaccat     240
tgaccagaga ttcccgggtg actgacgttg tcatcgtatc cgccgcccgc accgcggtcg     300
gcaagtttgg cggctcgctg ccaagatcc cggcaccgga actgggtgcc gtggtcatca     360
aggccgcgct ggagcgcgcc ggcgtcaagc cggagcaggt gagcgaagtc atcatgggcc     420
aggtgctgac cgccggttcg ggccagaacc ccgcacgcca ggccgcgatc aaggccggcc     480
tgccggcgat ggtgccggcc atgaccatca acaaggtgtg cggctcgggc ctgaaggccg     540
tgatgctggc cgccaacgcg atcatggcgg gcgacgccga tcgtggtg ccggcggcc     600 aggaaaacat gagcgccgcc ccgcacgtgc tgccgggctc gcgcgatggt ttccgcatgg     660
gcgatgccaa gctggtcgac accatgatcg tcgacggcct gtgggacgtg tacaaccagt     720
accacatggg catcaccgcc gagaacgtgg ccaaggaata cggcatcaca cgcgaggcgc     780
aggatgagtt cgccgtcggc tcgcagaaca aggccgaagc cgcgcagaag ccggcaagt     840 ttgacgaaga gatcgtcccg gtgctgatcc cgcagcgcaa gggcgacccg gtggccttca     900
agaccgacga gttcgtgcgc cagggcgcca cgctggacag catgtccggc ctcaagcccg     960
ccttcgacaa ggccggcacg gtgaccgcgg ccaacgcctc gggcctgaac gacggcgccg    1020
ccgcggtggt ggtgatgtcg gcggccaagg ccaaggaact gggcctgacc ccgctggcca    1080
cgatcaagag ctatgccaac gccggtgtcg atcccaaggt gatgggcatg ggcccggtgc    1140
cggcctccaa gcgcgccctg tcgcgcgccg agtggaccc gcaagacctg acctgatgg     1200 agatcaacga ggccttttgcc gcccaggcgc tggcggtgca ccagcagatg ggctgggaca    1260
cctccaaggt caatgtgaac ggcggcgcca tcgccatcgg ccacccgatc ggcgcgtcgg    1320
gctgccgtat cctggtgacg ctgctgcacg agatgaagcg ccgtgacgcg aagaagggcc    1380
tggcctcgct gtgcatcggc ggcggcatgg gcgtggcgct ggcagtcgag cgcaaataag    1440
gaagggtttt ccggggccg cgcgcggttg gcgcggaccc ggcgacgata acgaagccaa    1500
tcaaggagtg gacatgactc agggtacc                                       1529
```

<210> SEQ ID NO 13
<211> LENGTH: 987
<212> TYPE: DNA
<213> ORGANISM: Rastonia Eutropia
<220> FEATURE:
<221> NAME/KEY: CDS
<222> LOCATION: (1)..(987)

<400> SEQUENCE: 13

```
atg gct tct atg ata tcc tct tcc gct gtg aca aca gtc agc cgt gcc       48
Met Ala Ser Met Ile Ser Ser Ser Ala Val Thr Thr Val Ser Arg Ala
1               5                   10                  15 tct agg ggg caa tcc gcc gca atg gct cca ttc ggc ggc ctc aaa tcc       96
Ser Arg Gly Gln Ser Ala Ala Met Ala Pro Phe Gly Gly Leu Lys Ser
            20                  25                  30 atg act gga ttc cca gtg aag aag gtc aac act gac att act tcc att      144
Met Thr Gly Phe Pro Val Lys Lys Val Asn Thr Asp Ile Thr Ser Ile
        35                  40                  45 aca agc aat ggt gga aga gta aag tgc atg cag gtg tgg cct cca att      192
Thr Ser Asn Gly Gly Arg Val Lys Cys Met Gln Val Trp Pro Pro Ile
    50                  55                  60 gga aag aag aag ttt gag act ctt tcc tat ttg cca cca ttg acc aga      240
Gly Lys Lys Lys Phe Glu Thr Leu Ser Tyr Leu Pro Pro Leu Thr Arg
65                  70                  75                  80 gat tcc cgg gtg act cag cgc att gcg tat gtg acc ggc ggc atg ggt      288
Asp Ser Arg Val Thr Gln Arg Ile Ala Tyr Val Thr Gly Gly Met Gly
                85                  90                  95 ggt atc gga acc gcc att tgc cag cgg ctg gcc aag gat ggc ttt cgt      336
Gly Ile Gly Thr Ala Ile Cys Gln Arg Leu Ala Lys Asp Gly Phe Arg
            100                 105                 110 gtg gtg gcc ggt tgc ggc ccc aac tcg ccg cgc cgc gaa aag tgg ctg      384
Val Val Ala Gly Cys Gly Pro Asn Ser Pro Arg Arg Glu Lys Trp Leu
        115                 120                 125 gag cag cag aag gca ctg ggc ttc gat ttc att gcc tcg gaa ggc aat      432
Glu Gln Gln Lys Ala Leu Gly Phe Asp Phe Ile Ala Ser Glu Gly Asn
    130                 135                 140 gtg gct gac tgg gac tcg acc aag acc gca ttc gac aag gtc aag tcc      480
Val Ala Asp Trp Asp Ser Thr Lys Thr Ala Phe Asp Lys Val Lys Ser
145                 150                 155                 160 gag gtc ggc gag gtt gat gtg ctg atc aac aac gcc ggt atc acc cgc      528
Glu Val Gly Glu Val Asp Val Leu Ile Asn Asn Ala Gly Ile Thr Arg
                165                 170                 175 gac gtg gtg ttc cgc aag atg acc cgc gcc gac tgg gat gcg gtg atc      576
Asp Val Val Phe Arg Lys Met Thr Arg Ala Asp Trp Asp Ala Val Ile
            180                 185                 190 gac acc aac ctg acc tcg ctg ttc aac gtc acc aag cag gtg atc gac      624
Asp Thr Asn Leu Thr Ser Leu Phe Asn Val Thr Lys Gln Val Ile Asp
        195                 200                 205 ggc atg gcc gac cgt ggc tgg ggc cgc atc gtc aac atc tcg tcg gtg      672
Gly Met Ala Asp Arg Gly Trp Gly Arg Ile Val Asn Ile Ser Ser Val
    210                 215                 220 aac ggg cag aag ggc cag ttc ggc cag acc aac tac tcc acc gcc aag      720
Asn Gly Gln Lys Gly Gln Phe Gly Gln Thr Asn Tyr Ser Thr Ala Lys
225                 230                 235                 240 gcc ggc ctg cat ggc ttc acc atg gca ctg gcg cag gaa gtg gcg acc      768
Ala Gly Leu His Gly Phe Thr Met Ala Leu Ala Gln Glu Val Ala Thr
                245                 250                 255 aag ggc gtg acc gtc aac acg gtc tct ccg ggc tat atc gcc acc gac      816
Lys Gly Val Thr Val Asn Thr Val Ser Pro Gly Tyr Ile Ala Thr Asp
            260                 265                 270
```

```
atg gtc aag gcg atc cgc cag gac gtg ctc gac aag atc gtc gcg acg      864
Met Val Lys Ala Ile Arg Gln Asp Val Leu Asp Lys Ile Val Ala Thr
    275                 280                 285 atc ccg gtc aag cgc ctg ggc ctg cca gaa gag atc gcc tcg atc tgc      912
Ile Pro Val Lys Arg Leu Gly Leu Pro Glu Glu Ile Ala Ser Ile Cys
290                 295                 300 gcc tgg ttg tcg tcg gag gag tcc ggt ttc tcg acc ggc gcc gac ttc      960
Ala Trp Leu Ser Ser Glu Glu Ser Gly Phe Ser Thr Gly Ala Asp Phe
305                 310                 315                 320 tcg ctc aac ggc ggc ctg cat atg ggc                                  987
Ser Leu Asn Gly Gly Leu His Met Gly
                325

<210> SEQ ID NO 14
<211> LENGTH: 329
<212> TYPE: PRT
<213> ORGANISM: Rastonia Eutropia

<400> SEQUENCE: 14

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Ph

```
Ile Pro Val Lys Arg Leu Gly Leu Pro Glu Glu Ile Ala Ser Ile Cys
    290                 295                 300

Ala Trp Leu Ser Ser Glu Glu Ser Gly Phe Ser Thr Gly Ala Asp Phe
305                 310                 315                 320

Ser Leu Asn Gly Gly Leu His Met Gly
                325

<210> SEQ ID NO 15
<211> LENGTH: 1032
<212> TYPE: DNA
<213> ORGANISM: Rastonia Eutropia

<400> SEQUENCE: 15
ggatccatgg cttctatgat atcctcttcc gctgtgacaa cagtcagccg tgcctctagg      60
gggcaatccg ccgcaatggc tccattcggc ggcctcaaat ccatgactgg attcccagtg     120
aagaaggtca acactgacat tacttccatt acaagcaatg gtggaagagt aaagtgcatg     180
caggtgtggc ctccaattgg aaagaagaag tttgagactc tttcctattt gccaccattg     240
accagagatt cccgggtgac tcagcgcatt gcgtatgtga ccggcggcat gggtggtatc     300
ggaaccgcca tttgccagcg gctggccaag gatggctttc gtgtggtggc cggttgcggc     360
cccaactcgc cgcgccgcga aaagtggctg gagcagcaga aggcactggg cttcgatttc     420
attgcctcgg aaggcaatgt ggctgactgg gactcgacca gaccgcattc gacaaggtc      480 aagtccgagg tcggcgaggt tgatgtgctg atcaacaacg ccggtatcac ccgcgacgtg     540
gtgttccgca agatgacccg cgccgactgg gatgcggtga tcgacaccaa cctgacctcg     600
ctgttcaacg tcaccaagca ggtgatcgac ggcatggccg accgtggctg gggccgcatc     660
gtcaacatct cgtcggtgaa cgggcagaag gccagttcg ccagaccaa ctactccacc      720 gccaaggccg gcctgcatgg cttcaccatg gcactggcgc aggaagtggc gaccaagggc     780
gtgaccgtca acacggtctc tccgggctat atcgccaccg acatggtcaa ggcgatccgc     840
caggacgtgc tcgacaagat cgtcgcgacg atcccggtca agcgcctggg cctgccagaa     900
gagatcgcct cgatctgcgc ctggttgtcg tcggaggagt ccggtttctc gaccggcgcc     960
gacttctcgc tcaacggcgg cctgcatatg gctgacctg ccggcctggt tccaccagtc     1020 ggcagggta cc                                                         1032

<210> SEQ ID NO 16
<211> LENGTH: 2016
<212> TYPE: DNA
<213> ORGANISM: Rastonia Eutropia
<220> F

```
gga aag aag aag ttt gag act ctt tcc tat ttg cca cca ttg acc aga       240
Gly Lys Lys Lys Phe Glu Thr Leu Ser Tyr Leu Pro Pro Leu Thr Arg
 65              70                  75                  80 gat tcc cgg gtg gcg acc ggc aaa ggc gcg gca gct tcc acg cag gaa       288
Asp Ser Arg Val Ala Thr Gly Lys Gly Ala Ala Ala Ser Thr Gln Glu
                 85                  90                  95 ggc aag tcc caa cca ttc aag gtc acg ccg ggg cca ttc gat cca gcc       336
Gly Lys Ser Gln Pro Phe Lys Val Thr Pro Gly Pro Phe Asp Pro Ala
                100                 105                 110 aca tgg ctg gaa tgg tcc cgc cag tgg cag ggc act gaa ggc aac ggc       384
Thr Trp Leu Glu Trp Ser Arg Gln Trp Gln Gly Thr Glu Gly Asn Gly
            115                 120                 125 cac gcg gcc gcg tcc ggc att ccg ggc ctg gat gcg ctg gca ggc gtc       432
His Ala Ala Ala Ser Gly Ile Pro Gly Leu Asp Ala Leu Ala Gly Val
        130                 135                 140 aag atc gcg ccg gcg cag ctg ggt gat atc cag cag cgc tac atg aag       480
Lys Ile Ala Pro Ala Gln Leu Gly Asp Ile Gln Gln Arg Tyr Met Lys
145                 150                 155                 160 gac ttc tca gcg ctg tgg cag gcc atg gcc gag ggc aag gcc gag gcc       528
Asp Phe Ser Ala Leu Trp Gln Ala Met Ala Glu Gly Lys Ala Glu Ala
                165                 170                 175 acc ggt ccg ctg cac gac cgg cgc ttc gcc ggc gac gca tgg cgc acc       576
Thr Gly Pro Leu His Asp Arg Arg Phe Ala Gly Asp Ala Trp Arg Thr
                180                 185                 190 aac ctc cca tat cgc ttc gct gcc gcg ttc tac ctg ctc aat gcg cgc       624
Asn Leu Pro Tyr Arg Phe Ala Ala Ala Phe Tyr Leu Leu Asn Ala Arg
            195                 200                 205 gcc ttg acc gag ctg gcc gat gcc gtc gag gcc gat gcc aag acc cgc       672
Ala Leu Thr Glu Leu Ala Asp Ala Val Glu Ala Asp Ala Lys Thr Arg
        210                 215                 220 cag cgc atc cgc ttc gcg atc tcg caa tgg gtc gat gcg atg tcg ccc       720
Gln Arg Ile Arg Phe Ala Ile Ser Gln Trp Val Asp Ala Met Ser Pro
225                 230                 235                 240 gcc aac ttc ctt gcc acc aat ccc gag gcg cag cgc ctg ctg atc gag       768
Ala Asn Phe Leu Ala Thr Asn Pro Glu Ala Gln Arg Leu Leu Ile Glu
                245                 250                 255 tcg ggc ggc gaa tcg ctg cgt gcc ggc gtg cgc aac atg atg gaa gac       816
Ser Gly Gly Glu Ser Leu Arg Ala Gly Val Arg Asn Met Met Glu Asp
                260                 265                 270 ctg aca cgc ggc aag atc tcg cag acc gac gag agc gcg ttt gag gtc       864
Leu Thr Arg Gly Lys Ile Ser Gln Thr Asp Glu Ser Ala Phe Glu Val
            275                 280                 285 ggc cgc aat gtc gcg gtg acc gaa ggc gcc gtg gtc ttc gag aac gag       912
Gly Arg Asn Val Ala Val Thr Glu Gly Ala Val Val Phe Glu Asn Glu
        290                 295                 300 tac ttc cag ctg ttg cag tac aag ccg ctg acc gac aag gtg cac gcg       960
Tyr Phe Gln Leu Leu Gln Tyr Lys Pro Leu Thr Asp Lys Val His Ala
305                 310                 315                 320 cgc ccg ctg ctg atg gtg ccg ccg tgc atc aac aag tac tac atc ctg      1008
Arg Pro Leu Leu Met Val Pro Pro Cys Ile Asn Lys Tyr Tyr Ile Leu
                325                 330                 335 gac ctg cag ccg gag agc tcg ctg gtg cgc cat gtg gtg gag cag gga      1056
Asp Leu Gln Pro Glu Ser Ser Leu Val Arg His Val Val Glu Gln Gly
                340                 345                 350 cat acg gtg ttt ctg gtg tcg tgg cgc aat ccg gac gcc agc atg gcc      1104
His Thr Val Phe Leu Val Ser Trp Arg Asn Pro Asp Ala Ser Met Ala
            355                 360                 365 ggc agc acc tgg gac gac tac atc gag cac gcg gcc atc cgc gcc atc      1152
Gly Ser Thr Trp Asp Asp Tyr Ile Glu His Ala Ala Ile Arg Ala Ile
```

-continued

```
                          370                 375                 380
gaa gtc gcg cgc gac atc agc ggc cag gac aag atc aac gtg ctc ggc        1200
Glu Val Ala Arg Asp Ile Ser Gly Gln Asp Lys Ile Asn Val Leu Gly
385                 390                 395                 400 ttc tgc gtg ggc ggc acc att gtc tcg acc gcg ctg gcg gtg ctg gcc        1248
Phe Cys Val Gly Gly Thr Ile Val Ser Thr Ala Leu Ala Val Leu Ala
                405                 410                 415 gcg cgc ggc gag cac ccg gcc gcc agc gtc acg ctg ctg acc acg ctg        1296
Ala Arg Gly Glu His Pro Ala Ala Ser Val Thr Leu Leu Thr Thr Leu
            420                 425                 430 ctg gac ttt gcc gac acg ggc atc ctc gac gtc ttt gtc gac gag ggc        1344
Leu Asp Phe Ala Asp Thr Gly Ile Leu Asp Val Phe Val Asp Glu Gly
        435                 440                 445 cat gtg cag ttg cgc gag gcc acg ctg ggc ggc ggc gcc ggc gcg ccg        1392
His Val Gln Leu Arg Glu Ala Thr Leu Gly Gly Gly Ala Gly Ala Pro
    450                 455                 460 tgc gcg ctg ctg cgc ggc ctt gag ctg gcc aat acc ttc tcg ttc ttg        1440
Cys Ala Leu Leu Arg Gly Leu Glu Leu Ala Asn Thr Phe Ser Phe Leu
465                 470                 475                 480 cgc ccg aac gac ctg gtg tgg aac tac gtg gtc gac aac tac ctg aag        1488
Arg Pro Asn Asp Leu Val Trp Asn Tyr Val Val Asp Asn Tyr Leu Lys
                485                 490                 495 ggc aac acg ccg gtg ccg ttc gac ctg ctg ttc tgg aac ggc gac gcc        1536
Gly Asn Thr Pro Val Pro Phe Asp Leu Leu Phe Trp Asn Gly Asp Ala
            500                 505                 510 acc aac ctg ccg ggg ccg tgg tac tgc tgg tac ctg cgc cac acc tac        1584
Thr Asn Leu Pro Gly Pro Trp Tyr Cys Trp Tyr Leu Arg His Thr Tyr
        515                 520                 525 ctg cag aac gag ctc aag gta ccg ggc aag ctg acc gtg tgc ggc gtg        1632
Leu Gln Asn Glu Leu Lys Val Pro Gly Lys Leu Thr Val Cys Gly Val
    530                 535                 540 ccg gtg gac ctg gcc agc atc gac gtg ccg acc tat atc tac ggc tcg        1680
Pro Val Asp Leu Ala Ser Ile Asp Val Pro Thr Tyr Ile Tyr Gly Ser
545                 550                 555                 560 cgc gaa gac cat atc gtg ccg tgg acc gcg gcc tat gcc tcg acc gcg        1728
Arg Glu Asp His Ile Val Pro Trp Thr Ala Ala Tyr Ala Ser Thr Ala
                565                 570                 575 ctg ctg gcg aac aag ctg cgc ttc gtg ctg ggt gcg tcg ggc cat atc        1776
Leu Leu Ala Asn Lys Leu Arg Phe Val Leu Gly Ala Ser Gly His Ile
            580                 585                 590 gcc ggt gtg atc aac ccg ccg gcc aag aac aag cgc agc cac tgg act        1824
Ala Gly Val Ile Asn Pro Pro Ala Lys Asn Lys Arg Ser His Trp Thr
        595                 600                 605 aac gat gcg ctg ccg gag tcg ccg cag caa tgg ctg gcc ggc gcc atc        1872
Asn Asp Ala Leu Pro Glu Ser Pro Gln Gln Trp Leu Ala Gly Ala Ile
    610                 615                 620 gag cat cac ggc agc tgg tgg ccg gac tgg acc gca tgg ctg gcc ggg        1920
Glu His His Gly Ser Trp Trp Pro Asp Trp Thr Ala Trp Leu Ala Gly
625                 630                 635                 640 cag gcc ggc gcg aaa cgc gcc gcg ccc gcc aac tat ggc aat gcg cgc        1968
Gln Ala Gly Ala Lys Arg Ala Ala Pro Ala Asn Tyr Gly Asn Ala Arg
                645                 650                 655 tat cgc gca atc gaa ccc gcg cct ggg cga tac gtc aaa gcc aag gca        2016
Tyr Arg Ala Ile Glu Pro Ala Pro Gly Arg Tyr Val Lys Ala Lys Ala
            660                 665                 670

<210> SEQ ID NO 17
<211> LENGTH: 672
<212> TYPE: PRT
<213> ORGANISM: Rastonia Eutropia
```

```
<400> SEQUENCE: 17

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Gln Val Trp Pro Ile
    50                  55                  60

Gly Lys Lys Lys Phe Glu Thr Leu Ser Tyr Leu Pro Pro Leu Thr Arg
65              70                  75                  80

Asp Ser Arg Val Ala Thr Gly Lys Gly Ala Ala Ser Thr Gln Glu
            85                  90                  95

Gly Lys Ser Gln Pro Phe Lys Val Thr Pro Gly Pro Phe Asp Pro Ala
            100                 105                 110

Thr Trp Leu Glu Trp Ser Arg Gln Trp Gln Gly Thr Glu Gly Asn Gly
        115                 120                 125

His Ala Ala Ser Gly Ile Pro Gly Leu Asp Ala Leu Ala Gly Val
    130                 135                 140

Lys Ile Ala Pro Ala Gln Leu Gly Asp Ile Gln Gln Arg Tyr Met Lys
145                 150                 155                 160

Asp Phe Ser Ala Leu Trp Gln Ala Met Ala Glu Gly Lys Ala Glu Ala
            165                 170                 175

Thr Gly Pro Leu His Asp Arg Arg Phe Ala Gly Asp Ala Trp Arg Thr
        180                 185                 190

Asn Leu Pro Tyr Arg Phe Ala Ala Ala Phe Tyr Leu Leu Asn Ala Arg
    195                 200                 205

Ala Leu Thr Glu Leu Ala Asp Ala Val Glu Ala Asp Ala Lys Thr Arg
    210                 215                 220

Gln Arg Ile Arg Phe Ala Ile Ser Gln Trp Val Asp Ala Met Ser Pro
225                 230                 235                 240

Ala Asn Phe Leu Ala Thr Asn Pro Glu Ala Gln Arg Leu Leu Ile Glu
            245                 250                 255

Ser Gly Gly Glu Ser Leu Arg Ala Gly Val Arg Asn Met Met Glu Asp
        260                 265                 270

Leu Thr Arg Gly Lys Ile Ser Gln Thr Asp Glu Ser Ala Phe Glu Val
    275                 280                 285

Gly Arg Asn Val Ala Val Thr Glu Gly Ala Val Phe Glu Asn Glu
            290                 295                 300

Tyr Phe Gln Leu Leu Gln Tyr Lys Pro Leu Thr Asp Lys Val His Ala
305                 310                 315                 320

Arg Pro Leu Leu Met Val Pro Pro Cys Ile Asn Lys Tyr Tyr Ile Leu
            325                 330                 335

Asp Leu Gln Pro Glu Ser Ser Leu Val Arg His Val Glu Gln Gly
            340                 345                 350

His Thr Val Phe Leu Val Ser Trp Arg Asn Pro Asp Ala Ser Met Ala
        355                 360                 365

Gly Ser Thr Trp Asp Asp Tyr Ile Glu His Ala Ile Arg Ala Ile
    370                 375                 380

Glu Val Ala Arg Asp Ile Ser Gly Gln Asp Lys Ile Asn Val Leu Gly
385                 390                 395                 400

Phe Cys Val Gly Gly Thr Ile Val Ser Thr Ala Leu Ala Val Leu Ala
```

-continued

```
                405                 410                 415
Ala Arg Gly Glu His Pro Ala Ala Ser Val Thr Leu Leu Thr Thr Leu
            420                 425                 430

Leu Asp Phe Ala Asp Thr Gly Ile Leu Asp Val Phe Asp Glu Gly
        435                 440                 445

His Val Gln Leu Arg Glu Ala Thr Leu Gly Gly Gly Ala Gly Ala Pro
    450                 455                 460

Cys Ala Leu Leu Arg Gly Leu Glu Leu Ala Asn Thr Phe Ser Phe Leu
465                 470                 475                 480

Arg Pro Asn Asp Leu Val Trp Asn Tyr Val Val Asp Asn Tyr Leu Lys
                485                 490                 495

Gly Asn Thr Pro Val Pro Phe Asp Leu Leu Phe Trp Asn Gly Asp Ala
            500                 505                 510

Thr Asn Leu Pro Gly Pro Trp Tyr Cys Trp Tyr Leu Arg His Thr Tyr
        515                 520                 525

Leu Gln Asn Glu Leu Lys Val Pro Gly Lys Leu Thr Val Cys Gly Val
    530                 535                 540

Pro Val Asp Leu Ala Ser Ile Asp Val Pro Thr Tyr Ile Tyr Gly Ser
545                 550                 555                 560

Arg Glu Asp His Ile Val Pro Trp Thr Ala Ala Tyr Ala Ser Thr Ala
                565                 570                 575

Leu Leu Ala Asn Lys Leu Arg Phe Val Leu Gly Ala Ser Gly His Ile
            580                 585                 590

Ala Gly Val Ile Asn Pro Pro Ala Lys Asn Lys Arg Ser His Trp Thr
        595                 600                 605

Asn Asp Ala Leu Pro Glu Ser Pro Gln Gln Trp Leu Ala Gly Ala Ile
    610                 615                 620

Glu His His Gly Ser Trp Trp Pro Asp Trp Thr Ala Trp Leu Ala Gly
625                 630                 635                 640

Gln Ala Gly Ala Lys Arg Ala Ala Pro Ala Asn Tyr Gly Asn Ala Arg
                645                 650                 655

Tyr Arg Ala Ile Glu Pro Ala Pro Gly Arg Tyr Val Lys Ala Lys Ala
            660                 665                 670
```

<210> SEQ ID NO 18
<211> LENGTH: 2049
<212> TYPE: DNA
<213> ORGANISM: Rastonia Eutropia

<400> SEQUENCE: 18

```
ggatccatgg cttctatgat atcctcttcc gctgtgacaa cagtcagccg tgcctctagg      60
gggcaatccg ccgcaatggc tccattcggc ggcctcaaat ccatgactgg attcccagtg     120
aagaaggtca acactgacat tacttccatt acaagcaatg gtggaagagt aaagtgcatg     180
caggtgtggc ctccaattgg aaagaagaag tttgagactc tttcctattt gccaccattg     240
accagagatt cccgggtggc gaccggcaaa ggcgcggcag cttccacgca ggaaggcaag     300
tcccaaccat tcaaggtcac gccggggcca ttcgatccag ccacatggct ggaatggtcc     360
cgccagtggc agggcactga aggcaacggc cacgcggccg cgtccggcat tccgggcctg     420
gatgcgctgg caggcgtcaa gatcgcgccg gcgcagctgg tgatatcca gcagcgctac     480
atgaaggact tctcagcgct gtggcaggcc atggccgagg caaggccga ggccaccggt     540
ccgctgcacg accggcgctt cgccggcgac gcatggcgca ccaacctccc atatcgcttc     600
gctgccgcgt tctacctgct caatgcgcgc gccttgaccg agctggccga tgccgtcgag     660
```

-continued

```
gccgatgcca agacccgcca gcgcatccgc ttcgcgatct cgcaatgggt cgatgcgatg      720
tcgcccgcca acttccttgc caccaatccc gaggcgcagc gcctgctgat cgagtcgggc      780
ggcgaatcgc tgcgtgccgg cgtgcgcaac atgatggaag acctgacacg cggcaagatc      840
tcgcagaccg acgagagcgc gtttgaggtc ggccgcaatg tcgcggtgac cgaaggcgcc      900
gtggtcttcg agaacgagta cttccagctg ttgcagtaca agccgctgac cgacaaggtg      960
cacgcgcgcc cgctgctgat ggtgccgccg tgcatcaaca agtactacat cctggacctg     1020
cagccggaga gctcgctggt gcgccatgtg gtggagcagg acatacggt gtttctggtg       1080 tcgtggcgca atccggacgc cagcatggcc ggcagcacct gggacgacta catcgagcac     1140
gcggccatcc gcgccatcga agtcgcgcgc gacatcagcg ccaggacaa gatcaacgtg      1200 ctcggcttct gcgtgggcgg caccattgtc tcgaccgcgc tggcggtgct ggccgcgcgc     1260
ggcgagcacc cggccgccag cgtcacgctg ctgaccacgc tgctggactt tgccgacacg     1320
ggcatcctcg acgtctttgt cgacgagggc catgtgcagt gcgcgaggc cacgctgggc      1380 ggcggcgccg gcgcgccgtg cgcgctgctg cgcggccttg agctggccaa taccttctcg     1440
ttcttgcgcc cgaacgacct ggtgtggaac tacgtggtcg acaactacct gaagggcaac     1500
acgccggtgc cgttcgacct gctgttctgg aacggcgacg ccaccaacct gccggggccg     1560
tggtactgct ggtacctgcg ccacacctac ctgcagaacg agctcaaggt accgggcaag     1620
ctgaccgtgt gcggcgtgcc ggtggacctg ccagcatcg acgtgccgac ctatatctac      1680
ggctcgcgcg aagaccatat cgtgccgtgg accgcgccct atgcctcgac cgcgctgctg     1740
gcgaacaagc tgcgcttcgt gctgggtgcg tcgggccata tcgccggtgt gatcaacccg     1800
ccggccaaga acaagcgcag ccactggact aacgatgcgc tgccggagtc gccgcagcaa     1860
tggctggccg cgccatcga gcatcacggc agctggtggc cggactggac cgcatggctg      1920
gccgggcagg ccggcgcgaa acgcgccgcg cccgccaact atggcaatgc cgctatcgc      1980 gcaatcgaac ccgcgcctgg gcgatacgtc aaagccaagg catgacgctt caatcgaatt     2040
gggggtacc                                                            2049
```

```
<210> SEQ ID NO 19
<211> LENGTH: 1680
<212> TYPE: DNA
<213> ORGANISM: P. aeruginosa
<220> FEATURE:
<221> NAME/KEY: CDS
<222> LOCATION: (1)..(1680)

<400> SEQUENCE: 19 atg agt cag aag aac aat aac gag ctt ccc aag caa gcc gcg gaa aac        48
Met Ser Gln Lys Asn Asn Asn Glu Leu Pro Lys Gln Ala Ala Glu Asn
1               5                   10                  15 acg ctg aac ctg aat ccg gtg atc ggc atc cgg ggc aag gac ctg ctc        96
Thr Leu Asn Leu Asn Pro Val Ile Gly Ile Arg Gly Lys Asp Leu Leu
            20                  25                  30 acc tcc gcg cgc atg gtc ctg ctc cag gcg gtg cgc cag ccg ctg cac       144
Thr Ser Ala Arg Met Val Leu Leu Gln Ala Val Arg Gln Pro Leu His
        35                  40                  45 agc gcc agg cac gtg gcg cat ttc agc ctg gag ctg aag aac gtc ctg       192
Ser Ala Arg His Val Ala His Phe Ser Leu Glu Leu Lys Asn Val Leu
    50                  55                  60 ctc ggc cag tcg gag cta cgc cca ggc gat gac gac cga cgc ttt tcc       240
Leu Gly Gln Ser Glu Leu Arg Pro Gly Asp Asp Asp Arg Arg Phe Ser
65                  70                  75                  80
```

```
gat ccg gcc tgg agc cag aat cca ctg tac aag cgc tac atg cag acc      288
Asp Pro Ala Trp Ser Gln Asn Pro Leu Tyr Lys Arg Tyr Met Gln Thr
             85                  90                  95 tac ctg gcc tgg cgc aag gag ctg cac agc tgg atc agc cac agc gac      336
Tyr Leu Ala Trp Arg Lys Glu Leu His Ser Trp Ile Ser His Ser Asp
            100                 105                 110 ctg tcg ccg cag gac atc agt cgt ggc cag ttc gtc atc aac ctg ctg      384
Leu Ser Pro Gln Asp Ile Ser Arg Gly Gln Phe Val Ile Asn Leu Leu
        115                 120                 125 acc gag gcg atg tcg ccg acc aac agc ctg agc aac ccg gcg gcg gtc      432
Thr Glu Ala Met Ser Pro Thr Asn Ser Leu Ser Asn Pro Ala Ala Val
    130                 135                 140 aag cgc ttc ttc gag acc ggc ggc aag agc ctg ctg gac ggc ctc ggc      480
Lys Arg Phe Phe Glu Thr Gly Gly Lys Ser Leu Leu Asp Gly Leu Gly
145                 150                 155                 160 cac ctg gcc aag gac ctg gtg aac aac ggc ggg atg ccg agc cag gtg      528
His Leu Ala Lys Asp Leu Val Asn Asn Gly Gly Met Pro Ser Gln Val
                165                 170                 175 gac atg gac gcc ttc gag gtg ggc aag aac ctg gcc acc acc gag ggc      576
Asp Met Asp Ala Phe Glu Val Gly Lys Asn Leu Ala Thr Thr Glu Gly
            180                 185                 190 gcc gtg gtg ttc cgc aac gac gtg ctg gaa ctg atc cag tac cgg ccg      624
Ala Val Val Phe Arg Asn Asp Val Leu Glu Leu Ile Gln Tyr Arg Pro
        195                 200                 205 atc acc gag tcg gtg cac gaa cgc ccg ctg ctg gtg gtg ccg ccg cag      672
Ile Thr Glu Ser Val His Glu Arg Pro Leu Leu Val Val Pro Pro Gln
    210                 215                 220 atc aac aag ttc tac gtc ttc gac ctg tcg ccg gac aag agc ctg gcg      720
Ile Asn Lys Phe Tyr Val Phe Asp Leu Ser Pro Asp Lys Ser Leu Ala
225                 230                 235                 240 cgc ttc tgc ctg cgc aac ggc gtg cag acc ttc atc gtc agt tgg cgc      768
Arg Phe Cys Leu Arg Asn Gly Val Gln Thr Phe Ile Val Ser Trp Arg
                245                 250                 255 aac ccg acc aag tcg cag cgc gaa tgg ggc ctg acc acc tat atc gag      816
Asn Pro Thr Lys Ser Gln Arg Glu Trp Gly Leu Thr Thr Tyr Ile Glu
            260                 265                 270 gcg ctc aag gag gcc atc gag gta gtc ctg tcg atc acc ggc agc aag      864
Ala Leu Lys Glu Ala Ile Glu Val Val Leu Ser Ile Thr Gly Ser Lys
        275                 280                 285 gac ctc aac ctc ctc ggc gcc tgc tcc ggc ggg atc acc acc gcg acc      912
Asp Leu Asn Leu Leu Gly Ala Cys Ser Gly Gly Ile Thr Thr Ala Thr
    290                 295                 300 ctg gtc ggc cac tac gtg gcc agc ggc gag aag aag gtc aac gcc ttc      960
Leu Val Gly His Tyr Val Ala Ser Gly Glu Lys Lys Val Asn Ala Phe
305                 310                 315                 320 acc caa ctg gtc agc gtg ctc gac ttc gaa ctg aat acc cag gtc gcg     1008
Thr Gln Leu Val Ser Val Leu Asp Phe Glu Leu Asn Thr Gln Val Ala
                325                 330                 335 ctg ttc gcc gac gag aag act ctg gag gcc gcc aag cgt cgt tcc tac     1056
Leu Phe Ala Asp Glu Lys Thr Leu Glu Ala Ala Lys Arg Arg Ser Tyr
            340                 345                 350 cag tcc ggc gtg ctg gag ggc aag gac atg gcc aag gtg ttc gcc tgg     1104
Gln Ser Gly Val Leu Glu Gly Lys Asp Met Ala Lys Val Phe Ala Trp
        355                 360                 365 atg cgc ccc aac gac ctg atc tgg aac tac tgg gtc aac aac tac ctg     1152
Met Arg Pro Asn Asp Leu Ile Trp Asn Tyr Trp Val Asn Asn Tyr Leu
    370                 375                 380 ctc ggc aac cag ccg ccg gcg ttc gac atc ctc tac tgg aac aac gac     1200
Leu Gly Asn Gln Pro Pro Ala Phe Asp Ile Leu Tyr Trp Asn Asn Asp
```

```
                385                 390                 395                 400
acc acg cgc ctg ccc gcc gcg ctg cac ggc gag ttc gtc gaa ctg ttc        1248
Thr Thr Arg Leu Pro Ala Ala Leu His Gly Glu Phe Val Glu Leu Phe
                405                 410                 415 aag agc aac ccg ctg aac cgc ccc ggc gcc ctg gag gtc tcc ggc acg        1296
Lys Ser Asn Pro Leu Asn Arg Pro Gly Ala Leu Glu Val Ser Gly Thr
            420                 425                 430 ccc atc gac ctg aag cag gtg act tgc gac ttc tac tgt gtc gcc ggt        1344
Pro Ile Asp Leu Lys Gln Val Thr Cys Asp Phe Tyr Cys Val Ala Gly
        435                 440                 445 ctg aac gac cac atc acc ccc tgg gag tcg tgc tac aag tcg gcc agg        1392
Leu Asn Asp His Ile Thr Pro Trp Glu Ser Cys Tyr Lys Ser Ala Arg
    450                 455                 460 ctg ctg ggt ggc aag tgc gag ttc atc ctc tcc aac agc ggt cac atc        1440
Leu Leu Gly Gly Lys Cys Glu Phe Ile Leu Ser Asn Ser Gly His Ile
465                 470                 475                 480 cag agc atc ctc aac cca ccg ggc aac ccc aag gca cgc ttc atg acc        1488
Gln Ser Ile Leu Asn Pro Pro Gly Asn Pro Lys Ala Arg Phe Met Thr
                485                 490                 495 aat ccg gaa ctg ccc gcc gag ccc aag gcc tgg ctg gaa cag gcc ggc        1536
Asn Pro Glu Leu Pro Ala Glu Pro Lys Ala Trp Leu Glu Gln Ala Gly
            500                 505                 510 aag cac gcc gac tcg tgg tgg ttg cac tgg cag caa tgg ctg gcc gaa        1584
Lys His Ala Asp Ser Trp Trp Leu His Trp Gln Gln Trp Leu Ala Glu
        515                 520                 525 cgc tcc ggc aag acc cgc aag gcg ccc gcc agc ctg ggc aac aag acc        1632
Arg Ser Gly Lys Thr Arg Lys Ala Pro Ala Ser Leu Gly Asn Lys Thr
    530                 535                 540 tat ccg gcc ggc gaa gcc gcg ccc gga acc tac gtg cat gaa cga tga        1680
Tyr Pro Ala Gly Glu Ala Ala Pro Gly Thr Tyr Val His Glu Arg
545                 550                 555

<210> SEQ ID NO 20
<211> LENGTH: 559
<212> TYPE: PRT
<213> ORGANISM: P. aeruginosa

<400> SEQUENCE: 20

Met Ser Gln Lys Asn Asn Asn Glu Leu Pro Lys Gln Ala Ala Glu Asn
1               5                   10                  15

Thr Leu Asn Leu Asn Pro Val Ile Gly Ile Arg Gly Lys Asp Leu Leu
            20                  25                  30

Thr Ser Ala Arg Met Val Leu Leu Gln Ala Val Arg Gln Pro Leu His
        35                  40                  45

Ser Ala Arg His Val Ala His Phe Ser Leu Glu Leu Lys Asn Val Leu
    50                  55                  60

Leu Gly Gln Ser Glu Leu Arg Pro Gly Asp Asp Arg Arg Phe Ser
65              70                  75                  80

Asp Pro Ala Trp Ser Gln Asn Pro Leu Tyr Lys Arg Tyr Met Gln Thr
                85                  90                  95

Tyr Leu Ala Trp Arg Lys Glu Leu His Ser Trp Ile Ser His Ser Asp
            100                 105                 110

Leu Ser Pro Gln Asp Ile Ser Arg Gly Gln Phe Val Ile Asn Leu Leu
        115                 120                 125

Thr Glu Ala Met Ser Pro Thr Asn Ser Leu Ser Asn Pro Ala Ala Val
    130                 135                 140

Lys Arg Phe Phe Glu Thr Gly Gly Lys Ser Leu Leu Asp Gly Leu Gly
145                 150                 155                 160
```

-continued

```
His Leu Ala Lys Asp Leu Val Asn Asn Gly Gly Met Pro Ser Gln Val
                165                 170                 175

Asp Met Asp Ala Phe Glu Val Gly Lys Asn Leu Ala Thr Thr Glu Gly
            180                 185                 190

Ala Val Val Phe Arg Asn Asp Val Leu Glu Leu Ile Gln Tyr Arg Pro
        195                 200                 205

Ile Thr Glu Ser Val His Glu Arg Pro Leu Leu Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Gly Val Gln Thr Phe Ile Val Ser Trp Arg
                245                 250                 255

Asn Pro Thr Lys Ser Gln Arg Glu Trp Gly Leu Thr Thr Tyr Ile Glu
            260                 265                 270

Ala Leu Lys Glu Ala Ile Glu Val Val Leu Ser Ile Thr Gly Ser Lys
        275                 280                 285

Asp Leu Asn Leu Leu Gly Ala Cys Ser Gly Gly Ile Thr Thr Ala Thr
    290                 295                 300

Leu Val Gly His Tyr Val Ala Ser Gly Glu Lys Lys Val Asn Ala Phe
305                 310                 315                 320

Thr Gln Leu Val Ser Val Leu Asp Phe Glu Leu Asn Thr Gln Val Ala
                325                 330                 335

Leu Phe Ala Asp Glu Lys Thr Leu Glu Ala Ala Lys Arg Arg Ser Tyr
            340                 345                 350

Gln Ser Gly Val Leu Glu Gly Lys Asp Met Ala Lys Val Phe Ala Trp
        355                 360                 365

Met Arg Pro Asn Asp Leu Ile Trp Asn Tyr Trp Val Asn Asn Tyr Leu
    370                 375                 380

Leu Gly Asn Gln Pro Pro Ala Phe Asp Ile Leu Tyr Trp Asn Asn Asp
385                 390                 395                 400

Thr Thr Arg Leu Pro Ala Ala Leu His Gly Glu Phe Val Glu Leu Phe
                405                 410                 415

Lys Ser Asn Pro Leu Asn Arg Pro Gly Ala Leu Glu Val Ser Gly Thr
            420                 425                 430

Pro Ile Asp Leu Lys Gln Val Thr Cys Asp Phe Tyr Cys Val Ala Gly
        435                 440                 445

Leu Asn Asp His Ile Thr Pro Trp Glu Ser Cys Tyr Lys Ser Ala Arg
    450                 455                 460

Leu Leu Gly Gly Lys Cys Glu Phe Ile Leu Ser Asn Ser Gly His Ile
465                 470                 475                 480

Gln Ser Ile Leu Asn Pro Gly Asn Pro Lys Ala Arg Phe Met Thr
                485                 490                 495

Asn Pro Glu Leu Pro Ala Glu Pro Lys Ala Trp Leu Glu Gln Ala Gly
            500                 505                 510

Lys His Ala Asp Ser Trp Trp Leu His Trp Gln Gln Trp Leu Ala Glu
        515                 520                 525

Arg Ser Gly Lys Thr Arg Lys Ala Pro Ala Ser Leu Gly Asn Lys Thr
    530                 535                 540

Tyr Pro Ala Gly Glu Ala Ala Pro Gly Thr Tyr Val His Glu Arg
545                 550                 555

<210> SEQ ID NO 21
<211> LENGTH: 1692
```

<212> TYPE: DNA
<213> ORGANISM: P. aeruginosa

<400> SEQUENCE: 21

```
ggatccatga gtcagaagaa caataacgag cttcccaagc aagccgcgga aaacacgctg      60
aacctgaatc cggtgatcgg catccggggc aaggacctgc tcacctccgc gcgcatggtc     120
ctgctccagg cggtgcgcca gccgctgcac agcgccaggc acgtggcgca tttcagcctg     180
gagctgaaga acgtcctgct cggccagtcg agctacgcc caggcgatga cgaccgacgc      240
ttttccgatc cggcctggag ccagaatcca ctgtacaagc gctacatgca gacctacctg     300
gcctggcgca aggagctgca cagctggatc agccacagcg acctgtcgcc gcaggacatc     360
agtcgtggcc agttcgtcat caacctgctg accgaggcga tgtcgccgac caacagcctg     420
agcaacccgg cggcggtcaa gcgcttcttc gagaccggcg gcaagagcct gctggacggc     480
ctcggccacc tggccaagga cctggtgaac acggcggga tgccgagcca ggtggacatg      540
gacgccttcg aggtgggcaa gaacctggcc accaccgagg gcgccgtggt gttccgcaac     600
gacgtgctgg aactgatcca gtaccggccg atcaccgagt cggtgcacga acgcccgctg     660
ctggtggtgc cgccgcagat caacaagttc tacgtcttcg acctgtcgcc ggacaagagc     720
ctggcgcgct tctgcctgcg caacggcgtg cagaccttca tcgtcagttg gcgcaacccg     780
accaagtcgc agcgcgaatg gggcctgacc acctatatcg aggcgctcaa ggaggccatc     840
gaggtagtcc tgtcgatcac cggcagcaag gacctcaacc tcctcggcgc ctgctccggc     900
gggatcacca ccgcgaccct ggtcggccac tacgtggcca cggcgagaa gaaggtcaac      960
gccttcaccc aactggtcag cgtgctcgac ttcgaactga atacccaggt cgcgctgttc    1020
gccgacgaga agactctgga ggccgccaag cgtcgttcct accagtccgg cgtgctggag    1080
ggcaaggaca tggccaaggt gttcgcctgg atgcgcccca cgacctgat ctggaactac     1140
tgggtcaaca actacctgct cggcaaccag ccgccggcgt tcgacatcct ctactggaac    1200
aacgacacca cgcgcctgcc cgccgcgctg cacggcgagt tcgtcgaact gttcaagagc    1260
aacccgctga accgcccggg cgccctggag gtctccggca cgcccatcga cctgaagcag    1320
gtgacttgcg acttctactg tgtcgccggt ctgaacgacc acatcacccc ctgggagtcg    1380
tgctacaagt cggccaggct gctgggtggc aagtgcgagt catcctctc caacagcggt     1440
cacatccaga gcatcctcaa cccaccgggc aaccccaagg cacgcttcat gaccaatccg    1500
gaactgcccg ccgagcccaa ggcctggctg aacaggccg gcaagcacgc cgactcgtgg     1560
tggttgcact ggcagcaatg gctggccgaa cgctccggca agacccgcaa ggcgccgcc     1620
agcctgggca caagacccta tccggccggc gaagccgcgc ccggaaccta cgtgcatgaa    1680
cgatgaggta cc                                                         1692
```

<210> SEQ ID NO 22
<211> LENGTH: 1794
<212> TYPE: DNA
<213> ORGANISM: P. aeruginosa
<220> FEATURE:
<221> NAME/KEY: CDS
<222> LOCATION: (1)..(1794)

<400> SEQUENCE: 22

```
atg agt cag aag aac aat aac gag ctt ccc aag caa gcc gcg gaa aac       48
Met Ser Gln Lys Asn Asn Asn Glu Leu Pro Lys Gln Ala Ala Glu Asn
1               5                   10                  15 acg ctg aac ctg aat ccg gtg atc ggc atc cgg ggc aag gac ctg ctc       96
```

```
                Thr Leu Asn Leu Asn Pro Val Ile Gly Ile Arg Gly Lys Asp Leu Leu
                                20                  25                  30 acc tcc gcg cgc atg gtc ctg ctc cag gcg gtg cgc cag ccg ctg cac          144
Thr Ser Ala Arg Met Val Leu Leu Gln Ala Val Arg Gln Pro Leu His
         35                  40                  45 agc gcc agg cac gtg gcg cat ttc agc ctg gag ctg aag aac gtc ctg          192
Ser Ala Arg His Val Ala His Phe Ser Leu Glu Leu Lys Asn Val Leu
 50                  55                  60 ctc ggc cag tcg gag cta cgc cca ggc gat gac gac cga cgc ttt tcc          240
Leu Gly Gln Ser Glu Leu Arg Pro Gly Asp Asp Asp Arg Arg Phe Ser
 65                  70                  75                  80 gat ccg gcc tgg agc cag aat cca ctg tac aag cgc tac atg cag acc          288
Asp Pro Ala Trp Ser Gln Asn Pro Leu Tyr Lys Arg Tyr Met Gln Thr
                 85                  90                  95 tac ctg gcc tgg cgc aag gag ctg cac agc tgg atc agc cac agc gac          336
Tyr Leu Ala Trp Arg Lys Glu Leu His Ser Trp Ile Ser His Ser Asp
                100                 105                 110 ctg tcg ccg cag gac atc agt cgt ggc cag ttc gtc atc aac ctg ctg          384
Leu Ser Pro Gln Asp Ile Ser Arg Gly Gln Phe Val Ile Asn Leu Leu
         115                 120                 125 acc gag gcg atg tcg ccg acc aac agc ctg agc aac ccg gcg gcg gtc          432
Thr Glu Ala Met Ser Pro Thr Asn Ser Leu Ser Asn Pro Ala Ala Val
130                 135                 140 aag cgc ttc ttc gag acc ggc ggc aag agc ctg ctg gac ggc ctc ggc          480
Lys Arg Phe Phe Glu Thr Gly Gly Lys Ser Leu Leu Asp Gly Leu Gly
145                 150                 155                 160 cac ctg gcc aag gac ctg gtg aac aac ggc ggg atg ccg agc cag gtg          528
His Leu Ala Lys Asp Leu Val Asn Asn Gly Gly Met Pro Ser Gln Val
                165                 170                 175 gac atg gac gcc ttc gag gtg ggc aag aac ctg gcc acc acc gag ggc          576
Asp Met Asp Ala Phe Glu Val Gly Lys Asn Leu Ala Thr Thr Glu Gly
                180                 185                 190 gcc gtg gtg ttc cgc aac gac gtg ctg gaa ctg atc cag tac cgg ccg          624
Ala Val Val Phe Arg Asn Asp Val Leu Glu Leu Ile Gln Tyr Arg Pro
        195                 200                 205 atc acc gag tcg gtg cac gaa cgc ccg ctg ctg gtg gtg ccg ccg cag          672
Ile Thr Glu Ser Val His Glu Arg Pro Leu Leu Val Val Pro Pro Gln
210                 215                 220 atc aac aag ttc tac gtc ttc gac ctg tcg ccg gac aag agc ctg gcg          720
Ile Asn Lys Phe Tyr Val Phe Asp Leu Ser Pro Asp Lys Ser Leu Ala
225                 230                 235                 240 cgc ttc tgc ctg cgc aac ggc gtg cag acc ttc atc gtc agt tgg cgc          768
Arg Phe Cys Leu Arg Asn Gly Val Gln Thr Phe Ile Val Ser Trp Arg
                245                 250                 255 aac ccg acc aag tcg cag cgc gaa tgg ggc ctg acc acc tat atc gag          816
Asn Pro Thr Lys Ser Gln Arg Glu Trp Gly Leu Thr Thr Tyr Ile Glu
                260                 265                 270 gcg ctc aag gag gcc atc gag gta gtc ctg tcg atc acc ggc agc aag          864
Ala Leu Lys Glu Ala Ile Glu Val Val Leu Ser Ile Thr Gly Ser Lys
        275                 280                 285 gac ctc aac ctc ctc ggc gcc tgc tcc ggc ggg atc acc acc gcg acc          912
Asp Leu Asn Leu Leu Gly Ala Cys Ser Gly Gly Ile Thr Thr Ala Thr
290                 295                 300 ctg gtc ggc cac tac gtg gcc agc ggc gag aag aag gtc aac gcc ttc          960
Leu Val Gly His Tyr Val Ala Ser Gly Glu Lys Lys Val Asn Ala Phe
305                 310                 315                 320 acc caa ctg gtc agc gtg ctc gac ttc gaa ctg aat acc cag gtc gcg         1008
Thr Gln Leu Val Ser Val Leu Asp Phe Glu Leu Asn Thr Gln Val Ala
                325                 330                 335
```

```
ctg ttc gcc gac gag aag act ctg gag gcc gcc aag cgt cgt tcc tac    1056
Leu Phe Ala Asp Glu Lys Thr Leu Glu Ala Ala Lys Arg Arg Ser Tyr
            340                 345                 350 cag tcc ggc gtg ctg gag ggc aag gac atg gcc aag gtg ttc gcc tgg    1104
Gln Ser Gly Val Leu Glu Gly Lys Asp Met Ala Lys Val Phe Ala Trp
        355                 360                 365 atg cgc ccc aac gac ctg atc tgg aac tac tgg gtc aac aac tac ctg    1152
Met Arg Pro Asn Asp Leu Ile Trp Asn Tyr Trp Val Asn Asn Tyr Leu
    370                 375                 380 ctc ggc aac cag ccg ccg gcg ttc gac atc ctc tac tgg aac aac gac    1200
Leu Gly Asn Gln Pro Pro Ala Phe Asp Ile Leu Tyr Trp Asn Asn Asp
385                 390                 395                 400 acc acg cgc ctg ccc gcc gcg ctg cac ggc gag ttc gtc gaa ctg ttc    1248
Thr Thr Arg Leu Pro Ala Ala Leu His Gly Glu Phe Val Glu Leu Phe
                405                 410                 415 aag agc aac ccg ctg aac cgc ccc ggc gcc ctg gag gtc tcc ggc acg    1296
Lys Ser Asn Pro Leu Asn Arg Pro Gly Ala Leu Glu Val Ser Gly Thr
            420                 425                 430 ccc atc gac ctg aag cag gtg act tgc gac ttc tac tgt gtc gcc ggt    1344
Pro Ile Asp Leu Lys Gln Val Thr Cys Asp Phe Tyr Cys Val Ala Gly
        435                 440                 445 ctg aac gac cac atc acc ccc tgg gag tcg tgc tac aag tcg gcc agg    1392
Leu Asn Asp His Ile Thr Pro Trp Glu Ser Cys Tyr Lys Ser Ala Arg
    450                 455                 460 ctg ctg ggt ggc aag tgc gag ttc atc ctc tcc aac agc ggt cac atc    1440
Leu Leu Gly Gly Lys Cys Glu Phe Ile Leu Ser Asn Ser Gly His Ile
465                 470                 475                 480 cag agc atc ctc aac cca ccg ggc aac ccc aag gca cgc ttc atg acc    1488
Gln Ser Ile Leu Asn Pro Pro Gly Asn Pro Lys Ala Arg Phe Met Thr
                485                 490                 495 aat ccg gaa ctg ccc gcc gag ccc aag gcc tgg ctg gaa cag gcc ggc    1536
Asn Pro Glu Leu Pro Ala Glu Pro Lys Ala Trp Leu Glu Gln Ala Gly
            500                 505                 510 aag cac gcc gac tcg tgg tgg ttg cac tgg cag caa tgg ctg gcc gaa    1584
Lys His Ala Asp Ser Trp Trp Leu His Trp Gln Gln Trp Leu Ala Glu
        515                 520                 525 cgc tcc ggc aag acc cgc aag gcg ccc gcc agc ctg ggc aac aag acc    1632
Arg Ser Gly Lys Thr Arg Lys Ala Pro Ala Ser Leu Gly Asn Lys Thr
    530                 535                 540 tat ccg gcc ggc gaa gcc gcg ccc gga acc tac gtg cat gaa cga tca    1680
Tyr Pro Ala Gly Glu Ala Ala Pro Gly Thr Tyr Val His Glu Arg Ser
545                 550                 555                 560 aaa gct ttg ggc aaa ggt gtt acc gag gaa caa ttc aaa gag acc tgg    1728
Lys Ala Leu Gly Lys Gly Val Thr Glu Glu Gln Phe Lys Glu Thr Trp
                565                 570                 575 acg agg ccg gga gct gct gga atg ggc gaa ggg act agc ctt gtg gtg    1776
Thr Arg Pro Gly Ala Ala Gly Met Gly Glu Gly Thr Ser Leu Val Val
            580                 585                 590 gcc aag tcc aga atg taa                                            1794
Ala Lys Ser Arg Met
        595

<210> SEQ ID NO 23
<211> LENGTH: 597
<212> TYPE: PRT
<213> ORGANISM: P. aeruginosa

<400> SEQUENCE: 23

Met Ser Gln Lys Asn Asn Asn Glu Leu Pro Lys Gln Ala Ala Glu Asn
1               5                   10                  15
```

```
Thr Leu Asn Leu Asn Pro Val Ile Gly Ile Arg Gly Lys Asp Leu Leu
            20                  25                  30

Thr Ser Ala Arg Met Val Leu Leu Gln Ala Val Arg Gln Pro Leu His
        35                  40                  45

Ser Ala Arg His Val Ala His Phe Ser Leu Glu Leu Lys Asn Val Leu
50                      55                  60

Leu Gly Gln Ser Glu Leu Arg Pro Gly Asp Asp Arg Arg Phe Ser
65                  70                  75                  80

Asp Pro Ala Trp Ser Gln Asn Pro Leu Tyr Lys Arg Tyr Met Gln Thr
                85                  90                  95

Tyr Leu Ala Trp Arg Lys Glu Leu His Ser Trp Ile Ser His Ser Asp
                100                 105                 110

Leu Ser Pro Gln Asp Ile Ser Arg Gly Gln Phe Val Ile Asn Leu Leu
                115                 120                 125

Thr Glu Ala Met Ser Pro Thr Asn Ser Leu Ser Asn Pro Ala Ala Val
        130                 135                 140

Lys Arg Phe Phe Glu Thr Gly Gly Lys Ser Leu Leu Asp Gly Leu Gly
145                 150                 155                 160

His Leu Ala Lys Asp Leu Val Asn Asn Gly Met Pro Ser Gln Val
                165                 170                 175

Asp Met Asp Ala Phe Glu Val Gly Lys Asn Leu Ala Thr Thr Glu Gly
                180                 185                 190

Ala Val Val Phe Arg Asn Asp Val Leu Glu Leu Ile Gln Tyr Arg Pro
            195                 200                 205

Ile Thr Glu Ser Val His Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Gly Val Gln Thr Phe Ile Val Ser Trp Arg
                245                 250                 255

Asn Pro Thr Lys Ser Gln Arg Glu Trp Gly Leu Thr Thr Tyr Ile Glu
                260                 265                 270

Ala Leu Lys Glu Ala Ile Glu Val Leu Ser Ile Thr Gly Ser Lys
            275                 280                 285

Asp Leu Asn Leu Leu Gly Ala Cys Ser Gly Gly Ile Thr Thr Ala Thr
            290                 295                 300

Leu Val Gly His Tyr Val Ala Ser Gly Glu Lys Lys Val Asn Ala Phe
305                 310                 315                 320

Thr Gln Leu Val Ser Val Leu Asp Phe Glu Leu Asn Thr Gln Val Ala
                325                 330                 335

Leu Phe Ala Asp Glu Lys Thr Leu Glu Ala Ala Lys Arg Arg Ser Tyr
                340                 345                 350

Gln Ser Gly Val Leu Glu Gly Lys Asp Met Ala Lys Val Phe Ala Trp
                355                 360                 365

Met Arg Pro Asn Asp Leu Ile Trp Asn Tyr Trp Val Asn Asn Tyr Leu
        370                 375                 380

Leu Gly Asn Gln Pro Pro Ala Phe Asp Ile Leu Tyr Trp Asn Asn Asp
385                 390                 395                 400

Thr Thr Arg Leu Pro Ala Ala Leu His Gly Glu Phe Val Glu Leu Phe
                405                 410                 415

Lys Ser Asn Pro Leu Asn Arg Pro Gly Ala Leu Glu Val Ser Gly Thr
                420                 425                 430

Pro Ile Asp Leu Lys Gln Val Thr Cys Asp Phe Tyr Cys Val Ala Gly
```

-continued

```
                435                 440                 445
Leu Asn Asp His Ile Thr Pro Trp Glu Ser Cys Tyr Lys Ser Ala Arg
    450                 455                 460
Leu Leu Gly Gly Lys Cys Glu Phe Ile Leu Ser Asn Ser Gly His Ile
465                 470                 475                 480
Gln Ser Ile Leu Asn Pro Pro Gly Asn Pro Lys Ala Arg Phe Met Thr
                485                 490                 495
Asn Pro Glu Leu Pro Ala Glu Pro Lys Ala Trp Leu Glu Gln Ala Gly
            500                 505                 510
Lys His Ala Asp Ser Trp Trp Leu His Trp Gln Gln Trp Leu Ala Glu
        515                 520                 525
Arg Ser Gly Lys Thr Arg Lys Ala Pro Ala Ser Leu Gly Asn Lys Thr
    530                 535                 540
Tyr Pro Ala Gly Glu Ala Ala Pro Gly Thr Tyr Val His Glu Arg Ser
545                 550                 555                 560
Lys Ala Leu Gly Lys Gly Val Thr Glu Glu Gln Phe Lys Glu Thr Trp
                565                 570                 575
Thr Arg Pro Gly Ala Ala Gly Met Gly Glu Gly Thr Ser Leu Val Val
            580                 585                 590
Ala Lys Ser Arg Met
        595
```

<210> SEQ ID NO 24
<211> LENGTH: 1883
<212> TYPE: DNA
<213> ORGANISM: P. aeruginosa

<400> SEQUENCE: 24

```
ggatccccaa ttcccgatga gtcagaagaa caataacgag cttcccaagc aagccgcgga    60
aaacacgctg aacctgaatc cggtgatcgg catccggggc aaggacctgc tcacctccgc   120
gcgcatggtc ctgctccagg cggtgcgcca gccgctgcag agcgccaggc acgtggcgca   180
tttcagcctg gagctgaaga cgtcctgct  cggccagtcg gagctacgcc caggcgatga   240
cgaccgacgc ttttccgatc cggcctggag ccagaatcca ctgtacaagc gctacatgca   300
gacctacctg gcctggcgca aggagctgca cagctggatc agccacagcg acctgtcgcc   360
gcaggacatc agtcgtggcc agttcgtcat caacctgctg accgaggcga tgtcgccgac   420
caacagcctg agcaacccgg cggcggtcaa gcgcttcttc gagaccggcg gcaagagcct   480
gctggacggc ctcggccacc tggccaagga cctggtgaac aacggcggga tgccgagcca   540
ggtggacatg gacgccttcg aggtgggcaa gaacctggcc accacggagg cgccgtggt    600
gttccgcaac gacgtgctgg aactgatcca gtaccggccg atcaccgagt cggtgcacga   660
acgcccgctg ctggtggtgc gccgcagat  caacaagttc tacgtcttcg acctgtcgcc   720
ggacaagagc ctggcgcgct tctgcctgcg caacggcgtg cagaccttca tcgtcagttg   780
gcgcaacccg accaagtcgc agcgcgaatg ggcctgacc  acctatatcg aggcgctcaa   840
ggaggccatc gaggtagtcc tgtcgatcac cggcagcaag gacctcaacc tcctcggcgc   900
ctgctccggc gggatcacca ccgcgaccct ggtcggccac tacgtggcca gggcgagaa    960
gaaggtcaac gccttcaccc aactggtcag cgtgctcgac ttcgaactga ataccccaggt  1020
cgcgctgttc gccgacgaga agactctgga ggccgccaag cgtcgttcct accagtccgg  1080
cgtgctggag ggcaaggaca tggccaaggt gttcgcctgg atgcgcccca acgacctgat  1140
ctggaactac tgggtcaaca actacctgct cggcaaccag ccgccggcgt cgacatcct   1200
```

-continued

```
ctactggaac aacgacacca cgcgcctgcc cgccgcgctg cacggcgagt tcgtcgaact    1260
gttcaagagc aacccgctga accgccccgg cgccctggag gtctccggca cgcccatcga    1320
cctgaagcag gtgacttgcg acttctactg tgtcgccggt ctgaacgacc acatcacccc    1380
ctgggagtcg tgctacaagt cggccaggct gctgggtggc aagtgcgagt tcatcctctc    1440
caacagcggt cacatccaga gcatcctcaa cccaccgggc aaccccaagg cacgcttcat    1500
gaccaatccg gaactgcccg ccgagcccaa ggcctggctg aacaggccg gcaagcacgc     1560 cgactcgtgg tggttgcact ggcagcaatg gctggccgaa cgctccggca agacccgcaa    1620
ggcgcccgcc agcctgggca acaagaccta tccggccggc gaagccgcgc ccggaaccta    1680
cgtgcatgaa cgatcaaaag ctttgggcaa aggtgttacc gaggaacaat tcaaagagac    1740
ctggacgagg ccgggagctg ctggaatggg cgaagggcga agggactagc cttgtggtgg    1800
ccaagtccag aatgtaagac agacgttcat tgcggcggag cggccaaggc ggttcggcat    1860
cttcgcagaa aaacaactag ggg                                            1883
```

<210> SEQ ID NO 25
<211> LENGTH: 1929
<212> TYPE: DNA
<213> ORGANISM: P. aeruginosa
<220> FEATURE:
<221> NAME/KEY: CDS
<222> LOCATION: (1)..(1929)

<400> SEQUENCE: 25

```
atg gct tct atg ata tcc tct tcc gct gtg aca aca gtc agc cgt gcc         48
Met Ala Ser Met Ile Ser Ser Ser Ala Val Thr Thr Val Ser Arg Ala
1               5                   10                  15 tct agg ggg caa tcc gcc gca atg gct cca ttc ggc ggc ctc aaa tcc         96
Ser Arg Gly Gln Ser Ala Ala Met Ala Pro Phe Gly Gly Leu Lys Ser
                20                  25                  30 atg act gga ttc cca gtg aag aag gtc aac act gac att act tcc att        144
Met Thr Gly Phe Pro Val Lys Lys Val Asn Thr Asp Ile Thr Ser Ile
            35                  40                  45 aca agc aat ggt gga aga gta aag tgc atg cag gtg tgg cct cca att        192
Thr Ser Asn Gly Gly Arg Val Lys Cys Met Gln Val Trp Pro Pro Ile
        50                  55                  60 gga aag aag aag ttt gag act ctt tcc tat ttg cca cca ttg acc aga        240
Gly Lys Lys Lys Phe Glu Thr Leu Ser Tyr Leu Pro Pro Leu Thr Arg
65                  70                  75                  80 gat tcc cgg gtg agt cag aag aac aat aac gag ctt ccc aag caa gcc        288
Asp Ser Arg Val Ser Gln Lys Asn Asn Asn Glu Leu Pro Lys Gln Ala
                85                  90                  95 gcg gaa aac acg ctg aac ctg aat ccg gtg atc ggc atc cgg ggc aag        336
Ala Glu Asn Thr Leu Asn Leu Asn Pro Val Ile Gly Ile Arg Gly Lys
                100                 105                 110 gac ctg ctc acc tcc gcg cgc atg gtc ctg ctc cag gcg gtg cgc cag        384
Asp Leu Leu Thr Ser Ala Arg Met Val Leu Leu Gln Ala Val Arg Gln
            115                 120                 125 ccg ctg cac agc gcc agg cac gtg gcg cat ttc agc ctg gag ctg aag        432
Pro Leu His Ser Ala Arg His Val Ala His Phe Ser Leu Glu Leu Lys
        130                 135                 140 aac gtc ctg ctc ggc cag tcg gag cta cgc cca ggc gat gac gac cga        480
Asn Val Leu Leu Gly Gln Ser Glu Leu Arg Pro Gly Asp Asp Asp Arg
145                 150                 155                 160 cgc ttt tcc gat ccg gcc tgg agc cag aat cca ctg tac aag cgc tac        528
Arg Phe Ser Asp Pro Ala Trp Ser Gln Asn Pro Leu Tyr Lys Arg Tyr
                165                 170                 175
```

| | | |
|---|---|---|
| atg cag acc tac ctg gcc tgg cgc aag gag ctg cac agc tgg atc agc<br>Met Gln Thr Tyr Leu Ala Trp Arg Lys Glu Leu His Ser Trp Ile Ser<br>180 185 190 | | 576 |
| cac agc gac ctg tcg ccg cag gac atc agt cgt ggc cag ttc gtc atc<br>His Ser Asp Leu Ser Pro Gln Asp Ile Ser Arg Gly Gln Phe Val Ile<br>195 200 205 | | 624 |
| aac ctg ctg acc gag gcg atg tcg ccg acc aac agc ctg agc aac ccg<br>Asn Leu Leu Thr Glu Ala Met Ser Pro Thr Asn Ser Leu Ser Asn Pro<br>210 215 220 | | 672 |
| gcg gcg gtc aag cgc ttc ttc gag acc ggc ggc aag agc ctg ctg gac<br>Ala Ala Val Lys Arg Phe Phe Glu Thr Gly Gly Lys Ser Leu Leu Asp<br>225 230 235 240 | | 720 |
| ggc ctc ggc cac ctg gcc aag gac ctg gtg aac aac ggc ggg atg ccg<br>Gly Leu Gly His Leu Ala Lys Asp Leu Val Asn Asn Gly Gly Met Pro<br>245 250 255 | | 768 |
| agc cag gtg gac atg gac gcc ttc gag gtg ggc aag aac ctg gcc acc<br>Ser Gln Val Asp Met Asp Ala Phe Glu Val Gly Lys Asn Leu Ala Thr<br>260 265 270 | | 816 |
| acc gag ggc gcc gtg gtg ttc cgc aac gac gtg ctg gaa ctg atc cag<br>Thr Glu Gly Ala Val Val Phe Arg Asn Asp Val Leu Glu Leu Ile Gln<br>275 280 285 | | 864 |
| tac cgg ccg atc acc gag tcg gtg cac gaa cgc ccg ctg ctg gtg gtg<br>Tyr Arg Pro Ile Thr Glu Ser Val His Glu Arg Pro Leu Leu Val Val<br>290 295 300 | | 912 |
| ccg ccg cag atc aac aag ttc tac gtc ttc gac ctg tcg ccg gac aag<br>Pro Pro Gln Ile Asn Lys Phe Tyr Val Phe Asp Leu Ser Pro Asp Lys<br>305 310 315 320 | | 960 |
| agc ctg gcg cgc ttc tgc ctg cgc aac ggc gtg cag acc ttc atc gtc<br>Ser Leu Ala Arg Phe Cys Leu Arg Asn Gly Val Gln Thr Phe Ile Val<br>325 330 335 | | 1008 |
| agt tgg cgc aac ccg acc aag tcg cag cgc gaa tgg ggc ctg acc acc<br>Ser Trp Arg Asn Pro Thr Lys Ser Gln Arg Glu Trp Gly Leu Thr Thr<br>340 345 350 | | 1056 |
| tat atc gag gcg ctc aag gag gcc atc gag gta gtc ctg tcg atc acc<br>Tyr Ile Glu Ala Leu Lys Glu Ala Ile Glu Val Val Leu Ser Ile Thr<br>355 360 365 | | 1104 |
| ggc agc aag gac ctc aac ctc ctc ggc gcc tgc tcc ggc ggg atc acc<br>Gly Ser Lys Asp Leu Asn Leu Leu Gly Ala Cys Ser Gly Gly Ile Thr<br>370 375 380 | | 1152 |
| acc gcg acc ctg gtc ggc cac tac gtg gcc agc ggc gag aag aag gtc<br>Thr Ala Thr Leu Val Gly His Tyr Val Ala Ser Gly Glu Lys Lys Val<br>385 390 395 400 | | 1200 |
| aac gcc ttc acc caa ctg gtc agc gtg ctc gac ttc gaa ctg aat acc<br>Asn Ala Phe Thr Gln Leu Val Ser Val Leu Asp Phe Glu Leu Asn Thr<br>405 410 415 | | 1248 |
| cag gtc gcg ctg ttc gcc gac gag aag act ctg gag gcc gcc aag cgt<br>Gln Val Ala Leu Phe Ala Asp Glu Lys Thr Leu Glu Ala Ala Lys Arg<br>420 425 430 | | 1296 |
| cgt tcc tac cag tcc ggc gtg ctg gag ggc aag gac atg gcc aag gtg<br>Arg Ser Tyr Gln Ser Gly Val Leu Glu Gly Lys Asp Met Ala Lys Val<br>435 440 445 | | 1344 |
| ttc gcc tgg atg cgc ccc aac gac ctg atc tgg aac tac tgg gtc aac<br>Phe Ala Trp Met Arg Pro Asn Asp Leu Ile Trp Asn Tyr Trp Val Asn<br>450 455 460 | | 1392 |
| aac tac ctg ctc ggc aac cag ccg ccg gcg ttc gac atc ctc tac tgg<br>Asn Tyr Leu Leu Gly Asn Gln Pro Pro Ala Phe Asp Ile Leu Tyr Trp<br>465 470 475 480 | | 1440 |
| aac aac gac acc acg cgc ctg ccc gcc gcg ctg cac ggc gag ttc gtc<br>Asn Asn Asp Thr Thr Arg Leu Pro Ala Ala Leu His Gly Glu Phe Val | | 1488 |

```
                        485                 490                 495
gaa ctg ttc aag agc aac ccg ctg aac cgc ccc ggc gcc ctg gag gtc      1536
Glu Leu Phe Lys Ser Asn Pro Leu Asn Arg Pro Gly Ala Leu Glu Val
            500                 505                 510 tcc ggc acg ccc atc gac ctg aag cag gtg act tgc gac ttc tac tgt      1584
Ser Gly Thr Pro Ile Asp Leu Lys Gln Val Thr Cys Asp Phe Tyr Cys
        515                 520                 525 gtc gcc ggt ctg aac gac cac atc acc ccc tgg gag tcg tgc tac aag      1632
Val Ala Gly Leu Asn Asp His Ile Thr Pro Trp Glu Ser Cys Tyr Lys
    530                 535                 540 tcg gcc agg ctg ctg ggt ggc aag tgc gag ttc atc ctc tcc aac agc      1680
Ser Ala Arg Leu Leu Gly Gly Lys Cys Glu Phe Ile Leu Ser Asn Ser
545                 550                 555                 560 ggt cac atc cag agc atc ctc aac cca ccg ggc aac ccc aag gca cgc      1728
Gly His Ile Gln Ser Ile Leu Asn Pro Pro Gly Asn Pro Lys Ala Arg
            565                 570                 575 ttc atg acc aat ccg gaa ctg ccc gcc gag ccc aag gcc tgg ctg gaa      1776
Phe Met Thr Asn Pro Glu Leu Pro Ala Glu Pro Lys Ala Trp Leu Glu
        580                 585                 590 cag gcc ggc aag cac gcc gac tcg tgg tgg ttg cac tgg cag caa tgg      1824
Gln Ala Gly Lys His Ala Asp Ser Trp Trp Leu His Trp Gln Gln Trp
    595                 600                 605 ctg gcc gaa cgc tcc ggc aag acc cgc aag gcg ccc gcc agc ctg ggc      1872
Leu Ala Glu Arg Ser Gly Lys Thr Arg Lys Ala Pro Ala Ser Leu Gly
610                 615                 620 aac aag acc tat ccg gcc ggc gaa gcc gcg ccc gga acc tac gtg cat      1920
Asn Lys Thr Tyr Pro Ala Gly Glu Ala Ala Pro Gly Thr Tyr Val His
625                 630                 635                 640 gaa cga tga                                                          1929
Glu Arg <210> SEQ ID NO 26
<211> LENGTH: 642
<212> TYPE: PRT
<213> ORGANISM: P. aeruginosa

<400> SEQUENCE: 26

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Ser Arg Val Ser Gln Lys Asn Asn Glu Leu Pro Lys Gln Ala
                85                  90                  95

Ala Glu Asn Thr Leu Asn Leu Asn Pro Val Ile Gly Ile Arg Gly Lys
            100                 105                 110

Asp Leu Leu Thr Ser Ala Arg Met Val Leu Leu Gln Ala Val Arg Gln
        115                 120                 125

Pro Leu His Ser Ala Arg His Val Ala His Phe Ser Leu Glu Leu Lys
    130                 135                 140

Asn Val Leu Leu Gly Gln Ser Glu Leu Arg Pro Gly Asp Asp Arg
145                 150                 155                 160
```

-continued

```
Arg Phe Ser Asp Pro Ala Trp Ser Gln Asn Pro Leu Tyr Lys Arg Tyr
                165                 170                 175
Met Gln Thr Tyr Leu Ala Trp Arg Lys Glu Leu His Ser Trp Ile Ser
            180                 185                 190
His Ser Asp Leu Ser Pro Gln Asp Ile Ser Arg Gly Gln Phe Val Ile
        195                 200                 205
Asn Leu Leu Thr Glu Ala Met Ser Pro Thr Asn Ser Leu Ser Asn Pro
    210                 215                 220
Ala Ala Val Lys Arg Phe Phe Glu Thr Gly Gly Lys Ser Leu Leu Asp
225                 230                 235                 240
Gly Leu Gly His Leu Ala Lys Asp Leu Val Asn Asn Gly Gly Met Pro
                245                 250                 255
Ser Gln Val Asp Met Asp Ala Phe Glu Val Gly Lys Asn Leu Ala Thr
            260                 265                 270
Thr Glu Gly Ala Val Val Phe Arg Asn Asp Val Leu Glu Leu Ile Gln
        275                 280                 285
Tyr Arg Pro Ile Thr Glu Ser Val His Glu Arg Pro Leu Leu Val Val
    290                 295                 300
Pro Pro Gln Ile Asn Lys Phe Tyr Val Phe Asp Leu Ser Pro Asp Lys
305                 310                 315                 320
Ser Leu Ala Arg Phe Cys Leu Arg Asn Gly Val Gln Thr Phe Ile Val
                325                 330                 335
Ser Trp Arg Asn Pro Thr Lys Ser Gln Arg Glu Trp Gly Leu Thr Thr
            340                 345                 350
Tyr Ile Glu Ala Leu Lys Glu Ala Ile Glu Val Val Leu Ser Ile Thr
        355                 360                 365
Gly Ser Lys Asp Leu Asn Leu Leu Gly Ala Cys Ser Gly Gly Ile Thr
    370                 375                 380
Thr Ala Thr Leu Val Gly His Tyr Val Ala Ser Gly Glu Lys Lys Val
385                 390                 395                 400
Asn Ala Phe Thr Gln Leu Val Ser Val Leu Asp Phe Glu Leu Asn Thr
                405                 410                 415
Gln Val Ala Leu Phe Ala Asp Glu Lys Thr Leu Glu Ala Ala Lys Arg
            420                 425                 430
Arg Ser Tyr Gln Ser Gly Val Leu Glu Gly Lys Asp Met Ala Lys Val
        435                 440                 445
Phe Ala Trp Met Arg Pro Asn Asp Leu Ile Trp Asn Tyr Trp Val Asn
    450                 455                 460
Asn Tyr Leu Leu Gly Asn Gln Pro Ala Phe Asp Ile Leu Tyr Trp
465                 470                 475                 480
Asn Asn Asp Thr Thr Arg Leu Pro Ala Ala Leu His Gly Glu Phe Val
                485                 490                 495
Glu Leu Phe Lys Ser Asn Pro Leu Asn Arg Pro Gly Ala Leu Glu Val
            500                 505                 510
Ser Gly Thr Pro Ile Asp Leu Lys Gln Val Thr Cys Asp Phe Tyr Cys
        515                 520                 525
Val Ala Gly Leu Asn Asp His Ile Thr Pro Trp Glu Ser Cys Tyr Lys
    530                 535                 540
Ser Ala Arg Leu Leu Gly Gly Lys Cys Glu Phe Ile Leu Ser Asn Ser
545                 550                 555                 560
Gly His Ile Gln Ser Ile Leu Asn Pro Pro Gly Asn Pro Lys Ala Arg
                565                 570                 575
Phe Met Thr Asn Pro Glu Leu Pro Ala Glu Pro Lys Ala Trp Leu Glu
```

```
                          580                     585                     590
           Gln Ala Gly Lys His Ala Asp Ser Trp Trp Leu His Trp Gln Gln Trp
                 595                     600                     605

Leu Ala Glu Arg Ser Gly Lys Thr Arg Lys Ala Pro Ala Ser Leu Gly
                 610                     615                     620

Asn Lys Thr Tyr Pro Ala Gly Glu Ala Ala Pro Gly Thr Tyr Val His
           625                     630                     635                     640

Glu Arg

<210> SEQ ID NO 27
           <211> LENGTH: 1941
           <212> TYPE: DNA
           <213> ORGANISM: P. aeruginosa

<400> SEQUENCE: 27
ggatccatgg cttctatgat atcctcttcc gctgtgacaa cagtcagccg tgcctctagg       60
gggcaatccg ccgcaatggc tccattcggc ggcctcaaat ccatgactgg attcccagtg      120
aagaaggtca acactgacat tacttccatt acaagcaatg gtggaagagt aaagtgcatg      180
caggtgtggc ctccaattgg aaagaagaag tttgagactc tttcctattt gccaccattg      240
accagagatt cccgggtgag tcagaagaac aataacgagc ttcccaagca agccgcggaa      300
aacacgctga acctgaatcc ggtgatcggc atccggggca aggacctgct cacctccgcg      360
cgcatggtcc tgctccaggc ggtgcgccac ccgctgcaca cgccaggca cgtggcgcat       420 ttcagcctgg agctgaagaa cgtcctgctc ggccagtcgg agctacgccc aggcgatgac      480
gaccgacgct tttccgatcc ggcctggagc cagaatccac tgtacaagcg ctacatgcag      540
acctacctgg cctggcgcaa ggagctgcac agctggatca ccacagcga cctgtcgccg       600 caggacatca gtcgtggcca gttcgtcatc aacctgctga ccgaggcgat gtcgccgacc      660
aacagcctga gcaacccggc ggcggtcaag cgcttcttcg agaccggcgg caagagcctg      720
ctggacggcc tcggccacct ggccaaggac ctggtgaaca acggcgggat gccgagccag      780
gtggacatgg acgccttcga ggtgggcaag aacctggcca ccaccgaggg cgccgtggtg      840
ttccgcaacg acgtgctgga actgatccag taccggccga tcaccgagtc ggtgcacgaa      900
cgcccgctgc tggtggtgcc gccgcagatc aacaagttct acgtcttcga cctgtcgccg      960
gacaagagcc tggcgcgctt ctgcctgcgc aacggcgtgc agaccttcat cgtcagttgg     1020
cgcaacccga ccaagtcgca gcgcgaatgg ggcctgacca cctatatcga ggcgctcaag     1080
gaggccatcg aggtagtcct gtcgatcacc ggcagcaagg acctcaacct cctcggcgcc     1140
tgctccggcg ggatcaccac cgcgaccctg tcggccact  cgtggccag cggcgagaag     1200 aaggtcaacg ccttcaccca actggtcagc gtgctcgact tcgaactgaa tacccaggtc     1260
gcgctgttcg ccgacgagaa gactctggag gccgccaagc gtcgttccta ccagtccggc     1320
gtgctggagg gcaaggacat ggccaaggtg ttcgcctgga tgcgccccaa cgacctgatc     1380
tggaactact gggtcaacaa ctacctgctc ggcaaccagc cgccggcgtt cgacatcctc     1440
tactggaaca acgacaccac gcgcctgccc gccgcgctgc acggcgagtt cgtcgaactg     1500
ttcaagagca cccgctgaa ccgcccggc gccctggagg tctccggcac gcccatcgac       1560
ctgaagcagg tgacttgcga cttctactgt gtcgccggtc tgaacgacca catcacccc       1620 tgggagtcgt gctacaagtc ggccaggctg ctggtggca agtgcgagtt catcctctcc      1680
aacagcggtc acatccagag catcctcaac ccaccgggca accccaaggc acgcttcatg     1740
```

-continued

```
accaatccgg aactgcccgc cgagcccaag gcctggctgg aacaggccgg caagcacgcc      1800
gactcgtggt ggttgcactg gcagcaatgg ctggccgaac gctccggcaa gacccgcaag      1860
gcgcccgcca gcctgggcaa caagacctat ccggccggcg aagccgcgcc cggaacctac      1920
gtgcatgaac gatgaggtac c                                                1941

<210> SEQ ID NO 28
<211> LENGTH: 1137
<212> TYPE: DNA
<213> ORGANISM: Pseudomonas putida
<220> FEATURE:
<221> NAME/KEY: CDS
<222> LOCATION: (1)..(1137)

<400> SEQUENCE: 28 atg gct tct atg ata tcc tct tcc gct gtg aca aca gtc agc cgt gcc        48
Met Ala Ser Met Ile Ser Ser Ser Ala Val Thr Thr Val Ser Arg Ala
1               5                  10                  15 tct agg ggg caa tcc gcc gca atg gct cca ttc ggc ggc ctc aaa tcc        96
Ser Arg Gly Gln Ser Ala Ala Met Ala Pro Phe Gly Gly Leu Lys Ser
                20                  25                  30 atg act gga ttc cca gtg aag aag gtc aac act gac att act tcc att       144
Met Thr Gly Phe Pro Val Lys Lys Val Asn Thr Asp Ile Thr Ser Ile
            35                  40                  45 aca agc aat ggt gga aga gta aag tgc atg cag gtg tgg cct cca att       192
Thr Ser Asn Gly Gly Arg Val Lys Cys Met Gln Val Trp Pro Pro Ile
        50                  55                  60 gga aag aag aag ttt gag act ctt tcc tat ttg cca cca ttg acc aga       240
Gly Lys Lys Lys Phe Glu Thr Leu Ser Tyr Leu Pro Pro Leu Thr Arg
65                  70                  75                  80 gat tcc cgg gtg agg cca gaa atc gct gta ctt gat atc caa ggt cag       288
Asp Ser Arg Val Arg Pro Glu Ile Ala Val Leu Asp Ile Gln Gly Gln
                85                  90                  95 tat cgg gtt tac acg gag ttc tat cgc gcg gat gcg gcc gaa aac acg       336
Tyr Arg Val Tyr Thr Glu Phe Tyr Arg Ala Asp Ala Ala Glu Asn Thr
                100                 105                 110 atc atc ctg atc aac ggc tcg ctg gcc acc acg gcc tcg ttc gcc cag       384
Ile Ile Leu Ile Asn Gly Ser Leu Ala Thr Thr Ala Ser Phe Ala Gln
            115                 120                 125 acg gta cgt aac ctg cac cca cag ttc aac gtg gtt ctg ttc gac cag       432
Thr Val Arg Asn Leu His Pro Gln Phe Asn Val Val Leu Phe Asp Gln
        130                 135                 140 ccg tat tca ggc aag tcc aag ccg cac aac cgt cag gaa cgg ctg atc       480
Pro Tyr Ser Gly Lys Ser Lys Pro His Asn Arg Gln Glu Arg Leu Ile
145                 150                 155                 160 agc aag gag acc gag gcg cat atc ctc ctt gag ctg atc gag cac ttc       528
Ser Lys Glu Thr Glu Ala His Ile Leu Leu Glu Leu Ile Glu His Phe
                165                 170                 175 cag gca gac cac gtg atg tct ttt tcg tgg ggt ggc gca agc acg ctg       576
Gln Ala Asp His Val Met Ser Phe Ser Trp Gly Gly Ala Ser Thr Leu
            180                 185                 190 ctg gcg ctg gcg cac cag ccg cgg tac gtg aag aag gca gtg gtg agt       624
Leu Ala Leu Ala His Gln Pro Arg Tyr Val Lys Lys Ala Val Val Ser
        195                 200                 205 tcg ttc tcg cca gtg atc aac gag ccg atg cgc gac tat ctg gac cgt       672
Ser Phe Ser Pro Val Ile Asn Glu Pro Met Arg Asp Tyr Leu Asp Arg
    210                 215                 220 ggc tgc cag tac ctg gcc gcc tgc gac cgt tat cag gtc ggc aac ctg       720
Gly Cys Gln Tyr Leu Ala Ala Cys Asp Arg Tyr Gln Val Gly Asn Leu
225                 230                 235                 240
```

-continued

```
gtc aat gac acc atc ggc aag cac ttg ccg tcg ctg ttc aaa cgc ttc      768
Val Asn Asp Thr Ile Gly Lys His Leu Pro Ser Leu Phe Lys Arg Phe
            245                 250                 255 aac tac cgc cat gtg agc agc ctg gac agc cac gag tac gca cag atg      816
Asn Tyr Arg His Val Ser Ser Leu Asp Ser His Glu Tyr Ala Gln Met
        260                 265                 270 cac ttc cac atc aac cag gtg ctg gag cac gac ctg gaa cgt gcg ctg      864
His Phe His Ile Asn Gln Val Leu Glu His Asp Leu Glu Arg Ala Leu
    275                 280                 285 caa ggc gcg cgc aat atc aac atc ccg gtg ctg ttc atc aac ggc gag      912
Gln Gly Ala Arg Asn Ile Asn Ile Pro Val Leu Phe Ile Asn Gly Glu
290                 295                 300 cgc gac gag tac acc aca gtc gag gat gcg cgg cag ttc agc aag cat      960
Arg Asp Glu Tyr Thr Thr Val Glu Asp Ala Arg Gln Phe Ser Lys His
305                 310                 315                 320 gtg ggc aga agc cag ttc agc gtg atc cgc gat gcg ggc cac ttc ctg     1008
Val Gly Arg Ser Gln Phe Ser Val Ile Arg Asp Ala Gly His Phe Leu
                325                 330                 335 gac atg gag aac aag acc gcc tgc gag aac acc cgc aat gtc atg ctg     1056
Asp Met Glu Asn Lys Thr Ala Cys Glu Asn Thr Arg Asn Val Met Leu
            340                 345                 350 ggc ttc ctc aag cca acc gtg cgt gaa ccc cgc caa cgt tac caa ccc     1104
Gly Phe Leu Lys Pro Thr Val Arg Glu Pro Arg Gln Arg Tyr Gln Pro
        355                 360                 365 gtg cag cag ggg cag cat gca ttt gcc atc tga                         1137
Val Gln Gln Gly Gln His Ala Phe Ala Ile
    370                 375
```

<210> SEQ ID NO 29
<211> LENGTH: 378
<212> TYPE: PRT
<213> ORGANISM: Pseudomonas putida

<400> SEQUENCE: 29

```
Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Ser Arg Val Arg Pro Glu Ile Ala Val Leu Asp Ile Gln Gly Gln
                85                  90                  95

Tyr Arg Val Tyr Thr Glu Phe Tyr Arg Ala Asp Ala Ala Glu Asn Thr
            100                 105                 110

Ile Ile Leu Ile Asn Gly Ser Leu Ala Thr Thr Ala Ser Phe Ala Gln
        115                 120                 125

Thr Val Arg Asn Leu His Pro Gln Phe Asn Val Val Leu Phe Asp Gln
    130                 135                 140

Pro Tyr Ser Gly Lys Ser Lys Pro His Asn Arg Gln Glu Arg Leu Ile
145                 150                 155                 160

Ser Lys Glu Thr Glu Ala His Ile Leu Leu Glu Leu Ile Glu His Phe
                165                 170                 175

Gln Ala Asp His Val Met Ser Phe Ser Trp Gly Gly Ala Ser Thr Leu
            180                 185                 190
```

-continued

```
Leu Ala Leu Ala His Gln Pro Arg Tyr Val Lys Lys Ala Val Val Ser
            195                 200                 205
Ser Phe Ser Pro Val Ile Asn Glu Pro Met Arg Asp Tyr Leu Asp Arg
        210                 215                 220
Gly Cys Gln Tyr Leu Ala Ala Cys Asp Arg Tyr Gln Val Gly Asn Leu
225                 230                 235                 240
Val Asn Asp Thr Ile Gly Lys His Leu Pro Ser Leu Phe Lys Arg Phe
                245                 250                 255
Asn Tyr Arg His Val Ser Ser Leu Asp Ser His Glu Tyr Ala Gln Met
            260                 265                 270
His Phe His Ile Asn Gln Val Leu Glu His Asp Leu Glu Arg Ala Leu
        275                 280                 285
Gln Gly Ala Arg Asn Ile Asn Ile Pro Val Leu Phe Ile Asn Gly Glu
    290                 295                 300
Arg Asp Glu Tyr Thr Thr Val Glu Asp Ala Arg Gln Phe Ser Lys His
305                 310                 315                 320
Val Gly Arg Ser Gln Phe Ser Val Ile Arg Asp Ala Gly His Phe Leu
                325                 330                 335
Asp Met Glu Asn Lys Thr Ala Cys Glu Asn Thr Arg Asn Val Met Leu
            340                 345                 350
Gly Phe Leu Lys Pro Thr Val Arg Glu Pro Arg Gln Arg Tyr Gln Pro
        355                 360                 365
Val Gln Gln Gly Gln His Ala Phe Ala Ile
    370                 375

<210> SEQ ID NO 30
<211> LENGTH: 1149
<212> TYPE: DNA
<213> ORGANISM: Pseudomonas putida

<400> SEQUENCE: 30
ggatccatgg cttctatgat atcctcttcc gctgtgacaa cagtcagccg tgcctctagg      60
gggcaatccg ccgcaatggc tccattcggc ggcctcaaat ccatgactgg attcccagtg     120
aagaaggtca acactgacat tacttccatt acaagcaatg gtggaagagt aaagtgcatg     180
caggtgtggc ctccaattgg aaagaagaag tttgagactc tttcctattt gccaccattg     240
accagagatt cccgggtgag gccagaaatc gctgtacttg atatccaagg tcagtatcgg     300
gtttacacgg agttctatcg cgcggatgcg ccgaaaaaca cgatcatcct gatcaacggc     360
tcgctggcca ccacggcctc gttcgcccag acggtacgta acctgcaccc acagttcaac     420
gtggttctgt cgaccagcc gtattcaggc aagtccaagc cgcacaaccg tcaggaacgg     480
ctgatcagca aggagaccga ggcgcatatc ctccttgagc tgatcgagca cttccaggca     540
gaccacgtga tgtcttttc gtggggtggc caagcacgc tgctggcgct ggcgcaccag     600
ccgcggtacg tgaagaaggc agtggtgagt tcgttctcgc cagtgatcaa cgagccgatg     660
cgcgactatc tggaccgtgg ctgccagtac ctggccgcct cgaccgtta tcaggtcggc     720
aacctggtca atgacaccat cggcaagcac ttgccgtcgc tgttcaaacg cttcaactac     780
cgccatgtga gcagcctgga cagccacgag tacgcacaga tgcacttcca tcaaccag     840
gtgctggagc acgacctgga acgtgcgctg caaggcgcgc gcaatatcaa catcccggtg     900
ctgttcatca cggcgagcg cgacgagtac accacagtcg aggatgcgcg gcagttcagc     960
aagcatgtgg gcagaagcca gttcagcgtg atccgcgatg cgggccactt cctggacatg    1020
```

```
gagaacaaga ccgcctgcga gaacacccgc aatgtcatgc tgggcttcct caagccaacc    1080
gtgcgtgaac cccgccaacg ttaccaaccc gtgcagcagg gcagcatgc atttgccatc    1140 tgaggtacc                                                             1149

<210> SEQ ID NO 31
<211> LENGTH: 519
<212> TYPE: DNA
<213> ORGANISM: Aeromonas caviae
<220> FEATURE:
<221> NAME/KEY: CDS
<222> LOCATION: (1)..(519)

<400> SEQUENCE: 31 atg agc gca caa tcc ctg gaa gta ggc cag aag gcc cgt ctc agc aag    48
Met Ser Ala Gln Ser Leu Glu Val Gly Gln Lys Ala Arg Leu Ser Lys
1               5                   10                  15 cgg ttc ggg gcg gcg gag gta gcc gcc ttc gcc gcg ctc tcg gag gac    96
Arg Phe Gly Ala Ala Glu Val Ala Ala Phe Ala Ala Leu Ser Glu Asp
                20                  25                  30 ttc aac ccc ctg cac ctg gac ccg gcc ttc gcc gcc acg acg gcg ttc    144
Phe Asn Pro Leu His Leu Asp Pro Ala Phe Ala Ala Thr Thr Ala Phe
            35                  40                  45 gag cgg ccc ata gtc cac ggc atg ctg ctc gcc agc ctc ttc tcc ggg    192
Glu Arg Pro Ile Val His Gly Met Leu Leu Ala Ser Leu Phe Ser Gly
        50                  55                  60 ctg ctg ggc cag cag ttg ccg ggc aag ggg agc atc tat ctg ggt caa    240
Leu Leu Gly Gln Gln Leu Pro Gly Lys Gly Ser Ile Tyr Leu Gly Gln
65                  70                  75                  80 agc ctc agc ttc aag ctg ccg gtc ttt gtc ggg gac gag gtg acg gcc    288
Ser Leu Ser Phe Lys Leu Pro Val Phe Val Gly Asp Glu Val Thr Ala
                85                  90                  95 gag gtg gag gtg acc gcc ctt cgc gag gac aag ccc atc gcc acc ctg    336
Glu Val Glu Val Thr Ala Leu Arg Glu Asp Lys Pro Ile Ala Thr Leu
                100                 105                 110 acc acc cgc atc ttc acc caa ggc ggc gcc ctc gcc gtg acg ggg gaa    384
Thr Thr Arg Ile Phe Thr Gln Gly Gly Ala Leu Ala Val Thr Gly Glu
            115                 120                 125 gcc gtg gtc aag ctg cct tca aaa gct ttg ggc aaa ggt gtt acc gag    432
Ala Val Val Lys Leu Pro Ser Lys Ala Leu Gly Lys Gly Val Thr Glu
        130                 135                 140 gaa caa ttc aaa gag acc tgg acg agg ccg gga gct gct gga atg ggc    480
Glu Gln Phe Lys Glu Thr Trp Thr Arg Pro Gly Ala Ala Gly Met Gly
145                 150                 155                 160 gaa ggg act agc ctt gtg gtg gcc aag tcc aga atg taa                 519
Glu Gly Thr Ser Leu Val Val Ala Lys Ser Arg Met
                165                 170

<210> SEQ ID NO 32
<211> LENGTH: 172
<212> TYPE: PRT
<213> ORGANISM: Aeromonas caviae

<400> SEQUENCE: 32

Met Ser Ala Gln Ser Leu Glu Val Gly Gln Lys Ala Arg Leu Ser Lys
1               5                   10                  15

Arg Phe Gly Ala Ala Glu Val Ala Ala Phe Ala Ala Leu Ser Glu Asp
                20                  25                  30

Phe Asn Pro Leu His Leu Asp Pro Ala Phe Ala Ala Thr Thr Ala Phe
            35                  40                  45

Glu Arg Pro Ile Val His Gly Met Leu Leu Ala Ser Leu Phe Ser Gly
```

```
                50                  55                  60
Leu Leu Gly Gln Gln Leu Pro Gly Lys Gly Ser Ile Tyr Leu Gly Gln
 65                  70                  75                  80

Ser Leu Ser Phe Lys Leu Pro Val Phe Val Gly Asp Glu Val Thr Ala
                 85                  90                  95

Glu Val Glu Val Thr Ala Leu Arg Glu Asp Lys Pro Ile Ala Thr Leu
                100                 105                 110

Thr Thr Arg Ile Phe Thr Gln Gly Gly Ala Leu Ala Val Thr Gly Glu
            115                 120                 125

Ala Val Val Lys Leu Pro Ser Lys Ala Leu Gly Lys Gly Val Thr Glu
        130                 135                 140

Glu Gln Phe Lys Glu Thr Trp Thr Arg Pro Gly Ala Ala Gly Met Gly
145                 150                 155                 160

Glu Gly Thr Ser Leu Val Val Ala Lys Ser Arg Met
                165                 170

<210> SEQ ID NO 33
<211> LENGTH: 598
<212> TYPE: DNA
<213> ORGANISM: Aeromonas caviae

<400> SEQUENCE: 33
ggatccatga gcgcacaatc cctggaagta ggccagaagg cccgtctcag caagcggttc      60
ggggcggcgg aggtagccgc cttcgccgcg ctctcggagg acttcaaccc cctgcacctg     120
gacccggcct tcgccgccac cacggcgttc gagcggccca tagtccacgg catgctgctc     180
gccagcctct tctccgggct gctgggccag cagttgccgg gcaaggggag catctatctg     240
ggtcaaagcc tcagcttcaa gctgccggtc tttgtcgggg acgaggtgac ggccgaggtg     300
gaggtgaccg cccttcgcga ggacaagccc atcgccaccc tgaccacccg catcttcacc     360
caaggcggcg ccctcgccgt gacgggggaa gccgtggtca agctgccttc aaaagctttg     420
ggcaaaggtg ttaccgagga acaattcaaa gagacctgga cgaggccggg agctgctgga     480
atgggcgaag gcgaaggga ctagccttgt ggtggccaag tccagaatgt aagacagacg     540
ttcattgcgg cggagcggcc aaggcggttc ggcatcttcg cagaaaaaca actagggg     598

<210> SEQ ID NO 34
<211> LENGTH: 31
<212> TYPE: DNA
<213> ORGANISM: Artificial Sequence
<220> FEATURE:
<223> OTHER INFORMATION: PCR primer TphaF
<220> FEATURE:
<221> NAME/KEY: misc_feature
<222> LOCATION: 1, 2, 3, 4, 5, 6
<223> OTHER INFORMATION: n = A,T,C or G

<400> SEQUENCE: 34
nnnnnnggat ccatggcttc tatgatatcc t                                     31

<210> SEQ ID NO 35
<211> LENGTH: 30
<212> TYPE: DNA
<213> ORGANISM: Artificial Sequence
<220> FEATURE:
<223> OTHER INFORMATION: PCR primer PhaF
<220> FEATURE:
<221> NAME/KEY: misc_feature
<222> LOCATION: 1, 2, 3, 4, 5, 6
<223> OTHER INFORMATION: n = A,T,C or G
```

```
<400> SEQUENCE: 35
nnnnnnggat ccatgactga cgttgtcatc                                          30

<210> SEQ ID NO 36
<211> LENGTH: 30
<212> TYPE: DNA
<213> ORGANISM: Artificial Sequence
<220> FEATURE:
<223> OTHER INFORMATION: PCR primer PhbF
<220> FEATURE:
<221> NAME/KEY: misc_feature
<222> LOCATION: 1, 2, 3, 4, 5, 6
<223> OTHER INFORMATION: n = A,T,C or G

<400> SEQUENCE: 36
nnnnnnggat ccatgactca gcgcattgcg                                          30

<210> SEQ ID NO 37
<211> LENGTH: 30
<212> TYPE: DNA
<213> ORGANISM: Artificial Sequence
<220> FEATURE:
<223> OTHER INFORMATION: PCR primer PhcF
<220> FEATURE:
<221> NAME/KEY: misc_feature
<222> LOCATION: 1, 2, 3, 4, 5, 6
<223> OTHER INFORMATION: n = A,T,C or G

<400> SEQUENCE: 37
nnnnnnggat ccatggcgac cggcaaaggc                                          30

<210> SEQ ID NO 38
<211> LENGTH: 18
<212> TYPE: DNA
<213> ORGANISM: Artificial Sequence
<220> FEATURE:
<223> OTHER INFORMATION: PCR primer PhaR

<400> SEQUENCE: 38
ctgagtcatg tccactcc                                                       18

<210> SEQ ID NO 39
<211> LENGTH: 18
<212> TYPE: DNA
<213> ORGANISM: Artificial Sequence
<220> FEATURE:
<223> OTHER INFORMATION: PCR primer PhbR

<400> SEQUENCE: 39
ctgccgactg gtggaacc                                                       18

<210> SEQ ID NO 40
<211> LENGTH: 18
<212> TYPE: DNA
<213> ORGANISM: Artificial Sequence
<220> FEATURE:
<223> OTHER INFORMATION: PCR primer PhcR

<400> SEQUENCE: 40
gaagcgtcat gccttggc                                                       18

<210> SEQ ID NO 41
<211> LENGTH: 27
<212> TYPE: DNA
<213> ORGANISM: Artificial Sequence
<220> FEATURE:
<223> OTHER INFORMATION: PCR primer PhaC1Cf
```

```
<220> FEATURE:
<221> NAME/KEY: misc_feature
<222> LOCATION: 1, 2, 3, 4, 5, 6
<223> OTHER INFORMATION: n = A,T,C or G

<400> SEQUENCE: 41
nnnnnnggat ccatgagcca gaagaac                                        27

<210> SEQ ID NO 42
<211> LENGTH: 28
<212> TYPE: DNA
<213> ORGANISM: Artificial Sequence
<220> FEATURE:
<223> OTHER INFORMATION: PCR primer PhaC1Cr
<220> FEATURE:
<221> NAME/KEY: misc_feature
<222> LOCATION: 1, 2, 3, 4, 5, 6
<223> OTHER INFORMATION: n = A,T,C or G

<400> SEQUENCE: 42
nnnnnnggta cctcatcgtt catgcacg                                       28

<210> SEQ ID NO 43
<211> LENGTH: 32
<212> TYPE: DNA
<213> ORGANISM: Artificial Sequence
<220> FEATURE:
<223> OTHER INFORMATION: PCR primer PhaC1Pf
<220> FEATURE:
<221> NAME/KEY: misc_feature
<222> LOCATION: 1, 2, 3, 4, 5, 6
<223> OTHER INFORMATION: n = A,T,C or G

<400> SEQUENCE: 43
nnnnnncccg ggtgagccag aagaacaata ac                                  32

<210> SEQ ID NO 44
<211> LENGTH: 25
<212> TYPE: DNA
<213> ORGANISM: Artificial Sequence
<220> FEATURE:
<223> OTHER INFORMATION: PCR primer PhaJF

<400> SEQUENCE: 44
ggatccatga gcgcacaatc cctgg                                          25

<210> SEQ ID NO 45
<211> LENGTH: 27
<212> TYPE: DNA
<213> ORGANISM: Artificial Sequence
<220> FEATURE:
<223> OTHER INFORMATION: PCR primer PhaJR

<400> SEQUENCE: 45
aagcttttga aggcagcttg accacgg                                        27

<210> SEQ ID NO 46
<211> LENGTH: 27
<212> TYPE: DNA
<213> ORGANISM: Artificial Sequence
<220> FEATURE:
<223> OTHER INFORMATION: PCR primer PhaGF

<400> SEQUENCE: 46
cccgggtgag gccagaaatc gctgtac                                        27

<210> SEQ ID NO 47
```

```
<211> LENGTH: 25
<212> TYPE: DNA
<213> ORGANISM: Artificial Sequence
<220> FEATURE:
<223> OTHER INFORMATION: PCR primer PhaGR

<400> SEQUENCE: 47
ggtacctcag atggcaaatg catgc                                            25

<210> SEQ ID NO 48
<211> LENGTH: 36
<212> TYPE: DNA
<213> ORGANISM: Artificial Sequence
<220> FEATURE:
<223> OTHER INFORMATION: PCR primer SSP-F
<220> FEATURE:
<221> NAME/KEY: misc_feature
<222> LOCATION: 1, 2
<223> OTHER INFORMATION: n = A,T,C or G

<400> SEQUENCE: 48
nngagctcga tgggaggtgc tcgaagacat attacc                                36

<210> SEQ ID NO 49
<211> LENGTH: 26
<212> TYPE: DNA
<213> ORGANISM: Artificial Sequence
<220> FEATURE:
<223> OTHER INFORMATION: PCR primer SSP-R
<220> FEATURE:
<221> NAME/KEY: misc_feature
<222> LOCATION: 1, 2
<223> OTHER INFORMATION: n = A,T,C or G

<400> SEQUENCE: 49
nnggatcctg tactagatat ggcagc                                           26

<210> SEQ ID NO 50
<211> LENGTH: 38
<212> TYPE: DNA
<213> ORGANISM: Artificial Sequence
<220> FEATURE:
<223> OTHER INFORMATION: PCR primer 3

<400> SEQUENCE: 50
ctactcattt actagtcacc atggcgccca ccgtgatg                              38

<210> SEQ ID NO 51
<211> LENGTH: 35
<212> TYPE: DNA
<213> ORGANISM: Artificial Sequence
<220> FEATURE:
<223> OTHER INFORMATION: PCR primer 4

<400> SEQUENCE: 51
catcttactg gtacctttag tacaacggtg acgcc                                 35

<210> SEQ ID NO 52
<211> LENGTH: 39
<212> TYPE: DNA
<213> ORGANISM: Artificial Sequence
<220> FEATURE:
<223> OTHER INFORMATION: PCR primer 5

<400> SEQUENCE: 52
ctactcattt actagtcacc atgagcacat acgaaggtc                             39
```

```
<210> SEQ ID NO 53
<211> LENGTH: 36
<212> TYPE: DNA
<213> ORGANISM: Artificial Sequence
<220> FEATURE:
<223> OTHER INFORMATION: PCR primer 6

<400> SEQUENCE: 53
catcttactg gtaccttcag cgtttatacg cttgca                              36

<210> SEQ ID NO 54
<211> LENGTH: 27
<212> TYPE: DNA
<213> ORGANISM: Artificial Sequence
<220> FEATURE:
<223> OTHER INFORMATION: PCR primer 1

<400> SEQUENCE: 54
ctactcataa ccatggcgcc caccgtg                                        27

<210> SEQ ID NO 55
<211> LENGTH: 43
<212> TYPE: DNA
<213> ORGANISM: Artificial Sequence
<220> FEATURE:
<223> OTHER INFORMATION: PCR primer 2

<400> SEQUENCE: 55
catcttactc atatgccgca cctgcatgca ccggatcctt ccg                      43

<210> SEQ ID NO 56
<211> LENGTH: 5
<212> TYPE: PRT
<213> ORGANISM: Artificial Sequence
<220> FEATURE:
<223> OTHER INFORMATION: Five extra N-terminal amino acid residues in a
      CPL variant

<400> SEQUENCE: 56

Met Gln Val Arg His
 1               5
```

TRANSGENIC PLANTS USED AS A BIOREACTOR SYSTEM

BACKGROUND OF THE INVENTION

Field of the Invention

The present invention relates generally to the use of plants as bioreactors for the production of molecules having useful properties such as inter alia polymers, metabolites, proteins, pharmaceuticals and nutraceuticals. More particularly, the present invention contemplates the use of grasses, and even more particularly C4 grasses, such as sugarcane, for the production of a range of compounds such as, for example, polyhydroxyalkanoates, pHBA, vanillin, indigo, adipic acid, 2-phenylethanol, 1,3-propanediol, sorbitol, fructan polymers and lactic acid as well as other products including, inter alia, other plastics, silks, carbohydrates, therapeutic and nutraceutic proteins and antibodies. The present invention further extends to transgenic plants and, in particular, transgenic C4 grass plants, capable of producing the compounds noted above and other products, and to methods for generating such plants. The ability to utilize the high growth rate and efficient carbon fixation of C4 grasses is advantageous, in that it obviates the significant growth penalties observed in other plants, and results in high yields of desired product without necessarily causing concomitant deleterious effects on individual plants. In addition, the C4 grass, sugarcane, is particularly advantageous, as in addition to the features common to all C4 grasses, this plant accumulates sucrose. This sucrose store provides a ready supply of carbon based compounds and energy which may further obviate any deleterious effects on the growth of the plant associated with the production of the product. The present invention provides, therefore, a bioreactor system comprising a genetically modified plant designed to produce particular metabolic or biosynthetic products of interest.

DESCRIPTION OF THE PRIOR ART

Reference to any prior art in this specification is not, and should not be taken as, an acknowledgment or any form of suggestion that this prior art forms part of the common general knowledge in any country.

Modern techniques of biotechnology are driving a new revolution that promises both scientific and financial gains for a range of industries. One difficulty, however, is the large financial cost of establishing sufficient infrastructure to generate recombinant products or to generate the products resulting from recombinant processes. Alternative, more cost effective systems are required to assist the generation of large amounts of product resulting from recombinant processes.

For agricultural industries, the generation of genetically engineered plants enables plants to be quickly developed with desired traits such as resistance to pathogen infestation. However, plants can also be used to produce a wide range of compounds not normally produced within the plant, thereby providing a source of renewable raw materials for the manufacturing, energy and pharmaceutical industries.

This endeavour is aided by the fact that plants, animals, insects, bacteria, fungi and even viruses have evolved in a wide range of different habitats and, hence, produce a remarkable array of compounds which allow them to survive and thrive under very varied environmental conditions. It is estimated that up to 100,000 unique compounds exist in the plant kingdom alone. In the future, genes and even entire genetic pathways may become available from different sources to assist in the manufacture of a wide range of commercial products.

Traditional chemical industries are increasingly looking towards biological systems for the production of bulk and fine chemicals. Biological processes offer numerous advantages over chemical processes, including the elimination of complicated and difficult high pressure and high temperature reactions, the use of aqueous systems rather than organic solvents, high degrees of product stereo-specificity, a capacity for highly complex synthesis and comparatively simple scale-up. The use of biological processes is not a new phenomenon, as many fine chemicals (e.g. enzymes, antibiotics) and bulk chemicals (e.g. ethanol, amino acids, citric acid, lactic acid) are produced effectively in microbial systems. Advances in molecular biology and genomics have enabled an expansion of the available product range, the transfer of production systems to microbes with desirable production traits, and significantly increased yields. Nevertheless, inherent limitations remain, in that the raw materials (e.g. molasses, sucrose, or high fructose corn syrup) and scaled up fermentation processes are relatively expensive.

By contrast, genetically modified plants should not require any more raw materials than are already required by their non-transformed counterparts and have the potential to provide a low cost of production per tonne of biomass, when compared with fermentation methods. Thus, if reasonable product yields could be achieved in plants, and if these products could be extracted at reasonable cost, the potential for chemical production in plants would be extremely high.

The polyhydroxyalkanoate (PHA), poly-(D-3-hydroxybutyrate) (PHB), is a thermoplastic with physical properties akin to polypropylene. Both PHB and polypropylene are water insoluble, exhibit good gas-barrier properties and possess similar melting points, degrees of crystallinity and glass-rubber transition temperatures (De Koning, *Can. J. Micro.* 41(1): 303-309, 1995), although PHB is more resistant to UV radiation. Moreover, unlike polypropylene, PHB is rapidly degraded by numerous bacteria and fungi under composting conditions (Jendrossek et al., *App. Micro. Biotech.* 46: 451-463, 1996; Mergaert and Swings, *Indust. Micro. Biotech.* 17: 463-469, 1996).

Cost is the major reason why PHA produced by bacterial fermentation cannot compete with conventional plastics production methodologies. Major contributors to the cost of PHA are substrate cost, energy consumption during fermentation, disposal of waste product, and the cost of constructing and maintaining plant and machinery. The use of transgenic plants for PHA production, however, has the potential to either eliminate or drastically reduce these costs since atmospheric carbon dioxide would be the substrate and energy would be derived from sunlight. Operating costs would be no more than what is incurred in ordinary agricultural practices. Waste products are the same as for a non-transgenic crop. This makes plants an attractive potential alternative to bacterial fermentation.

The production of PHB has been most closely studied in the bacterium *Ralstonia eutropha* (formerly *Alcaligenes eutrophus*), which accumulates PHB at up to 80% of its cell dry-weight (Steinbüchel and Schlegel, *Mol. Micro.* 5: 535-542, 1991). The PHB biosynthetic pathway within *R. eutropha* is well known and consists of three steps catalyzed by the three enzymes 3-ketothiolase, acetoacetyl-CoA reductase and PHB synthase, respectively. For large-scale industrial production of PHB, bacterial fermentation is economically and environmentally less favourable than the corresponding production of petrochemically derived plastics like polypropylene (Lee, *Trends Biotech.* 14: 431-438, 1996; Gemgross, *Nature Biotech.* 17: 541-544, 1999). Hence, since the glucose supplied to PHB-producing bacteria is derived from plants, it would be advantageous to be able to produce PHB in plants directly.

Attempts to achieve this goal have been unsuccessful, due largely to the significant added burden placed upon individual plants by requiring them to produce this macromolecule, resulting in a severe reduction in plant growth and infertility (Poirier et al., *Science* 256: 520-523, 1992; Bohmert et al., *Planta* 211: 841-845, 2000).

In accordance with the present invention, an efficient bioreactor system is developed in plants and in particular *Saccharum* sp. such as sugarcane.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present invention provides a plant-derived bioreactor system. Although previous attempts to effect the manufacture of useful industrial and other products in plants have not been overly successful, it has been determined in accordance with the present invention that this was due to the extra load placed on individual plants which resulted in deleterious growth effects. C4 grasses, which have particularly efficient mechanisms for the assimilation of carbon, are identified as having a high growth rate and high accumulation of biomass making them useful as bioreactors for the production of a wide range of products. Furthermore, the C4 grass, sugarcane, is particularly useful as this plant stores sugars in dimeric and/or polymeric forms. These stores may be utilized when needed such as, for example, for rapid vegetative growth, or for energy during times of significant environmental stress. The store of carbohydrate is identified in accordance with the present invention as providing a ready supply of precursor for many metabolic pathways, and utilisation of this store does not stress the producing plant. Therefore, the present invention is predicated, in part, on the identification of a subset of plants, namely the C4 grasses (particularly sugarcane), as useful bioreactors on the basis of their high carbon assimilation rate, rapid growth, high biomass production and large carbohydrate store, such as is found in the stem.

The present inventors have capitalized on the potential of a crop that has a highly efficient C4 carbon assimilation mechanism, a rapid growth rate and naturally harbours large quantities of sucrose in its stems, thereby having the ideal properties of a bioreactor. The instant inventors have developed a means to engineer this crop so as to effectively accumulate significant quantities of a product without significant decreases in biomass or growth rate. In so doing, the plants contemplated herein permit the manufacture of products such as biodegradable plastics, vanillin, indigo, adipic acid, 2-phenylethanol, 1,3-propanediol, sorbitol, fructan polymers and lactic acid as well as therapeutic, nutraceutic and diagnostic agents without incurring the previously observed deleterious effects on growth and viability.

Accordingly, one aspect of the present invention provides a method for generating a plant-based bioreactor system, said method comprising selecting a plant having a high efficiency carbon assimilation mechanism, rapid growth rate and/or high biomass production and/or reserves of metabolites or having a capacity to generate such reserves and/or which possess metabolic and/or biosynthetic pathways useful in the manufacture of a product of interest or a precursor form thereof; genetically modifying cells of the plant to enable access to said metabolites and/or metabolic or biosynthetic pathways; and then regenerating a genetically modified plant from said cells.

The present invention is particularly directed to C4 grasses, however, other non-grass C4 plants such as woody or herbaceous plants which utilise the C4 pathway are also contemplated by, and are within the scope of, the present invention.

In a preferred embodiment of the present invention, the subject plant is a C4 grass. In an even more preferred embodiment the plant is sugarcane. As used herein, the term sugarcane is to be understood to include, inter alia, plants of the *Saccharum* genus, incl. *S. robustum, S. offinarum*, and *S. spontaneum* and hybrid *Saccharum* sp., incl. modern sugarcane cultivars.

The preferred compounds to be produced by the plant bioreactor include: vanillin, sorbitol, polyhydroxyalkanoates (PHA) such as poly-(D-3-hydroxybutyrate) (PHB), indigo, fructan, lactic acid, adipic acid, 1,3-propanediol, 2-phenylethanol and pHBA. However, the present invention also extends to the use of C4 grasses as bioreactors to generate a compounds such as therapeutics, nutrapharmaceuticals, diagnostic agents including, for example, single chain antibodies, industrial enzymes and the like.

The present invention contemplates, therefore, a method for producing a product of interest including a product or intermediate of a biosynthetic or metabolic pathway in a C4 grass, said method comprising expressing one or more genetic sequences which encode one or more enzymes or proteins required for the production of the product or intermediate or a homolog or precursor thereof or which induces gene silencing of genetic material which encodes an enzyme or protein in a biosynthetic or metabolic pathway in cell of a C4 grass plant such that the product or intermediate accumulates in the cytosol, storage vacuole, plastid or non-plastid organelles of the cell, or accumulates in the juice or vascular fluid of the plant.

The present invention therefore provides for the production of a product in a C4 grass wherein product accumulation is at least in part predicated on the direct activation or inhibition (including down-regulation) of an enzyme in a biosynthetic or metabolic pathway by the administration to the plant of an enzyme inhibitor or activator. Reference to an "enzyme inhibitor or activator" includes genetic materials which, for example, induce (post-transcriptional or transcriptional gene silencing of a structural gene or positive or negative regulator gene.

In one preferred embodiment, increased accumulation of a product or intermediate from a biosynthetic or metabolic pathway is a result of inhibition of one or more biosynthetic or metabolic enzymes and optionally redirecting metabolites down another biosynthetic or metabolic pathway.

In another preferred embodiment, the present invention contemplates the use of sugarcane as a bioreactor. Therefore, alteration to the gene expression profile of sugarcane to effect the production of an endogenous metabolite at an increased level, or to produce any heterologous metabolite is within the scope of the present invention. Accordingly, induction or supression of any biosythetic genes in sugarcane, such as described herein, is to be considered within the scope of the present invention.

Typically, the production of one or more metabolites or heterologous proteins, polypeptides or peptides in a plant is achieved by expression of a nucleic acid molecule encoding the metabolite or protein, polypeptide or peptide of interest. Any nucleic acid which encodes a protein, polypeptide or peptide of interest is contemplated by the present invention. However, preferred nucleic acids include those encoding:

(i) vanillin biosynthetic enzymes, including 3-dehydroshikimate dehydratase, catechol-o-methyltransferase, aryl aldehyde dehydrogenase, feruloyl-CoA synthetase, enoyl-CoA hydratase/aldolase;

(ii) sorbitol biosynthetic enzymes, including glucose/fructose oxidoreductase;

(iii) PHA biosynthetic enzymes, including 3-ketothiolase, acetoacetyl-CoA reductase, PHA synthase, enoyl hydratase, 3-hydroxyacyl-acyl carrier protein:CoA tranferase;

(iv) indigo biosynthetic enzymes, including tryptophanase, L-tryptophan indole lyase, napthalene dioxygenase, *R. eutrophica* bec gene product;

(v) fructan biosynthetic enzymes, including fructosyltransferases and levansucrases;

(vi) lactic acid biosynthetic enzymes, including lactate dehydrogenase;

(vii) adipic acid biosynthetic enzymes, including 3-dehydroshikimate dehydratase, protocatechuate decarboxylase and catechol 1,2-dioxygenase;

(viii) petroselinic acid biosynthetic enzymes, including 3-ketoacyl-ACP synthase;

(ix) 1,3-propanediol biosynthetic enzymes including glycerol dehydratase, 1,3-propanediol oxidoreductase, glycerol-3-phosphate dehydrogenase, and glycerol-3-phosphatase; and/or (x) 2-phenylethanol biosynthetic enzymes including aromatic-L-amino acid decarboxylase, 2-phenylethylamine oxidase and aryl alcohol dehydrogenase.

(xi) pHBA biosynthetic enzymes including 4-hydroxycinnamoyl-CoA hydratas/lyase (HCHL) and chorismate pyruvate lyase (CPL).

Any of a number of products may be produced according to the present invention. Examples of compounds that may be produced via metabolic engineering of a subject plant include: vanillin (4-hydroxy-3-methoxybenzaldehyde); sorbitol; PHAs; indigo; fructan; lactic acid (2-hydroxypropanoic Acid); adipic acid; 1,3 propanediol, 2-phenylethanol and pHBA. These compounds, however, are only examplary, and the present invention is predicated on the use of C4 plants as bioreactors for any compound that can be synthesised in the plant. Accordingly, the present invention is not limited to any one product or method for producing the product.

In a particularly preferred embodiment, the present invention contemplates a method for accumulating polymers comprising one or more species of hydroxyalkanoic acid monomer in a C4 grass, said method comprising expressing one or more genetic sequences which encode enzymes required for the production of the polymers or a homolog or precursor thereof in a cell of a C4 grass such that PHA polymers accumulate in the cytosol, storage vacuole or plastid or non-plastid organelle of said cell.

The present invention further contemplates a method for generating a plant which produces PHAs, said method comprising introducing into cells of said plant a genetic sequence comprising:

(i) a nucleotide sequence encoding a phaA or homolog thereof;

(ii) a nucleotide sequence encoding phaB or homolog thereof;

(iii) a nucleotide sequence encoding phaC or homolog thereof;

(iv) a nucleotide sequence encoding phaC1 or homolog thereof;

(v) a nucleotide sequence encoding phaG or homolog thereof;

(vi) a nucleotide sequence encoding phaJ or homolog thereof (vii) SEQ ID NO:1 or SEQ ID NO:3 or SEQ ID NO:10 or SEQ ID NO:12 or a nucleotide sequence having at least 60% identity thereto after optimal alignment, or capable of hybridizing to SEQ ID NO:1 or SEQ ID NO:3 or SEQ ID NO:10 or SEQ ID NO:12 or a complementary form thereof under low stringency conditions;

(viii) SEQ ID NO:4 or SEQ ID NO:6 or SEQ ID NO:13 or SEQ ID NO:15 or a nucleotide sequence having at least 60% identity thereto after optimal alignment, or capable of hybridizing to SEQ ID NO:4 or SEQ ID NO:6 or SEQ ID NO:13 or SEQ ID NO:15 or a complementary form thereof under low stringency conditions;

(ix) SEQ ID NO:7 or SEQ ID NO:9 or SEQ ID NO:16 or SEQ ID NO:18 or a nucleotide sequence having at least 60% identity thereto after optimal alignment, or capable of hybridizing to SEQ ID NO:7 or SEQ ID NO:9 or SEQ ID NO:16 or SEQ ID NO:18 or a complementary form thereof under low stringency conditions;

(x) SEQ ID NO:19 or SEQ ID NO:21 or SEQ ID NO:22 or SEQ ID NO:24 or SEQ ID NO:25 or SEQ ID NO:27 or a nucleotide sequence having at least 60% identity thereto after optimal alignment, or capable of hybridizing to SEQ ID NO:19 or SEQ ID NO:21 or SEQ ID NO:22 or SEQ ID NO:24 or SEQ ID NO:25 or SEQ ID NO:27 or a complementary form thereof under low stringency conditions;

(xi) SEQ ID NO:28 or SEQ ID NO:30 or a nucleotide sequence having at least 60% identity thereto after optimal alignment, or capable of hybridizing to SEQ ID NO:28 or SEQ ID NO:30 or a complementary form thereof under low stringency conditions;

(xii) SEQ ID NO:31 or SEQ ID NO:33 or a nucleotide sequence having at least 60% similarity thereto or capable of hybridizing to SEQ ID NO:31 or SEQ ID NO:33 or a complementary form thereof under low stringency conditions;

and then regenerating a plant from said cells.

A convenient C4 grass for use in the present invention is sugarcane. Sugarcane has certain advantages, which make it a useful crop for use as a bioreactor including, inter alia, its efficient carbon fixation, high biomass accumulation, rapid growth and natural ability to accumulate large quantities of sucrose. Moreover, it achieves this very efficiently by collecting solar radiation and converting it into a carbon sink (i.e. sucrose). Sugarcane is also a hardy crop, is relatively easy to grow and provides a large biomass capability. A micropropagation system is already available and an industry infrastructure in existence.

In another embodiment, the present invention provides a method for generating a plant which produces vanillin or a precursor thereof, said method comprising introducing into cells of said plant a genetic sequence comprising at least one of the following:

(i) a nucleotide sequence encoding a 3-dehydroshilimate dehydratase;
(ii) a nucleotide sequence encoding catechol-o-methyltransferase;
(iii) a nucleotide sequence encoding aryl aldehyde dehydrogenase;
(iv) a nucleotide sequence encoding feruloyl-CoA synthetase;
(v) a nucleotide sequence encoding enoyl-CoA hydratase;
(vi) a nucleotide sequence encoding enoyl-CoA aldolase; and/or
(vii) a nucleotide sequence encoding a homolog of any one of (i) through (vi) and then regenerating a plant from said cells.

Another aspect of the present invention contemplates a method for producing sorbitol in a C4 grass, said method comprising expressing one or more genetic sequences encoding a glucose-fructose oxidoreductase, in cells of a C4 grass such that sorbitol accumulates anywhere in the cell or extracellular matrix of the plant.

In another embodiment, the present invention is directed to a method for generating a plant which produces indigo or a precursor thereof, said method comprising introducing into cells of said plant a genetic sequence comprising at least one of the following:
(i) a nucleotide sequence encoding genetic sequences encoding tryptophanase;
(ii) a nucleotide sequence encoding L-tryptophan indole lyase;
(iii) a nucleotide sequence encoding napthalene dioxygenase;
(iv) a nucleotide sequence comprising the *R. eutropha* bec gene;
(v) the nucleotide sequence set forth in Genbank accession number D14279, or a nucleotide sequence having at least 60% identity thereto after optimal alignment, or capable of hybridizing to Genbank D14279 under low stringency conditions.
(vi) the nucleotide sequence set forth in Genbank accession number M83949, or a nucleotide sequence having at least 60% identity thereto after optimal alignment, or capable of hybridizing to Genbank M83949 under low stringency conditions.
(vii) the nucleotide sequence set forth in Genbank accession number AF306552, or a nucleotide sequence having at least 60% identity thereto after optimal alignment, or capable of hybridizing to Genbank AF306552 under low stringency conditions.

and then regenerating a plant from said cells.

In another embodiment, the present invention relates to a method for generating a C4 grass plant which produces a fructan or a precursor thereof, said method comprising introducing into cells of said plant a genetic sequence comprising at least one of the following:
(i) a nucleotide sequence encoding a fructosyltransferase
(ii) a nucleotide sequence encoding a levansucrase;
(iii) the nucleotide sequence set forth in Genbank accession number AY150365, or a nucleotide sequence having at least 60% identity thereto after optimal alignment, or capable of hybridizing to Genbank AY150365 under low stringency conditions.

and then regenerating a plant from said cells.

In another embodiment, the present invention contemplates a method for generating a plant which produces lactic acid or a precursor thereof, said method comprising introducing into cells of said plant a genetic sequence encoding lactate dehydrogenase and then regenerating a plant from said cells.

In another embodiment, the present invention contemplates a method for generating a plant which produces adipic acid or a precursor thereof, said method comprising introducing into cells of said plant a genetic sequence comprising at least one of the following:
(i) a nucleotide sequence encoding a 3-dehydroshikimate dehydratase and/or;
(ii) a nucleotide sequence encoding protochatechuate decarboxylase;
(iii) a nucleotide sequence encoding catechol 1,2-dioxygenase;
(iv) a nucleotide sequence encoding 3-ketoacyl-ACP synthase; and/or
(v) a nucleotide sequence encoding a homolog of any one of (i) though (iv)

and then regenerating a plant from said cells.

In another embodiment, the present invention contemplates a method for generating a plant which produces 1,3-propanediol or a precursor thereof, said method comprising introducing into cells of said plant a genetic sequence comprising at least one of the following:
(i) a nucleotide sequence encoding a glycerol dehydratase and/or;
(ii) a nucleotide sequence comprising the dhaB gene from *Klebsiella pneumoniae*, or a homolg thereof;
(iii) a nucleotide sequence encoding 1,3-propanediol oxidoreductase;
(iv) a nucleotide sequence comprising the dhaT gene from *Klebsiella pneumoniae* or homolg thereof;
(v) a nucleotide sequence encoding glycerol-3-phosphate dehydrogenase;
(vi) a nucleotide sequence encoding glycerol-3-phosphatase; and/or
(vi) a nucleotide sequence encoding a homolog of any one of (i) though (vi)

and then regenerating a plant from said cells.

In another embodiment, the present invention contemplates a method for generating a plant which produces 2-phenylethanol or a precursor thereof, said method comprising introducing into cells of said plant a genetic sequence comprising at least one of the following:
(i) a nucleotide sequence encoding a aromatic-L-amino acid decarboxylase;
(ii) a nucleotide sequence encoding 2-phenylethylamine oxidase;
(iii) a nucleotide sequence encoding aryl-alcohol dehydrogenase; and/or
(iv) a nucleotide sequence encoding a homolog of any one of (i) though (iii)

and then regenerating a plant from said cells.

In another aspect, the present invention contemplates a method for generating a plant which produces pHBA or a precursor thereof, said method comprising introducing into cells of said plant a genetic sequence comprising at least one of the following:
(i) a nucleotide sequence encoding hydroxycinnamoyl-CoA hydratase/lyase;
(ii) a nucleotide sequence encoding chorismate pyruvate lyase;
(iii) a nucleotide sequence comprising the ubiC gene from *E. coli*, or a homolg thereof; and/or
(iv) a nucleotide sequence comprising the HCHL gene from *Pseudomonas fluorescens* or homolg thereof;

and then regenerating a plant from said cells.

Preferably, the plant is a C4 grass and, in a particularly preferred embodiment, sugarcane.

A further aspect of the present invention provides a transfected or transformed cell, tissue, or organ from a C4 grass, which comprises a nucleotide sequence encoding one or more enzymes required for the production of a useful product as well as severed or cut parts of a genetically modified plant including stem, flower, seed or other reproductive parts.

Accordingly, another aspect of the present invention provides a genetically modified C4 grass having cells carrying one or more genetic sequences such that one of the following products in the cytosol, storage vacuole, non-plastid organelle or extracellular matrix of said cells:

(i) polyhydroxy-alkanoate polymers
(ii) vanillin
(iii) sorbitol
(iv) indigo
(v) fructans
(vi) lactic acid
(vii) adipic acid
(viii) 1,3-propanediol
(ix) 2-phenylethanol
(x) pHBA The present invention extends to parts of plants tissue including leaves, stems, vascular bundles, bark, reproductive material, roots and any extracted liquid ("juice") from said plant.

In order to direct product accumulation to a desired sub-cellular location, particular specific "target sequences" may be incorporated into the genetic constructs described above.

A target sequence includes a signal sequence such as a signal sequence to direct the protein to a plastid, vacuole, mitochondrion, peroxisome or ontologically related organelles, or other appropriate organ or tissue.

The plants of the present invention may also be further "tagged" with a reporter that identifies the plant as a plant bioreactor. Any number of physiological or genetic tags would be suitable, and readily identified by one of skill in the art.

Accordingly, the present invention contemplates a plant suitable for use as a bioreactor that has been tagged with a genetic sequence which encodes or comprises a genotypic or phenotypic feature that allows differentiation of the plant bioreactor from a wild-type plant, or which identifies the plant as a proprietary plant.

The plant-based bioreactor system of the present invention is useful in enabling the production of molecules such as PHAs, pHBA, vanillin, sorbitol, indigo, fructans, lactic acid, adipic acid, 1,3-propanediol, 2-phenylethanol, inter alia, by a number of different parties such as different commercial entities. The present invention extends, therefore, to a data processing system to monitor the use of the plants and/or the production of target molecules.

Accordingly, another aspect of the present invention contemplates a method for generating a target molecule in a sucrose-accumulating plant, said method comprising:

(i) providing a plant or cells of a plant to a party; and
(ii) permitting the party to generate and harvest molecules from said plant or cells of said plant receiving and processing data from said party.

The data received from the party includes, for example, numbers of plants grown and/or harvested, the types of genetic constructs introduced into the cells and/or income received from sale of the products.

Figure 1:
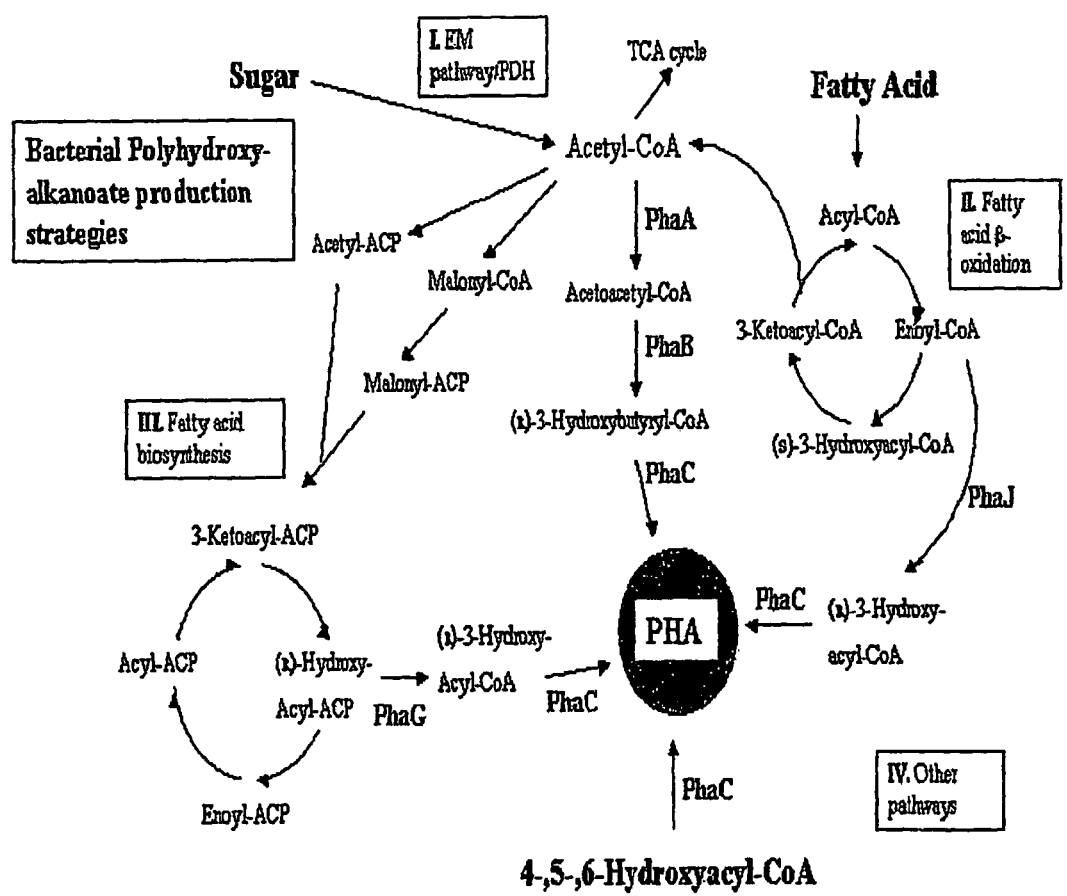
FIG. 1 is a schematic representation showing the four different biosynthetic strategies employed by bacteria that use PHAs as an energy source.

A summary of sequence identifiers used throughout the subject specification is provided below in Table 1:

TABLE 1

SUMMARY OF SEQUENCE IDENTIFIERS

| SEQUENCE ID NO: | DESCRIPTION |
|---|---|
| 1 | Nucleotide sequence (phaA) encoding PhaA without signal sequence (hence, the PhaA remains in the cytosol) |
| 2 | Amino acid sequence of PhaA without signal sequence |
| 3 | Nucleotide sequence (phaA) encoding PhaA without signal sequence (hence, the PhaA remains in the cytosol) modified at 5' and 3' ends for insertion into a vector |
| 4 | Nucleotide sequence (phaB) encoding PhaB without signal sequence (hence, the PhaB remains in the cytosol) |
| 5 | Amino acid sequence of PhaB without signal sequence |
| 6 | Nucleotide sequence (phaB) encoding PhaB without signal sequence (hence, the PhaB remains in the cytosol) modified at 5' and 3' ends for insertion into a vector |
| 7 | Nucleotide sequence (phaC) encoding PhaC without signal sequence (hence, the PhaC remains in the cytosol) |
| 8 | Amino acid sequence of PhaC without signal sequence |
| 9 | Nucleotide sequence (phaC) encoding PhaC without signal sequence (hence, the PhaC remains in the cytosol) modified at 5' and 3' ends for insertion into a vector |
| 10 | Nucleotide sequence (phaA) encoding PhaA targeted to plastid |
| 11 | Amino acid sequence of PhaA with signal sequence to target to the plastid |
| 12 | Nucleotide sequence (phaA) encoding PhaA targeted to plastid modified at 5' and 3' ends for insertion into a vector |

TABLE 1-continued

SUMMARY OF SEQUENCE IDENTIFIERS

| SEQUENCE ID NO: | DESCRIPTION |
|---|---|
| 13 | Nucleotide sequence (phaB) encoding PhaB targeted to plastid |
| 14 | Amino acid sequence of PhaB with signal sequence to target to the plastid |
| 15 | Nucleotide sequence (phaB) encoding PhaB targeted to plastid modified at 5' and 3' ends for insertion into a vector |
| 16 | Nucleotide sequence (phaC) encoding PhaC targeted to plastid |
| 17 | Amino acid of PhaC with signal sequence to target to the plastid |
| 18 | Nucleotide sequence (phaC) encoding PhaC targeted to modified at 5' and 3' ends for insertion into a vector |
| 19 | Nucleotide sequence (phaC1) encoding PhaC1 without signal sequence (hence, the PhaC1 remains in the cytosol) |
| 20 | Amino acid sequence of PhaC1 without signal sequence |
| 21 | Nucleotide sequence (phaC1) encoding PhaC1 without signal sequence modified at 5' and 3' ends for insertion into a vector |
| 22 | Nucleotide sequence (phaC1) encoding PhaC1 targeted to the peroxisome |
| 23 | Amino acid sequence of PhaC1 with signal sequence to target to the peroxisome |
| 24 | Nucleotide sequence (phaC1) encoding PhaC1 targeted to the peroxisome modified to 5' and 3' ends for insertion into a vector |
| 25 | Nucleotide sequence of (phaC1) encoding PhaC1 targeted to the plastid |
| 26 | Amino acid sequence of PhaC1 with signal sequence to target to the plastid |
| 27 | Nucleotide sequence (phaC1)) encoding PhaC1 targeted to the plastid modified at 5' and 3' ends for insertion into a vector |
| 28 | Nucleotide sequence (phaG) encoding PhaG targeted to the plastid |
| 29 | Amino acid sequence of PhaG with signal sequence to target to the plastid |
| 30 | Nucleotide sequence (phaG) encoding PhaG targeted to the plastid modified to 5' and 3' ends for insertion into a vector |
| 31 | Nucleotide sequence (phaJ) encoding PhaJ targeted to the peroxisome |
| 32 | Amino acid sequence of PhaJ with signal sequence to target to the peroxisome |
| 33 | Nucleotide sequence (phaJ) encoding PhaJ targeted to the peroxisome modified to 5' and 3' ends for insertion into a vector |
| 34 | TphaF |
| 35 | PhaF |
| 36 | PhbF |
| 37 | PhcF |
| 38 | PhaR |
| 39 | PhbR |
| 40 | PhcR |
| 41 | PhaC1Cf |
| 42 | PhaC1Cr |
| 43 | PhaC1PF |
| 44 | PhaJF |
| 45 | PhaJR |
| 46 | PhaGF |
| 47 | PhaGR |
| 48 | SSP-F |
| 49 | SSP-R |
| 50 | primer 3 |
| 51 | primer 4 |
| 52 | primer 5 |
| 53 | primer 6 |

A list of abbreviations used herein is provided in table 2.

TABLE 2

Abbreviations

| ABBREVIATION | Description |
|---|---|
| 1,3-PD | 1,3-Propanediol |
| 2-PE | 2-Phenylethanol |
| CAM | Crassulacean Acid Metabolism |
| DW | Dry weight |
| GFOR | Glucose-Fructose Oxidoreductase |
| GFP | Green Fluorescent Protein |
| PEP | Phosphoenolpyruvate |
| PEPcase | Phosphoenolpyruvate carboxylase |
| PET | Polyethylene terephthalate |
| sPET | Isosorbide PET |
| PHA | Polyhydroxyalkanoate |
| PHB | Polyhydroxybutyrate |
| pHBA | poly hydroxybenzaldehyde |
| PHV | Polyhydroxyvalerate/Poly-3-hydroxypentanoate |
| Rubisco | Ribulose bisphosphate carboxylase/oxygenase |
| WT | Wild type |

DETAILED DESCRIPTION OF THE PREFERRED EMBODIMENTS

The present invention provides a plant-derived bioreactor system, which is capable of withstanding the extra metabolic load placed on individual plants without resulting in deleterious growth effects. Hence, until the advent of the present invention, plants have been engineered to make small quantities of a desired product, their capacity to do so being limited, and their ability to go on doing so prevented, by these deleterious growth effects. In accordance with the present invention, certain plants were selected on the basis of the presence of highly efficient photosynthetic mechanisms for the assimilation of carbon, particular metabolic reserves, and/or useful metabolic and/or biosynthetic pathways. Grasses, and particularly C4 grasses, were identified as having particularly efficient mechanisms for the assimilation of carbon, a high growth rate and high accumulation of biomass and hence are useful as bioreactors for the production of a wide range of products. Furthermore, the C4 grass, sugarcane, is particularly useful, as this plant stores sugars in dimeric and/or polymeric forms that may be utilized when needed, for example, to supply energy during times of significant environmental stress. This store of carbohydrate would provide a ready supply of substrate for many metabolic pathways, and utilization of this store would not stress the producing plant. Therefore, the present invention is predicated, in part, on the identification of a subset of plants, namely the C4 grasses, and particularly sugarcane, as useful bioreactors on the basis of their high carbon assimilation rate, rapid growth, high biomass production and large store of carbohydrate.

Accordingly, one aspect of the present invention provides a method for generating a plant-based bioreactor system, said method comprising selecting a plant having a high efficiency carbon assimilation mechanism, rapid growth rate and/or high biomass production and/or reserves of metabolites or having a capacity to generate such reserves and/or which possess metabolic and/or biosynthetic pathways useful in the manufacture of a product of interest or a precursor form thereof; genetically modifying cells of the plant to enable access to said metabolites and/or metabolic or biosynthetic pathways; and then regenerating a genetically modified plant from said cells.

The terms "grass", "grasses" and the like are to be understood as reference to any member of the Gramineae plant family whether currently known or not. This family currently encompasses approximately 660 plant genera including 10,000 plant species. It will be readily apparent to the skilled artisan when examining a given plant, either known or novel, whether the plant is a grass.

Preferably, the grass is a C4 grass.

To minimise losses of carbon and nitrogen resulting from photorespiration, some plants such as corn and sugarcane that grow in hot climates have a different system for fixing $CO_2$, called C4 photosynthesis, than plants that grow in more temperate climates (which have C3 photosynthesis). The leaf anatomy of plants such as corn and sugarcane is different from that of temperate plants. The vascular bundles of these leaves are surrounded by a wreath of thick-walled parenchyma cells called bundle sheath cells, where most of the carbon-fixation takes place.

During C4 photosynthesis, $CO_2$ in the mesophyll cells is condensed with a 3C compound called phosphoenolpyruvic acid (PEP), by the action of the enzyme PEP carboxylase. This produces the 4C compound oxaloacetic acid which is then converted to malic or aspartic acid. The malic or aspartic acid is then moved through plasmodesmata (at the expense of ATP) into the bundle sheath cells.

In the bundle sheath cells, the 4C compounds are decarboxylated to release $CO_2$ and PEP. The $CO_2$ collected in the many mesophyll cells is concentrated into a few bundle sheath cells. Therefore, the plants can maintain a higher concentration of $CO_2$ in the bundle sheath cells (where the Calvin-Benson cycle of photosythesis occurs) than it can elsewhere in the leaf. This higher concentration of $CO_2$ minimises photorespiration.

The C4 pathway is more expensive energetically than C3 photosynthesis, but this is offset by the resulting decrease in photorespiration (where under certain conditions, plants may lose 30% of fixed carbon,). For this reason, C4 plants are well adapted to environments that promote high levels of photorespiration (viz. subtropical and tropical climes).

The fundamentals of C4 photosynthesis are shown schematically in Figure *. The photosynthesis processes of C4 plants are divided between mesophyll and bundle sheath cells. Two steps of C4 photosynthesis which occur in the mesophyll cells are the light-dependent reactions and a preliminary fixation of $CO_2$ into malate or aspartate (a 4C compound). This C4 compound is transported to the bundle sheath cells, and is decarboxylated to form $CO_2$ and PEP. The released $CO_2$ is re-fixed by Rubisco and the Calvin-Benson cycle. The PEP is then recycled back to the mesophyll cells, and the photosynthates are distributed throughout the plant.

One defining aspect of a C4 plant is "Kranz anatomy" (German for "wreath"). This term refers to the characteristic one, or two concentric, layer(s) (wreath[s]) of bundle sheath cells, around the vascular bundles of the leaves. The mesophyll cells surrounding the bundle sheath cells fix $CO_2$ via PEP carboxylase to form 4C organic acids. These are transported to the bundle sheath cells and are decarboxylated to regenerate $CO_2$, which is then refixed by the typical C3 photosynthetic pathway found in non-C4 plants. The system thus acts as a $CO_2$ pump, increasing the $CO_2$ concentration in the bundle sheath to a level where photorespiration is minimised.

Accordingly, for the purposes of the present invention C4 plants are to be understood as plants which exhibit at least one of the following characteristics in at least some part of the plant:

(i) Kranz anatomy;
(ii) fixation of $CO_2$ into a 4 carbon compound; and/or
(iii) decarboxylation of a 4 carbon compound.

For the purposes of the present invention, a given plant need not exhibit all of the above characteristics to be considered a C4 plant. For example, *Borszczowia aralocaspica* (Chenopodiaceae) has the photosynthetic features of C4 plants, yet lacks Kranz anatomy. This species accomplishes C4 photosynthesis through spatial compartmentation of photosynthetic enzymes, and by separation of two types of chloroplasts and other organelles in distinct positions within the chlorenchyma cell cytoplasm. Accordingly, insofar as the present invention relates to C4 plants, this is to be understood as those which exhibit 1, 2 or all 3 of the above characteristics.

It is also to be understood that the subject plant need not exhibit one or all of these criteria at all times. Some plant species, such as the amphibious leafless sedge, *Eleocharis vivipara*, can exhibit C3 and C4 characteristics such as those shown above depending on whether it is grown in a terrestrial or aquatic environment. In addition, the Cassava plant has photosynthetic mechanisms which are typical of a C3 plant, yet some studies have shown that both C3 and C4 enzymatic systems function in Cassava The dominant photosynthetic pathway varies between C3 and C4 depending on temperature: at lower temperatures, photosynthesis follows a C3 path, and at higher temperatures, a C4 path.

Therefore, for the purposes of the present invention, C4 plants are to be understood as those plants capable of exhibiting one or more of the above characteristics under any given environmental condition. The present is not limited by the method of photosynthesis used at a given time by a given plant, the plant need only be capable of expressing at least one of the above characteristics associated with C4 photosynthesis.

In addition, plants utilising the Crassulacean Acid Metabolism (CAM) pathway are also to be considered within the definition of a C4 plant for the purposes of the present invention.

The term "Crassulacean" refers to the Stonecrop family (Crassulaceae) and related succulents in which this process is common. To date, plants in more than 18 different families including Cactaceae (Cactus family) and Bromeliaceae (Pineapple family) have been shown to carry out CAM metabolism. The term "Acid" is derived from the observation that these plants accumulate large amounts of C4 organic acids in the dark.

Plants with CAM metabolism are typically adapted to dry, hot, high-light environments. CAM is largely a mechanism to conserve water. Plants in dry environments utilise CAM as they cannot afford to lose water by opening their stomata during the day. CAM plants circumvent water loss during the day by opening up the stomates at night to obtain carbon dioxide.

Carbon dioxide is accumulated in CAM plants using PEP carboxylase, and the fixed carbon is stored as 4-carbon compounds such as malate, as in C4 plants.

The $CO_2$ obtained during the night is stored as a C4 acid until ATP and NADPH are available the following day as a result of the light reactions of photosynthesis. The C4 acid is then decarboxylated and the $CO_2$ fixed by the Calvin-Benson cycle. Thus, in CAM plants there is a temporal separation of initial carbon fixation and the Calvin-Benson cycle, whereas in other C4 plants there is a spatial separation.

In summary the sequence of events in CAM plants is:

Night→stomates open→nocturnal transpiration (lower than diurnal) and carbon fixation by PEPcase→OAA produced→reduced with NADPH to malate→shuttled into vacuole as malic acid→malic acid content of vacuole increases→starch depleted to provide PEP for carboxylation→day→stomates close→transpiration decreased→malic acid content decreases→resulting malate decarboxylated to provide carbon dioxide for Calvin cycle→starch content increases.

Accordingly, as CAM plants exhibit fixation of $CO_2$ into a 4C compound, and decarboxylation of a 4C compound, they are to be understood as within the definition of C4 plants for the purposes of the present invention.

The present invention is particularly directed to C4 grasses; however, other non-grass C4 plants such as woody or herbaceous plants which utilise the C4 pathway are also contemplated by, and are within the scope of, the present invention.

In a preferred embodiment of the present invention the subject plant is a grass, more preferably a C4 grass. In a particularly preferred embodiment the C4 grass is a member of the *Saccharum* genus, and particularly the *Saccharum* hybrid, sugarcane.

Commercially grown sugarcane varieties are mainly interspecific hybrids and are vegetatively propagated. There are about six different species contributing to the gene pool: *Saccharum officinarum, Saccharum robustum, Saccharum barberi, Saccharum spontaneum, Saccharum sinense* and *Erianthus* sp. Hence, the scope of present invention is not to be limited to any one variety but should be regarded as extending to and encompassing other species of *Saccharum*.

The preferred compounds to be produced by the plant bioreactor include: vanillin, sorbitol, PHAs, indigo, fructan, lactic acid, adipic acid, 1,3-propanediol and 2-phenylethanol. However, the present invention extends to the use of C4 grasses as bioreactors to generate a compounds such as therapeutics, nutrapharmaceuticals, diagnostic agents including single chain antibodies, industrial enzymes and the like. However, the present invention is in no way limited by the exemplified compounds and methods.

The present invention contemplates, therefore, a method for producing a product of interest including a product or intermediate of a biosynthetic or metabolic pathway in a C4 grass, said method comprising expressing one or more genetic sequences which encode one or more enzymes or proteins required for the production of the product or intermediate or a homolog or precursor thereof or which induces gene silencing of genetic material which encodes an enzyme or protein in a biosynthetic or metabolic pathway in cell of a C4 grass plant such that the product or intermediate accumulates in the cytosol, storage vacuole, plastid or non-plastid organelles of the cell, or accumulates in the juice or vascular fluid of the plant.

For the purposes of the present invention, the application of a plant as a bioreactor, is to be also understood as the alteration of existing plant metabolism or the introduction of new plant metabolism to generate a non-endogenous plant product or an endogenous plant product at non-native levels.

In the case of the metabolic engineering of native plant biochemical pathways, this may be achieved via a number of means. Alterations to the metabolic activity of an organism can be made at the gene, gene expression and protein levels.

Metabolic engineering may be affected at the protein level in an organism by the administration of particular enzyme activators or inhibitors. For example, the activity of particular biosynthetic enzymes may be regulated by the administration of particular enzyme inhibitors to the plant. These inhibitors may directly effect the accumulation of a product by reducing the activity of a particular biosynthetic enzyme. In addition indirect effects such as the redirection of metabolic flux into other pathways may be a product of a particular enzyme inhibition. For example, the blocking of a particular enzyme may lead to the buildup of an intermediate which may then be directed into a different metabolic pathway, leading to the increased accumulation of the product of the second pathway.

The present invention therefore contemplates the production of a product in a C4 grass wherein product accumulation is at least in part predicated on the direct activation or inhibition of an enzyme in a biosynthetic pathway by the administration to the plant of an enzyme inhibitor or activator. An enzyme "inhibitor" or "activator" also includes genetic inhibitors or activators; ie. nucleic acid molecules or RNAi-type molecules which induce gene silencing or a structural gene or a regulatory gene which positiviely or negatively regulates structural gene expression.

In a preferred embodiment, increased accumulation of a product or intermediate from a biosynthetic or metabolic pathway is a result of inhibition of one or more biosynthetic enzymes in the pathway or re-direction of metabolite flow down another pathway.

Particular biosynthetic or metabolic pathways may be induced in plants, parts of plants and/or plant cells in culture by the addition of elicitors, or by changes in environmental conditions. Gene expression in plants and other organisms is mediated by a number of physical, chemical and biotic factors. Physical factors such as light intensity and photoperiod have been implicated in the expression of many plant genes including genes involved in morphogenesis and plant secondary metabolism. For example, the anthocyanin biosynthetic genes, PAL and CHS are induced by increased light intensity and increased photoperiod. In a similar way, temperature and osmotic stresses have also been shown to alter gene expression in a broad range of biological systems. For example, the KIN1, COR15a, and LT178 genes in *Arabidopsis thaliana* are sensitive to induction by low temperatures (Knight et al., *Plant Cell* 11(5): 875-886, 1999), and a range of heat shock proteins and glycolytic enzymes are induced in the bacterium *Lactobacillus rhamnosus* in response to heat and osmotic stress (Prasad et al., *Appl. Environ. Microbiol.* 69(2): 917-925, 2003). Many of these gene expression changes are a result of stress to the cells. In addition, other physical factors such as wounding and drought have also been associated with altered gene expression in plants. For example in the fig tree *Ficus carica*, drought stress induced genes encoding a peroxidase, a chitinase and a trypsin inhibitor (Kim et al., *Plant Cell Physiol.* 44(4): 412-414).

Chemical inducers of gene expression have been identified for many biological systems and specific gene promoters. Examples of these include the induction of chalcone synthase, a phenylpropanoid pathway enzyme, by chemical elictors such as jasmonate. Also, bacterially synthesized lipochitooligosaccharides Nod factors) induce the early nodulin (ENOD) genes in leguminous plants (Fang and Hirsch, *Plant Physiol.* 115:53-68, 1998). Several compounds have also been demonstrated to induce gene expression associated with plant defence, such as silicon dioxide, phosphate salts, and polyunsaturated fatty acids (Sticher et al., *Annu. Rev. Phytopathol.* 35: 235-270, 1997).

A number of biological agents have also been demonstrated to alter gene expression in other organisms. For example, many phytopathogenic fungi and bacteria induce the expression of a number of defence-related genes, such as the PR proteins, β-glucanases, terpenoid biosynthetic enzymes and genes in the 'salicylic acid' defence pathway. Non-pathogenic, microbial colonists of plant induce yet another different set of genes in the plant host (Han et al., *Phytopathology* 90: 327-332, 2000).

Alterations or changes to cultural practices, culture conditions and growth conditions, including photoperiod and/or temperature, are considered to be conditions which are not standard conditions for the growth of the plant or cell. For example, growth of a plant or plant cell culture under a 24 hour light, would be considered an altered photoperiod for the purposes of the present invention. Second, growth of a plant at a temperature substantially above or below the optimum growth temperature of said plant, plant cell culture or bacterial culture would be considered an altered temperature for the purposes of the present invention. The preceeding examples in no way limit the invention and it will be clear to those of skill in the art what constitutes altered, changed or abnormal conditions pertaining to a given cell, cell culture, plant or organism.

Methods of altering gene expression in sugarcane contemplated by the present invention are to be understood as physical processes or conditions, chemical compounds and biological, including genetic agents. Non-limiting examples of physical agents include alterations to culture and/or growth conditions of the cell or organism, light intensity and/or photoperiod, temperature, growing season, and or physical wounding. Examples of chemical agents that may alter gene expression in plants include phytohormones such as auxins, cytokinins and gibberellins; signalling molecules such as flavanoids, saccharides, sterols and peptides; herbicides and antibiotics. Examples of biological agents contemplated by the present invention include microorganisms, such as bacteria and fungi; viruses; transposons and plasmids as well as RNAi-inducing genetic molecules including a hairpin loop or other means to induce gene silencing (eg. post-transcriptional gene silencing). The preceeding examples are only illustrative in nature and in no way limit the invention to the said agents.

Accordingly, the present invention contemplates the use of sugarcane as a bioreactor.

Therefore, alteration to the gene expression profile of sugarcane to effect the production of an endogenous metabolite at an increased level, or to produce any heterologous metabolite is within the scope of the present invention. Accordingly, induction or supression of any biosythetic or metabolic genes in sugarcane, such as those exemplified herein, is to be considered within the scope of the present invention. Reference to a biosynthetic or metabolic gene also includes a regulatory gene.

The application of a plant as a bioreactor may be affected by the introduction of a new biosynthetic or metabolic pathway into the plant, or the reirection of metabolic flux down a pathway in a plant. For the purposes of the present invention, "introduction of a new biosynthetic or metabolic pathway" encompasses where the introduced pathway is a single protein or enzyme, which may in itself be the end-product. For example, the introduction of a nucleic acid molecule, whether or not it encodes a protein of interest, would fall within the scope of the subject invention. In this regard, a "protein" includes a protein, polypeptide or peptide as well as a glycoprotein, phosphoprotein or phospholipoprotein. Alternatively, the invention also contemplates the introduction of one or more enzymes or proteins, wherein the introduced enzyme or protein catalyses one or more reactions in the synthesis of the product of interest. For example, inplanta synthesis of vanillin could be introduced to sugarcane by the introduction of the enzymes feruloyl-CoA synthetase and enoyl-CoA hydratase.

Typically, the production of one or more metabolites or heterologous proteins, polypeptides or peptides in a plant is achieved by expression of a nucleic acid molecule encoding the protein, polypeptide or peptide of interest. Any nucleic acid which encodes a protein, polypeptide or peptide of interest is contemplated by the present invention. However, preferred nucleic acids include those encoding:

(i) vanillin biosynthetic enzymes, including 3-dehydroshilimate dehydratase, catechol-o-methyltransferase, aryl aldehyde dehydrogenase, feruloyl-CoA synthetase, enoyl-CoA hydratase/aldolase;

(ii) sorbitol biosynthetic enzymes, including glucose/fructose oxidoreductase;

(iii) PHA biosynthetic enzymes, including 3-ketothiolase, acetoacetyl-CoA reductase, PHA synthase, enoyl hydratase, 3-hydroxyacyl-acyl carrier protein:CoA tranferase;

(iv) indigo biosynthetic enzymes, including tryptophanase, L-tryptophan indole lyase, napthalene dioxygenase, *R. eutrophica* bec gene product;

(v) fructan biosynthetic enzymes, including fructosyltransferases and levansucrases;

(vi) lactic acid biosynthetic enzymes, including lactate dehydrogenase;

(vii) adipic acid biosynthetic enzymes, including 3-dehydroshikimate dehydratase, protocatechuate decarboxylase and catechol 1,2-dioxygenase;

(viii) petroselinic acid biosynthetic emzymes, including 3-ketoacyl-ACP synthase;

(ix) 1,3-propanediol biosynthetic enzymes including glycerol dehydratase, 1,3-propanediol oxidoreductase, glycerol-3-phosphate dehydrogenase, and glycerol-3-phosphatase; and/or (x) 2-phenylethanol biosynthetic enzymes including aromatic-L-amino acid decarboxylase, 2-phenylethylamine oxidase and aryl alcohol dehydrogenase.

(xi) pHBA biosynthetic enzymes including 4-hydroxycinnamoyl hydratase/lyase and chorismate pyruvate lyase.

Nucleic acids encoding a particular protein or enzyme may be chemically synthesised or isolated from another organism. In a preferred embodiment of the present invention, the gene encoding a protein or enzyme of interest is isolated from bacteria, fungi, animals, plants, protists or archaea. Bacteria provide a convenient source of genes encoding useful enzymes and proteins, although the present invention should not be limited by the source of the gene encoding the protein or enzyme of interest. Particularly useful microorganisms for the isolation of useful genes in the context of the present invention include: *R. eutropha, Aeromonas* spp., *Pseudomonas aeruginosa, Rhodococcus ruber, Nocardia corallina, Zymomonas mobilis, Enterobacter aerogenes, Pseudomonas putida, Bacillus subtilis, Klebsiella pneumoniae, Acinetobacter calcoaceticus* the actinomycetes (particularly *Streptomyces* spp.), *Escherichia coli* and yeast such as *Saccharomyces cereviseae*. However, it should be noted that these microorganisms represent only examples of the possible source of a gene encoding a protein or enzyme of interest, and the present invention is in no way limited by the source of the nucleic acid encoding the protein or enzyme of interest. Furthermore, as indicated above, the nucleic acid molecule may not necessarily encode an enzyme or protein but may encode a sense RNA or an antisense RNA, for use in gene silencing for example.

In order to maximise transcription, and/or transcript stability and/or translation and/or post-translational stability of the gene product of a heterologous gene in a plant, particularly a gene from a bacterium, it may be necessary to alter the sequence of the gene. For example, to maximise translation of the gene transcript, it may be necessary to alter the coding sequence of the gene to reflect the preferred codon usage of the host plant. Similarly, to maximise translation of the gene transcript it may be necessary to alter the sequence context of the gene's translation initiation site to reflect the preferred sequence context recognised by the host's translational machinery. Similarly, it may be necessary to add 5' and/or 3' non-translated regions to the coding sequence of the gene to maximise transcript stability within the host cell. Similarly, it may be necessary to alter the coding sequence of the gene to remove cryptic protease-recognition sites. Therefore, the present invention encompasses genes isolated from a bacterial, fungal, animal, protist or archaeal source, which have undergone modification to maximise transcription, and/or transcript stability, and/or translation, and or post-translational stability in a plant host. Other methods for the alteration of the sequence of a gene will be readily ascertained by those of skill in the art and need not be elaborated further here.

In a preferred embodiment of the present invention, a number of products may be produced according to any of a number of methods including those herein described. Examples of compounds that may be produced via metabolic engineering of a subject plant include: vanillin (4-hydroxy-3-methoxybenzaldehyde); sorbitol; PHAs; indigo; fructan; lactic acid (2-hydroxypropanoic Acid); adipic acid; 1,3 propanediol and 2-phenylethanol. These compounds, however, are only examplary, and the present invention is predicated on the use of C4 plants as bioreactors for any compound that can be synthesised in the plant Accordingly, the present invention is not limited to any one product or method for producing the product.

In a preferred embodiment of the present invention, the plant selected is a C4 grass and the product of interest is a mixture of different chain length polymers of hydroxyalkanoic acid monomers. The present invention extends, however, to the use of C4 grasses as bioreactors to generate a range of compounds such as therapeutics, nutrapharmaceuticals and diagnostic agents such as single chain antibodies.

Accordingly, the present invention contemplates a method for accumulating polymers comprising one or more species of hydroxyalkanoic acid monomer in a C4 grass, said method comprising expressing one or more genetic sequences which encode enzymes required for the production of the polymers or a homolog or precursor thereof in a cell of a C4 grass such that PHA polymers accumulate in the cytosol, storage vacuole, peroxisome and ontologically related organelles, or plastid or non-plastid organelles of said cell.

Polyhydroxyalkanoates (PHAs) are polyesters of one or more species of hydroxyalkanoic acid monomers. PHAs, which are bacterial carbon-storage polymers analogous to starch in plants and glycogen in animals, are a diverse class of compounds, with over 100 different hydroxyalkanoic acid sidechains identified to date. For example, PHB is a polymer of 3-hydroxybutyrate, and PHV is a polymer of hydroxyvalerate. PHAs can also be co-polymers, for example, poly-(3-hydroxybutyrate-co-3-hydroxyvalerate). As defined herein, therefore, "polymers comprising one or more species of hydroxyalkanoic acid monomer" and "PHAs" are synonymous and encompass any such carbon-storage polymer.

PHAs are polymers that share many properties with petrochemicallyderived, synthetic polymers. The main advantages of PHAs over synthetic polymers are that they are readily biodegradable and are made from renewable resources such as sugars and fatty acids.

While different bacterial species have developed different mechanisms for PHA biosynthesis, 3-hydroxyacylCoA is the precursor for them all. FIG. 1 outlines four different strategies utilised by a wide range of bacteria including, for example, *R. eutropha, Aeromonas* spp., *Pseudomonas aeruginosa, Rhodococcus ruber* and *Nocardia corallina*, to synthesize their requirements of polymers of 3-hydroxy acids as an energy source. Precursors may be generated by sugar glycolysis (strategy I), from metabolic intermediates of the β-oxidative (strategy II) and biosynthetic fatty acid (strategy II) pathways and from metabolites in other pathways such as the methylmalonyl-CoA pathway (strategy IV).

Figure 2:
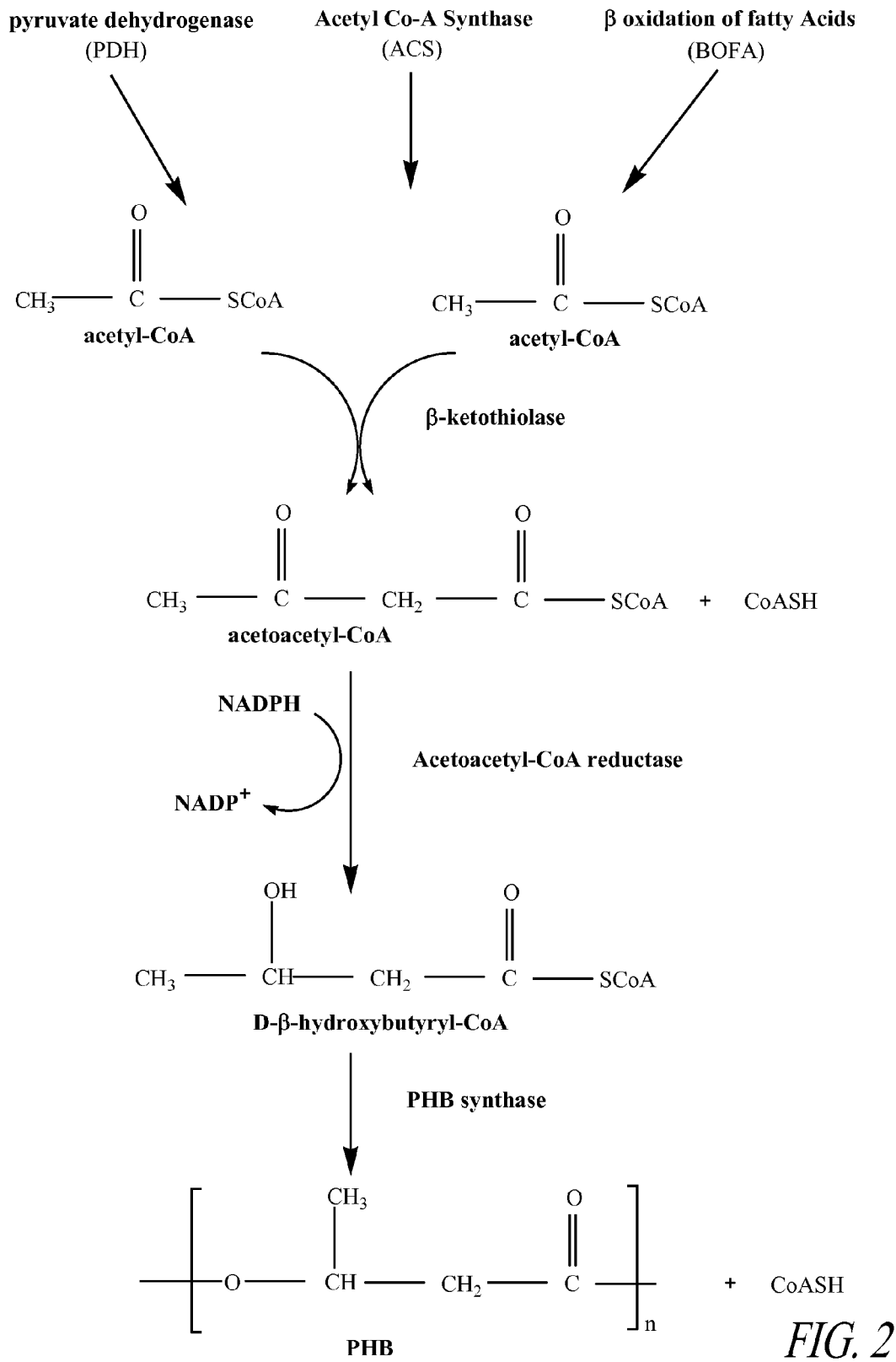
FIG. 2 is a diagrammatic representation of the biosynthetic pathway of PHB in the bacterium $R.$ $eutropha$. This pathway comprises three steps catalyzed, respectively, by three enzymes: first, two molecules of acetyl-CoA are condensed to acetoacetyl-CoA by 3-ketothiolase (encoded by phaA); secondly, acetoacetyl-CoA is reduced to D-3-hydroxybutyryl-CoA by acetoacetyl-CoA reductase (phaB); and thirdly, D-3-hydroxy-butyryl-CoA is polymerized to PHB by PHB synthase (phaC).

In the bacterium *R. eutropha*, for example, strategy I is used and the PHB biosynthetic pathway consists of three steps catalyzed by three enzymes, respectively: first, two molecules of acetyl CoA are condensed to acetoacetyl-CoA by 3-ketothiolase (encoded by phaA); secondly, aceotacetyl-CoA is reduced to D-3-hydroxybutyryl-CoA by acetoacetyl-CoA reductase (encoded by phaB); and thirdly, D-3-hydroxybutyryl-CoA is polymerized into PHB by PHB synthase (encoded by phaC). The genes are clustered in a single operon in the order pha-CAB A diagrammatic representation of this particular biosynthetic pathway is provided in FIG. 2.

*Aeromonas* spp. are examples of organisms that employ strategy II. They express a (R)-specific enoyl hydratase (PhaJ). This enzyme catalyzes the formation of 3-hydroxyacyl-CoA from enoyl-CoA intermediates in β-oxidation of fatty acids, thereby generating substrates for the polymerase. Alternatively, organisms like *P. aeruginosa* produce PHAs from intermediates in the de novo fatty acid biosynthetic pathway (strategy III). A 3hydroxyacyl-acyl carrier protein: CoA transferase enzyme designated PhaG converts 3-hydroxyacyl-acyl carrier protein to its CoA analog. The hydroxyacyl-CoA is then incorporated into the nascent polymer. Finally, organisms such as *R. ruber* and *N. corallina* are able to generate precursors for PHA production from the methylmalonly-CoA pathway (strategy IV).

Many other micro-organisms have developed alternative biosynthetic pathways for the manufacture of PHAs, including PHB, to meet their energy-requiring needs. Biosynthetic genes from almost 40 different organisms have been cloned. Only limited homologies are exhibited at both the nucleotide and amino acid levels, which is not surprising considering the large number of PHAs naturally produced by bacteria. The structural organisation of loci encoding PHA genes is equally diverse.

Any one or more or a combination of these systems may be adapted to provide suitable genetic sequences for use in accordance with the present invention. Consequently, genetic sequences which "encode enzymes required for the production of polymers" of hydroxyalkanoic acids as used herein in the context of the present invention may comprise a combination of one or more of any sequence wherein the enzyme or enzymes thereby encoded usually operate in vivo singly or together to effect the biosynthesis of PHAs, including PHB.

Preferred suitable genetic sequences comprise a combination of one or more of phaA, phaB, phaC, phaC1, phaG, phaJ. These genes encode enzyme products referred to herein as PhaA, PhaB and PhaC, PhaC1, PhaG and PhaJ.

In one preferred embodiment, the C4 grass is engineered to express one or more of phaA, phaB and phaC such that it does not accumulate the PHAs in the plastid. In another preferred embodiment, the plant is engineered to express, in addition, one or more of phaC1, phaG and phaJ, such that it accumulates the PHAs in the plastid.

The nucleotide sequences encoding phaA, phaB and phaC may come from any suitable source but the genes from *R. eutrophia* are particularly useful in the practice of the present invention. The nucleotide sequences for these genes are given in SEQ ID NO:1 (phaA), SEQ ID NO:4 (phaB) and SEQ ID NO:7 (phaC) where the nucleotide sequence does not include a signal sequence and, hence, the products, i.e. PhaA, PhaB and PhaC, respectively, are located in the cytosol.

Nucleotide sequences of phaA, phaB and phaC with a signal sequence to direct the products to the plastid are shown in SEQ ID NO:10, SEQ ID NO:13 and SEQ ID NO:16, respectively.

The nucleotide sequences encoding phaC1, phaG and phaJ may likewise come from any suitable source. In the case of phaC1, *P. aeruginosa* provides a suitable source. Nucleotide sequences encoding phaG and phaJ may be derived from, for example, *Pseudomonas putida* and *Aeromonas caviae*, respectively. The nucleotide sequence of phaC1 is given in SEQ ID NO:19, where the nucleotide sequence does not include a signal sequence and, hence, the product, i.e. PhaC1 is located in the cytosol.

Nucleotide sequences of phaC1, phaG and phaJ with a signal sequence to direct the products to the peroxisome and plastid (phaC1), and to the plastid (phaG) and peroxisome (phaJ), respectively, are shown in SEQ ID NO:22 and SEQ ID NO:25 and SEQ ID NO:28 and SEQ ID NO:31, respectively.

Clearly, the genetic sequences may be modified to insert any leader or tail sequence to direct the enzyme to an appropriate location in the cell.

Another aspect of the present invention contemplates a method for producing PHAs in a C4 grass, said method comprising expressing one or more genetic sequences comprising phaA, phaB, phaC, phaC1, phaG and/or phaJ or a derivative or homolog of any one of these in cells of a C4 grass such that polymers of a PHA accumulate in the cytosol, storage vacuole, plastid or non-plastid organelle of said cell.

Where accumulation is in the cytosol, the PHA is preferably a PHB.

A homolog of a phaA, phaB, phaC, phaC1, phaG and phaJ includes nucleotide sequences having at least about 60% identity to one of SEQ ID NO:1, SEQ ID NO:4, SEQ ID NO:7, SEQ ID NO:19, SEQ ID NO:28 or SEQ ID NO:31 (or one of SEQ ID NO:10, SEQ ID NO:13, SEQ ID NO:16, SEQ ID NO:22 or SEQ ID NO:25) after optimal alignment or nucleotide sequences capable of hybridizing to SEQ ID NO:1, SEQ ID NO:4, SEQ ID NO:7, SEQ ID NO:19, SEQ ID NO:28, SEQ ID NO:31, SEQ ID NO:10, SEQ ID NO:13, SEQ ID NO:16, SEQ ID NO: 22 or SEQ ID NO:25 or their complementary forms under low stringency conditions.

Alternatively, or in addition, a homolog at the amino acid level includes an enzyme having an amino acid sequence with at least about 60% identity to SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29 or SEQ ID NO:32.

Preferably, percentage similarities include at least about 70%, at least about 80%, at least about 90% and at least about 95% or above at the nucleotide and amino acid sequence levels such as 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100%.

Accordingly, reference herein to phaA, phaB, phaC phaC1, phaG, phaJ or PhaA, PhaB, PhaC, PhaC1, PhaG and PhaJ includes all homologs thereof.

In another embodiment, the present invention contemplates a method for generating a plant which produces PHAs, said method comprising introducing into cells of said plant a genetic sequence comprising:
  (i) a nucleotide sequence encoding a phaA or homolog thereof;
  (ii) a nucleotide sequence encoding phaB or homolog thereof;
  (iii) a nucleotide sequence encoding phaC or homolog thereof;

(iv) a nucleotide sequence encoding phaC1 or homolog thereof;

(v) a nucleotide sequence encoding phaG or homolog thereof;

(vi) a nucleotide sequence encoding phaJ or homolog thereof (vii) SEQ ID NO:1 or SEQ ID NO:3 or SEQ ID NO:10 or SEQ ID NO:12 or a nucleotide sequence having at least 60% identity thereto after optimal alignment, or capable of hybridizing to SEQ ID NO:1 or SEQ ID NO:3 or SEQ ID NO:10 or SEQ ID NO:12 or a complementary form thereof under low stringency conditions;

(viii) SEQ ID NO:4 or SEQ ID NO:6 or SEQ ID NO:13 or SEQ ID NO:15 or a nucleotide sequence having at least 60% identity thereto after optimal alignment, or capable of hybridizing to SEQ ID NO:4 or SEQ ID NO:6 or SEQ ID NO:13 or SEQ ID NO:15 or a complementary form thereof under low stringency conditions;

(ix) SEQ ID NO:7 or SEQ ID NO:9 or SEQ ID NO:16 or SEQ ID NO:18 or a nucleotide sequence having at least 60% identity thereto after optimal alignment, or capable of hybridizing to SEQ ID NO:7 or SEQ ID NO:9 or SEQ ID NO:16 or SEQ ID NO:18 or a complementary form thereof under low stringency conditions;

(x) SEQ ID NO:19 or SEQ ID NO:21 or SEQ ID NO:22 or SEQ ID NO:24 or SEQ ID NO:25 or SEQ ID NO:27 or a nucleotide sequence having at least 60% identity thereto after optimal alignment, or capable of hybridizing to SEQ ID NO:19 or SEQ ID NO:21 or SEQ ID NO:22 or SEQ ID NO:24 or SEQ ID NO:25 or SEQ ID NO:27 or a complementary form thereof under low stringency conditions;

(xi) SEQ ID NO:28 or SEQ ID NO:30 or a nucleotide sequence having at least 60% identity thereto after optimal alignment, or capable of hybridizing to SEQ ID NO:28 or SEQ ID NO:30 or a complementary form thereof under low stringency conditions;

(xii) SEQ ID NO:31 or SEQ ID NO:33 or a nucleotide sequence having at least 60% identity thereto after optimal alignment, or capable of hybridizing to SEQ ID NO:31 or SEQ ID NO:33 or a complementary form thereof under low stringency conditions;

and then regenerating a plant from said cells.

Preferably, the plant is a C4 grass and, in a particularly preferred embodiment, a sucrose-storing monocotyledonous plant. This aspect of the present invention includes progeny of the first generation plants.

A convenient C4 grass for use in the present invention is sugarcane. Sugarcane has certain advantages which make it a useful crop for use as a bioreactor including, inter alia, its efficient carbon fixation, high biomass accumulation, rapid growth in subtropical and tropical climates, natural ability to accumulate large quantities of sucrose, hardiness, and ease of growth. In addition, a micropropagation system is already available and an extensive industry infrastructure exists.

In order that PHAs may be produced in cells of a C4 grass, suitable sequences such as those derived from *R. eutropha* must be introduced into and expressed in the cells. That is, the plant needs to undergo genetic modification so that the metabolites and/or metabolic and/or biosynthetic pathways can be harnessed for the production of the PHAs. This may conveniently be achieved through the use of genetic constructs, engineered to comprise nucleotide sequences required to effect PHA production.

In another preferred embodiment of the present invention, the plant selected is a C4 grass and the product of interest is pHBA . . .

In another preferred embodiment of the present invention, the plant selected is a C4 grass and the product of interest is vanillin.

Vanillin (4-hydroxy-3-methoxybenzaldehyde) may be produced as a co-product with sucrose in sugarcane. A number of biological pathways have been discovered for the biosynthesis/biodegradation of vanillin. At least 2 of these have substrates which are available in plants, viz:

(i) 3-dehydroshikimic acid is a compound which is produced as an intermediate in the shikimate pathway. A pathway has been determined which converts this substrate via 3-dehydroshikimate dehydratase to protocatechuic acid then to vanillic acid via catechol-o-methyltransferase and finally to vanillin via aryl aldehyde dehydrogenase.

(ii) Ferulic acid is a secondary metabolite of the phenylpropanoid pathway involved in lignin synthesis. It is converted in planta to feruloyl-CoA by feruloyl-CoA synthetase which in turn is converted to vanillin by enoyl-CoA hydratase/aldolase.

Accordingly, the present invention further contemplates a method for producing vanillin in a C4 grass, said method comprising expressing one or more genetic sequences which encode enzymes required for the production of vanillin, or a homolog or precursor thereof in a cell of a C4 grass such that the vanillin accumulates in the cytosol, storage vacuole, plastid or non-plastid organelle, or is extra-cellularly secreted.

Either of these pathways, or a combination of these pathways, may be adapted to provide suitable genetic sequences for use in the production of vanillin or precursors thereof in Sugarcane. Consequently, genetic sequences which "encode enzymes required for the production of vanillin" as used herein in the context of the present invention may comprise a combination of one or more of any sequence wherein the enzyme or enzymes thereby encoded usually operate in vivo singly or together to effect the biosynthesis of vanillin or a precursor thereof.

Clearly, the genetic sequences may be modified to insert any leader or tail sequence to direct the enzyme to an appropriate location in the cell.

Another aspect of the present invention contemplates a method for producing Vanillin in a C4 grass, said method comprising expressing one or more genetic sequences encoding 3-dehydroshikimate dehydratase, catechol-o-methyltransferase, aryl aldehyde dehydrogenase, feruloyl-CoA synthetase, enoyl-CoA hydratase and/or enoyl-CoA aldolase, in cells of a C4 grass such that vanillin accumulates anywhere in the cell or extra-cellular matrix of the plant.

Accordingly, reference herein to 3-dehydroshilkimate dehydratase, catechol-o-methyltransferase, aryl aldehyde dehydrogenase, feruloyl-CoA synthetase, enoyl-CoA hydratase and/or enoyl-CoA aldolase, includes all homologs thereof.

In another embodiment, the present invention provides a method for generating a plant which produces vanillin or a precursor thereof, said method comprising introducing into cells of said plant a genetic sequence comprising at least one of the following:

(i) a nucleotide sequence encoding a 3-dehydroshikimate dehydratase and/or;

(ii) a nucleotide sequence encoding catechol-o-methyltransferase;

(iii) a nucleotide sequence encoding aryl aldehyde dehydrogenase;

(iv) a nucleotide sequence encoding feruloyl-CoA synthetase;
(v) a nucleotide sequence encoding enoyl-CoA hydratase
(vi) a nucleotide sequence encoding enoyl-CoA aldolase;
(vii) a nucleotide sequence encoding a homolog of any one of (i) though (vi)

and then regenerating a plant from said cells.

Preferably, the plant is a C4 grass and, in a particularly preferred embodiment, sugarcane. Included in this aspect of the present invention are progeny of the first generation plants.

In order that Vanillin may be produced in cells of a C4 grass, suitable sequences such as those encoding one or more Vanillin biosynthetic enzymes must be introduced into and expressed in the cells. That is, the plant needs to undergo genetic modification so that the metabolites and/or metabolic and/or biosynthetic pathways can be harnessed for the production of the vanillin or a precursor thereof. This may conveniently be achieved through the use of genetic constructs, engineered to comprise nucleotide sequences required to effect vanillin production.

In another preferred embodiment of the present invention, the plant selected is a C4 grass and the product of interest is sorbitol.

Sorbitol is a polyol that is found naturally in many fruits. To satisfy the high demand for this compound it is synthesized industrially by hydrogenation of corn-derived glucose in aqueous solution using nickel-containing catalysts. The majority of the sorbitol produced is consumed in the manufacture of toothpaste, confectionary, and ascorbic acid.

A new market for sorbitol in the polymer sector has been described by industry. Isosorbide or 1,4-3,6-dianhydrosorbitol is produced by the acid catalyzed dehydration of sorbitol. Recent patents have demonstrated that copolymers of isosorbide and polyethylene terephthalate (PET) exhibit superior strength and rigidity compared to PET alone. 4.4 billion lb of PET is currently used in food and beverage containers (Source: US Dept. Energy, 2001). Replacing PET with the isosorbide-PET copolymer (sPET) would reduce the overall consumption of petroleum-derived PET because less sPET is needed to achieve the equivalent strength. The projected sPET production is 1 billion lb per year by 2020, utilizing 100 million lb of isosorbide (Source: US Dept. Energy) 2001).

Sorbitol is already produced from a renewable feedstock. The main incentive to use sugarcane as a sorbitol biofactory is to capitalize upon a potential future demand for this product by the plastics industry.

Sorbitol can also be converted to other useful chemicals. Propylene glycol, ethylene glycol, and glycerol can be derived from catalytic hydrogenolysis of sorbitol. These chemical feedstocks are currently derived from petrochemicals.

The biosynthesis of sorbitol produces the coproduct gluconolactone. The enzyme glucono-δ-lactonase can convert the gluconolactone into gluconic acid. Gluconic acid is used as a food acidulant, antioxidant, and a clarifier in wines and softdrinks.

*Zymomonas mobilis* is able to produce sorbitol from sucrose or a mixture of glucose and fructose in a one-step reaction catalysed by the glucose-fructose oxidoreductase GFOR (Genbank accession no. Z80356, M97379). The glucose is oxidized to gluconolactone while the fructose is reduced to sorbitol.

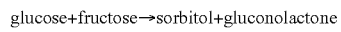

glucose+fructose→sorbitol+gluconolactone

Without limiting the present invention to any one method or mode of action, sorbitol production in sugarcane could be achieved by using GFOR. This involves constructing an expression cassette by fusing GFOR to the maize polyubiquitin promoter and nopaline synthase terminator and introducing the cassette into sugarcane callus by biolistic transformaton. The *Z. mobilis* GFOR is not membrane-bound and resides in the periplasm and should work equally well as a cytosolic enzyme in sugarcane.

Sorbitol production is unlikely to be toxic in sugarcane since sorbitol is found in numerous fruits (apples, pears, plums, berries, cherries). Sorbitol functions physiologically to regulate osmotic stress hence extremely high levels may be detrimental and vacuolar storage may circumvent this problem.

Accordingly, the present invention further contemplates a method for producing sorbitol in a C4 grass, said method comprising expressing one or more genetic sequences which encode enzymes required for the production of sorbitol, or a homolog or precursor thereof in a cell of a C4 grass such that the sorbitol accumulates in the cytosol, storage vacuole, plastid or non-plastid organelle, or is secreted extra-cellularly.

In addition to the glucose-fructose oxidoreductase pathway, other nucleotide sequences may encode other enzymes suitable for use in the production of sorbitol or precursors thereof in Sugarcane. Consequently, genetic sequences which "encode enzymes required for the production of sorbitol" as used herein in the context of the present invention may comprise a combination of one or more of any sequence wherein the enzyme or enzymes thereby encoded usually operate in vivo singly or together to effect the biosynthesis of sorbitol or a precursor thereof.

Clearly, the genetic sequences may be modified to insert any leader or tail sequence to direct the enzyme to an appropriate location in the cell.

Another aspect of the present invention contemplates a method for producing sorbitol in a C4 grass, said method comprising expressing one or more genetic sequences encoding a glucose-fructose oxidoreductase or homolog thereof, in cells of a C4 grass such that sorbitol accumulates anywhere in the cell or extra-cellular matrix of the plant.

In a preferred embodiment, the glucose-fructose oxidoreductase is that encoded by the nucleic acid sequence set forth in Genbank accession number Z80356 or M97379, or a nucleotide sequence having at least 60% identity thereto after optimal alignment, or capable of hybridizing to these sequences under low stringency conditions.

Accordingly, reference herein to glucose-fructose oxidoreductase, includes all homologs thereof.

In another embodiment, the present invention contemplates a method for generating a plant which produces sorbitol or a precursor thereof, said method comprising introducing into cells of said plant a genetic sequence comprising a nucleotide sequence encoding a glucose-fructose oxidoreductase or homolog thereof and then regenerating a plant from said cells.

Preferably, the plant is a C4 grass and, in a particularly preferred embodiment, sugarcane.

In order that sorbitol may be produced in cells of a C4 grass, suitable sequences such as those encoding one or more sorbitol biosynthetic enzymes must be introduced into and expressed in the cells. That is, the plant needs to undergo genetic modification so that the metabolites and/or metabolic and/or biosynthetic pathways can be harnessed for the production of the sorbitol or a precursor thereof. This may conveniently be achieved through the use of genetic constructs, engineered to comprise nucleotide sequences required to effect sorbitol production.

Clearly, the genetic sequences may be modified to insert any leader, tail or signal sequences to direct the enzyme to an appropriate location in the cell.

In another preferred embodiment of the present invention, the plant selected is a C4 grass and the product of interest is indigo.

Until the end of the 19th century, the sole source of indigo was from plants, woad (*Isatis tinctoria*) and Dyer's Knotweed (*Polygonum tinctorum*) in temperate climates and *Indigofera* species in the tropics. Woad was widely grown in Europe, making some regions, especially Toulouse (France) and Erfurt (Germany), very wealthy until the end of the 16th century.

Plant-based indigo was almost entirely replaced in the 20th century by synthetic indigo. Today indigo is still regarded as a high value specialty chemical used mainly as a dye in the textile industry. It is produced synthetically from naphthalene by the Heumann synthesis reaction.

The chief incentive to use sugarcane as an indigo biofactory is to provide a manufacturing route that will produce relatively inexpensive indigo from a renewable feedstock.

Indigo production by microbial fermentation has been demonstrated by expressing the genes that mediate indigo formation in *E. coli*. The pigment is derived by converting endogenous tryptophan to indole using the *Enterobacter aerogenes* tryptophanase or L-tryptophan indole lyase EC 4.1.99.1 (Genbank accession no. D14297). Subsequently the indole is converted to indigo via two possible reactions.

Route A: *Pseudomonas putida* napthalene dioxygenase (Genbank accession no. M83949)

Route B: *Ralstonia eutropha* bec gene (Genbank accession no. AF306552)

Figure 8:
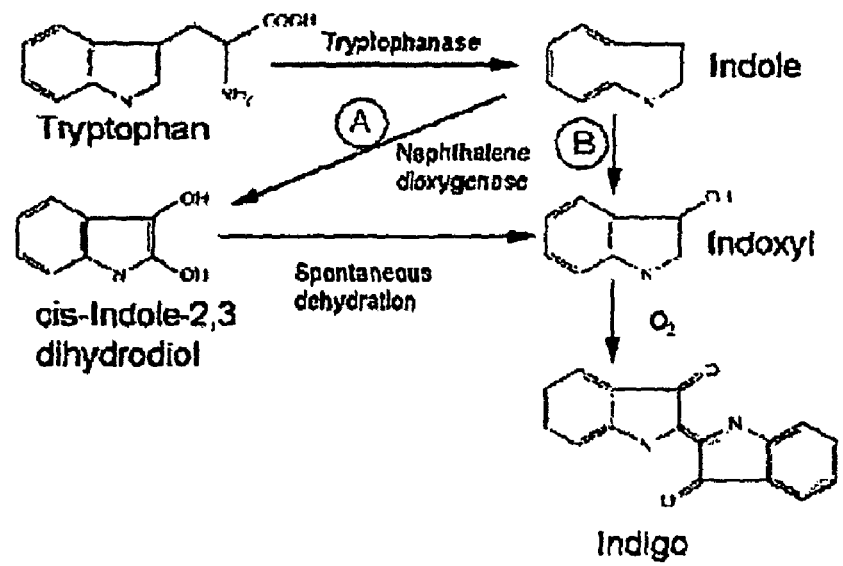
FIG. 8 is a graphical representation showing the indigo biosynthetic pathway.
Figure 9:
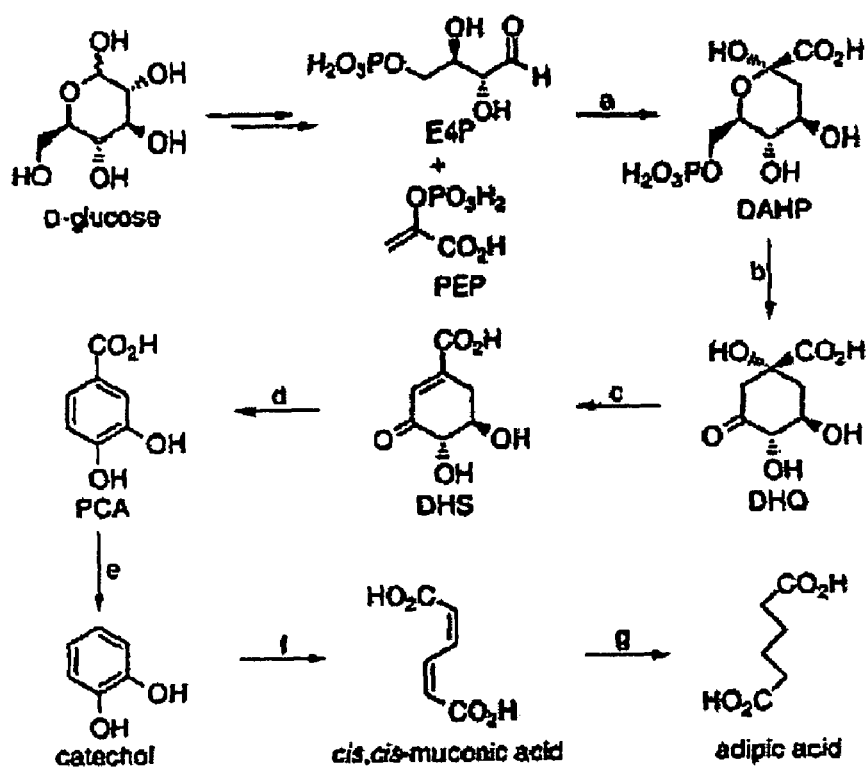
FIG. 9 is a graphical representation showing adipic acid biosynthesis from glucose via a cis, cis-muconic acid intermediate. d=3-dehydroshikimate dehydratase, e=protochatechuate decarboxylase, f=catechol-1,2-dioxygenase.

These pathways are graphically depicted in FIG. 8.

Without limiting the present invention to any one method or mode of action, indigo production in sugarcane involves constructing an expression cassette by fusing the aforementioned genes to the maize polyubiquitin promoter and nopaline synthase terminator and introducing the cassette into sugarcane callus by biolistic transformaton. Tryptophan is a product of the plant shikimate pathway, which is responsible for synthesizing lignin precursors. The cloned genes may be plastid-targeted since the shikimate pathway reactions reside in this compartment. The available metabolic flux in this pathway is expected to be significant.

Aeration of the sugarcane juice will lead to spontaneous oxidation of indoxyl to an insoluble indigo precipitate. The solid precipitate should be easy to separate from the solution by filtration or centrifugation.

Another aspect of the present invention contemplates a method for producing indigo in a C4 grass, said method comprising expressing one or more genetic sequences encoding tryptophanase, L-tryptophan indole lyase, napthalene dioxygenase, and/or the *Ralstonia eutropha* bec gene, or homolgs thereof, in cells of a C4 grass such that indigo accumulates anywhere in the cell or extracellular matrix of the plant In a preferred embodiment, indigo accumulates in the plastid of the plant cell.

Accordingly, reference herein to genetic sequences encoding tryptophanase, L-tryptophan indole lyase, napthalene dioxygenase, and/or the *Ralstonia eutropha* bec gene includes all homologs thereof.

In another embodiment, the present invention contemplates a method for generating a plant which produces indigo or a precursor thereof, said method comprising introducing into cells of said plant a genetic sequence comprising at least one of the following:

(i) a nucleotide sequence encoding genetic sequences encoding tryptophanase;

(ii) a nucleotide sequence encoding L-tryptophan indole lyase;

(iii) a nucleotide sequence encoding napthalene dioxygenase;

(iv) a nucleotide sequence comprising the *Ralstonia eutropha* bec gene;

(v) the nucleotide sequence set forth in Genbank accession number D14279, or a nucleotide sequence having at least 60% identity thereto after optimal alignment, or capable of hybridizing to Genbank D14279 under low stringency conditions.

(vi) the nucleotide sequence set forth in Genbank accession number M83949, or a nucleotide sequence having at least 60% identity thereto after optimal alignment, or capable of hybridizing to Genbank M83949 under low stringency conditions.

(vii) the nucleotide sequence set forth in Genbank accession number AF306552, or a nucleotide sequence having at least 60% identity thereto after optimal alignment, or capable of hybridizing to Genbank AF306552 under low stringency conditions.

and then regenerating a plant from said cells.

Preferably, the plant is a C4 grass and, in a particularly preferred embodiment, sugarcane.

In order that indigo may be produced in cells of a C4 grass, suitable sequences such as those encoding one or more indigo biosynthetic enzymes must be introduced into and expressed in the cells. That is, the plant needs to undergo genetic modification so that the metabolites and/or metabolic and/or biosynthetic pathways can be harnessed for the production of the indigo or a precursor thereof. This may conveniently be achieved through the use of genetic constructs, engineered to comprise nucleotide sequences required to effect indigo production.

Clearly, the genetic sequences may be modified to insert any leader or tail sequence to direct the enzyme to an appropriate location in the cell. In a preferred embodiment the leader, tail or signal sequence directs the indigo biosynthetic enzyme to be localized in the plastid.

In another preferred embodiment of the present invention, the plant selected is a C4 grass and the product of interest is a mixture of different chain length polymers of fructose monomers, such as fructans.

Fructan, or levan as it is often called, is a fructose homopolysaccharide that is linked to a terminal glucose residue. Fructans are a storage carbohydrate in some plants such as Jerusalem artichoke and chicory. Certain bacilli can also synthesize fructans.

Despite a plethora of potential applications, this polymer is not yet widely used. Some of the possible uses cited by the literature are:

(i) Low calorie sweetener. Fructans possess a sweet taste but cannot be degraded in humans.

(ii) Dietary fibre (iii) Bulking agent (iv) Raw material for biodegradable plastics, detergents, and adhesives Fructans may also be an inexpensive source of fructose in the future. The food industry is rapidly adopting fructose as the preferred sweetener over sucrose. Fructose may be up to 1.8 times sweeter than sucrose. Consequently, less fructose is needed to derive the same effect. Fructose syrup is presently obtained by hydrolysis of starch to glucose followed by enzymatic isomerization of glucose to fructose. The resultant solution is an equilibrium mixture of glucose/fructose that must be further purified by ion chromatography to obtain near pure fructose. This final step purportedly adds significantly to the cost of fructose manufacture. It would be possible to avoid this step if the starting material contained only fructose. Simple hydrolysis of fructans will yield pure fructose at a reduced cost compared with using starch as the raw material.

Incentives to use sugarcane as fructan biofactory include:
(i) To create a market for this product. A demand for fructans would develop if sufficient amounts were made available. The disadvantage of the existing fructan flora is the low harvestable weight per plant.
(ii) To provide an alternative and inexpensive route for fructose production.
(iii) In subtropical and tropical climates sugarcane exhibits fast growth and very high biomass yields. The high rate of $CO_2$ fixation due to C4 photosynthesis should facilitate a rapid accumulation of fructans.
(iv) Vegetative propagation ensures a stable germplasm and hence predictable product yields.

Naturally occurring fructans may contain 10 to 100,000 fructose residues. Bacteria produce the larger fructans whilst those occurring in plants are smaller. The larger polymers are desirable because they are less soluble in water and consequently easier to extract. Larger fructans will not affect the osmotic pressure in the cell to the same degree as smaller molecules. Therefore it is possible to store greater quantities of fructan before the cell is affected.

Numerous bacterial fructosyltransferases or levansucrases have been characterized such as Genbank accession no. AY150365, from *Bacillus subtilis*. These enzymes catalyze the transfer of the D-fructosyl residue from sucrose to the β-2,6-linked residues of fructan.

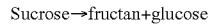

Sucrose→fructan+glucose

Without limiting the present invention to any one method or mode of action, fructan production in sugarcane would be achieved by constructing an expression cassette containing levansucrase, the maize polyubiquitin promoter and nopaline synthase terminator and introducing the cassette into sugarcane callus by biolistic transformaton.

Another aspect of the present invention contemplates a method for producing fructans in a C4 grass, said method comprising expressing one or more genetic sequences encoding a bacterial fructosyltransferase or levansucrase in cells of a C4 grass such that a fructan accumulates anywhere in the cell or extra-cellular matrix of the plant.

In a preferred embodiment, fructan accumulates in the apoplast or vacuole of the plant cell.

Accordingly, reference herein to genetic sequences encoding fructosyltransferases and levansucreases includes all homologs thereof.

In another embodiment, the present invention relates to a method for generating a C4 grass plant which produces a fructan or a precursor thereof, said method comprising introducing into cells of said plant a genetic sequence comprising at least one of the following:
(i) a nucleotide sequence encoding a fructosyltransferase or homolog thereof;
(ii) a nucleotide sequence encoding a levansucrase or homolg thereof;
(iii) the nucleotide sequence set forth in Genbank accession number AY150365, or a nucleotide sequence having at least 60% identity thereto after optimal alignment, or capable of hybridizing to Genbank AY150365 under low stringency conditions.

and then regenerating a plant from said cells.

Preferably, the plant is a C4 grass and, in a particularly preferred embodiment, sugarcane.

In order that a fructan may be produced in cells of a C4 grass, suitable sequences such as those encoding one or more indigo biosynthetic enzymes must be introduced into and expressed in the cells. That is, the plant needs to undergo genetic modification so that the metabolites and/or metabolic and/or biosynthetic pathways can be harnessed for the production of the indigo or a precursor thereof. This may conveniently be achieved through the use of genetic constructs, engineered to comprise nucleotide sequences required to effect fructan production.

Clearly, the genetic sequences may be modified to insert any leader, tail or signal sequence to direct the enzyme to an appropriate location in the cell. In a preferred embodiment, to maximise fructan production in sugarcane, levansucrase is directed to the apoplast or vacuole to maximize access to substrate for conversion.

In another preferred embodiment of the present invention, the plant selected is a C4 grass and the product of interest is lactic acid (2-Hydroxypropanoic acid).

The world market for solvent replacement, biodegradable plastics and oxygenated chemicals derived from lactic acid exceeds US$ 10 billion (Argonne National Laboratory, US DOE).

Without limiting the present invention to any one method or mode of action, lactic acid production in sugarcane involves the following general steps:
(i) Obtain or clone lactate dehydrogenase (LDH) or a homolog therof:
(ii) Express gene in sugarcane (cytosol, therefore no targeting is required)
(iii) Regenerate plants and evaluate for lactate (or derivative) production Traditionally, lactic acid purification has been a complex chemical process. However, recent advances have simplified this process and made it significantly cheaper. It is anticipated that lactic acid can be removed from the post-crushing millstream without great difficulty or extensive modification of existing structures.

Accordingly, the present invention further contemplates a method for producing lactic acid in a C4 grass, said method comprising expressing one or more genetic sequences which encode enzymes required for the production of lactic acid, or a homolog or precursor thereof in a cell of a C4 grass such that the lactic acid accumulates in the cytosol, storage vacuole, plastid or non-plastid organelle, or is secreted extra-cellularly.

Genetic sequences which "encode enzymes required for the production of lactic acid" as used herein in the context of the present invention may comprise a combination of one or more of any sequence wherein the enzyme or enzymes thereby encoded usually operate in vivo singly or together to effect the biosynthesis of lactic acid or a precursor thereof.

Clearly, the genetic sequences may be modified to insert any leader or tail sequence to direct the enzyme to an appropriate location in the cell.

In a preferred embodiment the lactate dehydrogenase nucleic acid sequence is expressed without a signal sequence such that the enzyme is active in the cytosol.

Another aspect of the present invention contemplates a method for producing lactic acid in a C4 grass, said method comprising expressing one or more genetic sequences encoding lactate dehydrogenase or a homolog thereof in cells of a C4 grass such that lactic acid accumulates anywhere in the cell or extracellular matrix of the plant.

Accordingly, reference herein to lactate dehydrogenase, includes all homologs thereof.

In another embodiment, the present invention contemplates a method for generating a plant which produces lactic acid or a precursor thereof, said method comprising introducing into cells of said plant a genetic sequence encoding lactate dehydrogenase or homolog thereof, and then regenerating a plant from said cells.

Preferably, the plant is a C4 grass and, in a particularly preferred embodiment, sugarcane.

In order that lactic acid may be produced in cells of a C4 grass, suitable sequences such as those encoding one or more lactic acid biosynthetic enzymes must be introduced into and expressed in the cells. That is, the plant needs to undergo genetic modification so that the metabolites and/or metabolic and/or biosynthetic pathways can be harnessed for the production of the lactic acid or a precursor thereof. This may conveniently be achieved through the use of genetic constructs, engineered to comprise nucleotide sequences required to effect lactic acid production.

In another preferred embodiment of the present invention, the plant selected is a C4 grass and the product of interest is adipic acid.

Adipic acid is classified as a bulk chemical and is among the top fifty chemicals produced in the US. It is principally used in the production of nylon 66, polyeurethane resins and plasticizers. Nearly 90% is used to produce nylon-6,6, a synthetic polymer developed by DuPont in the 1930's. This polyamide is formed by the condensation of adipic acid and 1,6-diaminohexane.

Adipic acid is presently produced industrially by benzene-based synthetic chemistry. Catalytic hydrogenation of benzene followed by air oxidation yields a ketone/alcohol mixture (cyclohexanone/cyclohexanol) that is further oxidized with nitric acid to produce adipic acid.

Incentives to use sugarcane as an adipic acid biofactory include:
(i) Provide a renewable feedstock for adipic acid manufacture.
(ii) Eliminate the production of the toxic nitrous oxide byproduct that accompanies traditional adipic acid synthesis.
(ii) Capitalize upon the high demand for this product.
(iv) Access to low cost molasses to produce products by fermentation.
(v) Access to low operating and infrastructure costs through co-location of an extraction facility (or fermentation facility) with a sugar mill.
(vi) In subtropical and tropical climated sugarcane exhibits fast growth and very high biomass yields. This is a prerequisite for economical bulk chemical production.
(vii) Vegetative propagation ensures a stable germplasm and hence predictable product yields.

Without limiting the present invention to any one method or mode of action, adipic acid may be produced in sugarcane by one of two approaches.

I. Synthesis from Cis, Cis-muconic Acid

Niu et al. (*Biotechnol. Prog.*, 18: 201-211, 2002) describe a microbiological route for the production of adipic acid using *E. coli*. Three genes were introduced into *E. coli* to produce cis, cis-muconic acid that was subsequently purified from the fermentation broth and converted to adipic acid by catalytic hydrogenation (step g, 10% Pt/C, $H_2$, 3400 kPa, 25° C.). This final step has a 97% conversion efficiency.

The synthesis of cis, cis-muconic acid in sugarcane involves making use of the shikimate pathway. In order to use the shikimate pathway to produce cis, cis-muconic acid the following biosynthetic enzymes, or homologs thereof are introduced into sugarcane:

*Klebsiella pneumoniae* 3-dehydroshikimate dehydratase (aroZ)-enzyme d

3-dehydroshikimate→protocatechuate

*Klebsiella pneumoniae* protocatechuate decarboxylase (aroY)-enzyme e

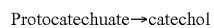

Protocatechuate→catechol

*Acinetobacter calcoaceticus* catechol 1,2-dioxygenase (catA)-enzyme f

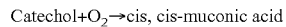

Catechol+$O_2$→cis, cis-muconic acid

Introduction of these genes into sugarcane involves constructing an expression cassette by fusing the genes described above to the maize polyubiquitin promoter and nopaline synthase terminator and introducing the cassette into sugarcane callus by biolistic transformation. Catechol is probably produced in most plants, and therefore, it may be unnecessary to clone additional copies of 3-dehydroshikimate dehydratase or protocatechuate decarboxylase. Preferrably, the cloned gene(s) are plastid-targeted since the shikimate pathway reactions reside in this compartment.

The merits of using plant secondary metabolism to synthesize interesting products have often been promoted in the literature (Verpoorte and Memelink, *Curr. Opin. Biotech.* 13: 181-187, 2002). The shikimate pathway executes a central role in plant secondary metabolism. This is one of the most active pathways in plants in terms of carbon flux owing to the fact that it is the source of lignin precursors. This makes it an attractive candidate for metabolic engineering.

II. Synthesis from Petroselinic Acid

Figure 10:
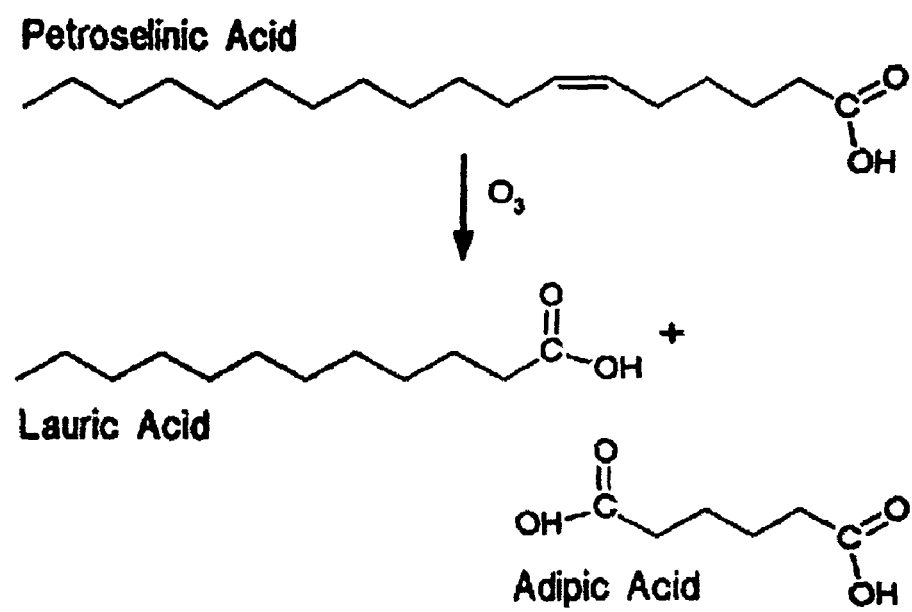
FIG. 10 is a graphical representation showing adipic acid biosynthesis by petroselinic acid ozonolysis.

Bio-based adipic acid can be obtained through ozonolysis ($O_3$) of petroselinic acid (18:1 $\Delta^{6\ cis}$), as depicted in FIG. 10. The coproduct lauric acid is also a potential source of feedstock for detergent manufacture.

The seed oil of the coriander spice plant contains 80-90% petroselinic acid. A 36 kDa putative acyl-ACP desaturase (Genbank accession no. M93115) has been identified from coriander seed extracts and the corresponding cDNA was able to confer the ability to produce petroselinic acid in tobacco callus (Cahoon et al. *Proc. Natl. Acad. Sci. USA* 89: 11184-11188, 1992).

The metabolic pathway for producing petroselinic acid is unclear, however, evidence suggests that it is formed by the desaturation of palmitoyl-ACP by the 36 kDa desaturase followed by elongation to form petroselinic acid (Cahoon and Ohlrogge, *Plant Physiol.*, 104: 827-837, 1994).

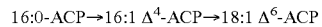

16:0-ACP→16:1 $\Delta^4$-ACP→18:1 $\Delta^6$-ACP

Recent studies have identified a 3-ketoacyl-ACP synthase (Genbank accession no. AF263992) associated with the two carbon elongation of 16:1 $\Delta^4$-ACP-(Mekhedov et al., Plant Mol. Biol. 47: 507-518, 2001).

Cis, cis-muconic acid in sugarcane juice would be converted to adipic acid by catalytic hydrogenation. The adipic acid in the resultant solution can be recovered by solvent extraction. The solution is contacted with chloroform or methylene chloride and the adipic acid recovered in the aqueous fraction. The aqueous fraction would then be evaporated to yield crystalline adipic acid.

Accordingly, the present invention further contemplates a method for producing adipic acid, or a precursor thereof such as cis, cis-muconic acid, in a C4 grass, said method comprising expressing one or more genetic sequences which encode enzymes required for the production of adipic acid and/or cis, cis-muconic acid, or a homolog or precursor thereof in a cell of a C4 grass such that adipic acid and/or cis, cis-muconic acid accumulates in the cytosol, storage vacuole, plastid or non-plastid organelle, or is secreted extra-cellularly.

Either of the hereinbefore described pathways for the production of cis, cis-muconic acid, or a combination of these pathways, may be adapted to provide suitable genetic sequences for use in the production of vanillin or precursors thereof in Sugarcane. Consequently, genetic sequences which "encode enzymes required for the production of cis, cis-muconic acid" as used herein in the context of the present invention may comprise a combination of one or more of any sequence wherein the enzyme or enzymes thereby encoded usually operate in vivo singly or together to effect the biosynthesis of cis, cis-muconic acid or a precursor thereof.

Clearly, the genetic sequences may be modified to insert any leader, tail or signal sequence to direct the enzyme to an appropriate location in the cell. Preferably the leader tail or signal sequences lead to the co-localization of the adipic acid biosynthetic enzymes with the endogenous skimimate pathway enzymes in the plant. More preferably, said enzymes are localized in the plastid.

Another aspect of the present invention contemplates a method for producing cis, cis-muconic acid or adipic acid in a C4 grass, said method comprising expressing one or more genetic sequences encoding 3-dehydroshikimate dehydratase, protochatechuate decarboxylase, catechol 1,2-dioxygenase and/or 3-ketoacyl-ACP synthase in cells of a C4 grass such that adipic acid or an adipic acid precursor accumulates anywhere in the cell or extracellular matrix of the plant.

Accordingly, reference herein to 3-dehydroshikimate dehydratase, protochatechuate decarboxylase, catechol 1,2-dioxygenase and/or 3-ketoacyl-ACP synthase, includes all homologs thereof.

In another embodiment, the present invention contemplates a method for generating a plant which produces adipic acid or a precursor thereof, said method comprising introducing into cells of said plant a genetic sequence comprising at least one of the following:

(i) a nucleotide sequence encoding a 3-dehydroshikimate dehydratase and/or;

(ii) a nucleotide sequence encoding protochatechuate decarboxylase;

(iii) a nucleotide sequence encoding catechol 1,2-dioxygenase;

(iv) a nucleotide sequence encoding 3-ketoacyl-ACP synthase; and/or (v) a nucleotide sequence encoding a homolog of any one of (i) through (iv).

and then regenerating a plant from said cells.

In a preferred embodiments:

(i) the nucleotide sequence encoding a 3-dehydroshikimate dehydatase is the aroZ gene from *Klebsiella pneumoniae*, or a homolog thereof;

(ii) the nucleotide sequence encoding a protochatechuate decarboxylase is the aroY gene from *Klebsiella pneumoniae*, or a homolog thereof;

(iii) the nucleotide sequence encoding a 1,2-dioxygenase is the catA gene from *Acinetobacter calcoaceticus*, or a homolog thereof;

(iv) the nucleotide sequence encoding a 3-ketoacyl-ACP synthase is the nucleotide sequence set forth in Genbank Accession number AF263992, or a nucleotide sequence having at least 60% identity thereto after optimal alignment; or capable of hybridizing to Genbank AF263992 under low stringency conditions.

Preferably, the plant is a C4 grass and, in a particularly preferred embodiment, sugarcane.

In order that adipic acid or a precursor thereof may be produced in cells of a C4 grass, suitable sequences such as those encoding one or more adipic acid biosynthetic enzymes must be introduced into and expressed in the cells. That is, the plant needs to undergo genetic modification so that the metabolites and/or metabolic and/or biosynthetic pathways can be harnessed for the production of adipic acid or a precursor thereof. This may conveniently be achieved through the use of genetic constructs, engineered to comprise nucleotide sequences required to effect the production of adipic acid and/or precursors thereof.

In another preferred embodiment of the present invention, the plant selected is a C4 grass and the product of interest is 1,3-propanediol (1,3-PD).

1,3-PD is a bifunctional alcohol that can be used as a monomer in numerous polycondensation reactions to produce polyesters, polyurethanes, and polyethers. The high cost of chemical synthesis, reportedly US$30/kg (Biebl et al., *Appl. Microbiol. Biotechnol.*, 52: 289-297, 1999) has restricted its use in the past to specialty markets such as dioxane production and the solvent market.

1,3-PD is synthesized using a process in which ethylene oxide is reacted with carbon dioxide and hydrogen. An alternative method, the Degussa process, is based upon hydrolysis of acrolein followed by catalytic hydrogenation. Both routes involve the use of petrochemical feedstock.

1,3-PD is a natural product of glycerol fermentation in a few enterobacteria and clostridia Incentives to use sugarcane as 1,3-PD biofactory include:

(i) Provide a renewable feedstock for 1,3-PD manufacture.

(ii) Provide a high volume, low cost source of 1,3-PD to facilitate expansion of the market.

(iii) Capitalize upon the high demand for this product.

(iv) Access to low cost molasses to produce products by fermentation.

(v) Access to low operating and infrastructure costs through co-location of an extraction facility (or fermentation facility) with a sugar mill.

(vi) In subtropical and tropical climated sugarcane exhibits fast growth and very high biomass yields. This is a prerequisite for economical bulk chemical production.

(vii) Vegetative propagation ensures a stable germplasm and hence predictable product yields.

The metabolic reactions that convert glycerol to 1,3-PD have been established from *Klebsiella pneumoniae*:

*Klebsiella pneumoniae* glycerol dehydratase (dhaB)
glycerol→3-hydroxypropionaldehyde+$H_2O$

*Klebsiella pneumoniae* 1,3-propanediol oxidoreductase (dhaT)

3-hydroxypropionaldehyde+NADH→1,3-propanediol+NAD

Sugarcane does not naturally produce glycerol therefore the reactions that convert triose phosphates to glycerol must also be engineered into sugarcane.

*Saccharomyces cerevisiae* glycerol-3-phosphate dehydrogenase dihydroxyacetone phosphate+NADH⇌glycerol-3-phosphate+NA)

*Saccharomyces cerevisiae* glycerol-3-phosphatase glycerol-3-phosphate+ADP→glycerol+ATP Without limiting the present invention to any one method or mode of action, all four new genes are cloned into sugarcane to convert it into a 1,3-PD biofactory. These genes are assembled into an expression cassette containing the maize polyubiquitin promoter and nopaline synthase terminator. The cassette is introduced into sugarcane callus by biolistic transformation and expression will be targeted to the cytosol. The accumulation of 1,3-PD in plant tissue will be assayed from plant extracts by conventional HPLC.

1,3-PD can be recovered from sugarcane juice by extraction with cyclohexane followed by vaporization of the residual solvent. Alternatively, distillation may be employed. Use of cyclohexane is environmentally unsound and distillation is energy intensive. Consequently, a method has been patented that describes the use of ion exclusion resins to recover 1,3-PD (WO0173097 Method of recovering 1,3-propanediol from fermentation broth, Archer Daniels Midland Co., 2001).

Accordingly, the present invention further contemplates a method for producing 1,3-propanediol in a C4 grass, said method comprising expressing one or more genetic sequences which encode enzymes required for the production of 1,3-propanediol, or a homolog or precursor thereof in a cell of a C4 grass such that the 1,3-propanediol accumulates in the cytosol, storage vacuole, plastid or non-plastid organelle, or is secreted extra-cellularly.

Any of the disclosed biosynthetic steps, or a combination of these, may be adapted to provide suitable genetic sequences for use in the production of 1,3-propanediol, or precursors thereof, in sugarcane. Consequently, genetic sequences which "encode enzymes required for the production of 1,3-propanediol" as used herein in the context of the present invention may comprise a combination of one or more of any sequence wherein the enzyme or enzymes thereby encoded usually operate in vivo singly or together to effect the biosynthesis of 1,3-propanediol or a precursor thereof.

Clearly, the genetic sequences may be modified to insert any leader or tail sequence to direct the enzyme to an appropriate location in the cell.

The present invention contemplates a method for producing 1,3-propanediol in a C4 grass, the method comprising expressing one or more genetic sequences encoding glycerol dehydratase, 1,3-propanediol oxidoreductase, glycerol-3-phosphate dehydrogenase and glycerol-3-phosphatase in cells of a C4 grass such that 1,3-propanediol accumulates anywhere in the cell or extra-cellular matrix of the plant.

Accordingly, reference herein to glycerol dehydratase, 1,3-propanediol oxidoreductase, glycerol-3-phosphate dehydrogenase and glycerol-3-phosphatase includes all homologs thereof.

In another aspect, the present invention contemplates a method for generating a plant which produces 1,3-propanediol or a precursor thereof, said method comprising introducing into cells of said plant a genetic sequence comprising at least one of the following:

(i) a nucleotide sequence encoding a glycerol dehydratase and/or;

(ii) a nucleotide sequence comprising the dhaB gene from *Klebsiella pneumoniae*, or a homolg thereof;

(iii) a nucleotide sequence encoding 1,3-propanediol oxidoreductase;

(iv) a nucleotide sequence comprising the dhaT gene from *Klebsiella pneumoniae* or homolg thereof;

(v) a nucleotide sequence encoding glycerol-3-phosphate dehydrogenase;

(vi) a nucleotide sequence encoding glycerol-3-phosphatase; and/or (vii) a nucleotide sequence encoding a homolog of any one of (i) through (iv)

and then regenerating a plant from said cells.

Preferably, the plant is a C4 grass and, in a particularly preferred embodiment, sugarcane.

In order that 1,3-propanediol may be produced in cells of a C4 grass, suitable sequences such as those encoding one or more 1,3-propanediol biosynthetic enzymes must be introduced into and expressed in the cells. That is, the plant needs to undergo genetic modification so that the metabolites and/or metabolic and/or biosynthetic pathways can be harnessed for the production of the 1,3-propanediol or a precursor thereof. This may conveniently be achieved through the use of genetic constructs, engineered to comprise nucleotide sequences required to effect 1,3-propanediol production.

Clearly, the genetic sequences may be modified to insert any leader, tail or signal sequence to direct the enzyme to an appropriate location in the cell.

In another preferred embodiment of the present invention, the plant selected is a C4 grass and the product of interest is 2-phenylethanol (2-PE).

2-phenylethanol (2-PE) is an important flavour and fragrance compound with a rose-like odour. Most of the world's annual production of several thousand tons is synthesised by chemical means but, due to increasing demand for natural flavours, alternative production methods are being sought (Etschmann et al. *Appl Micribiol Biotechnol* 59:1-8, 2002)

Figure 11:
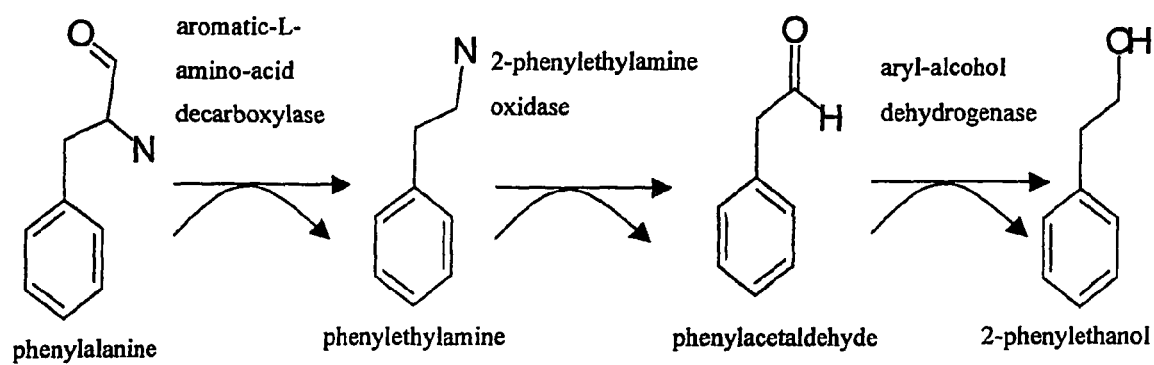
FIG. 11 is a graphical representation showing 2-phenylethanol biosynthesis.
Figure 12:
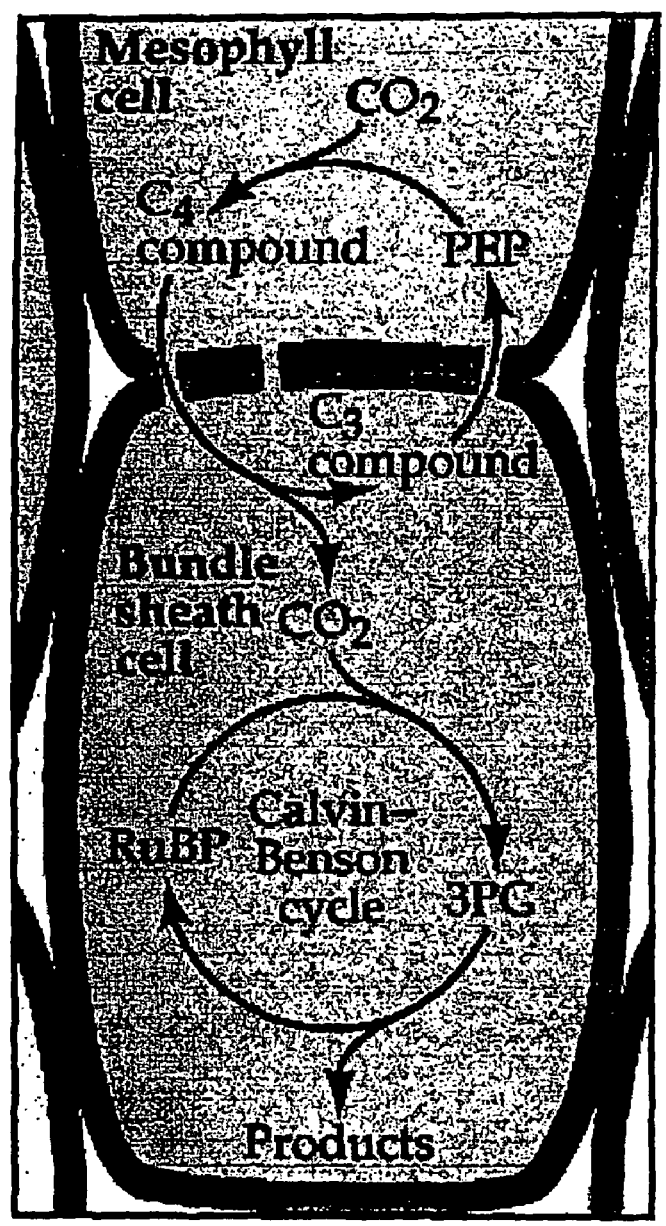
FIG. 12 is a graphical representation showing the basic steps of C4 carbon assimilation.
Figure 13:
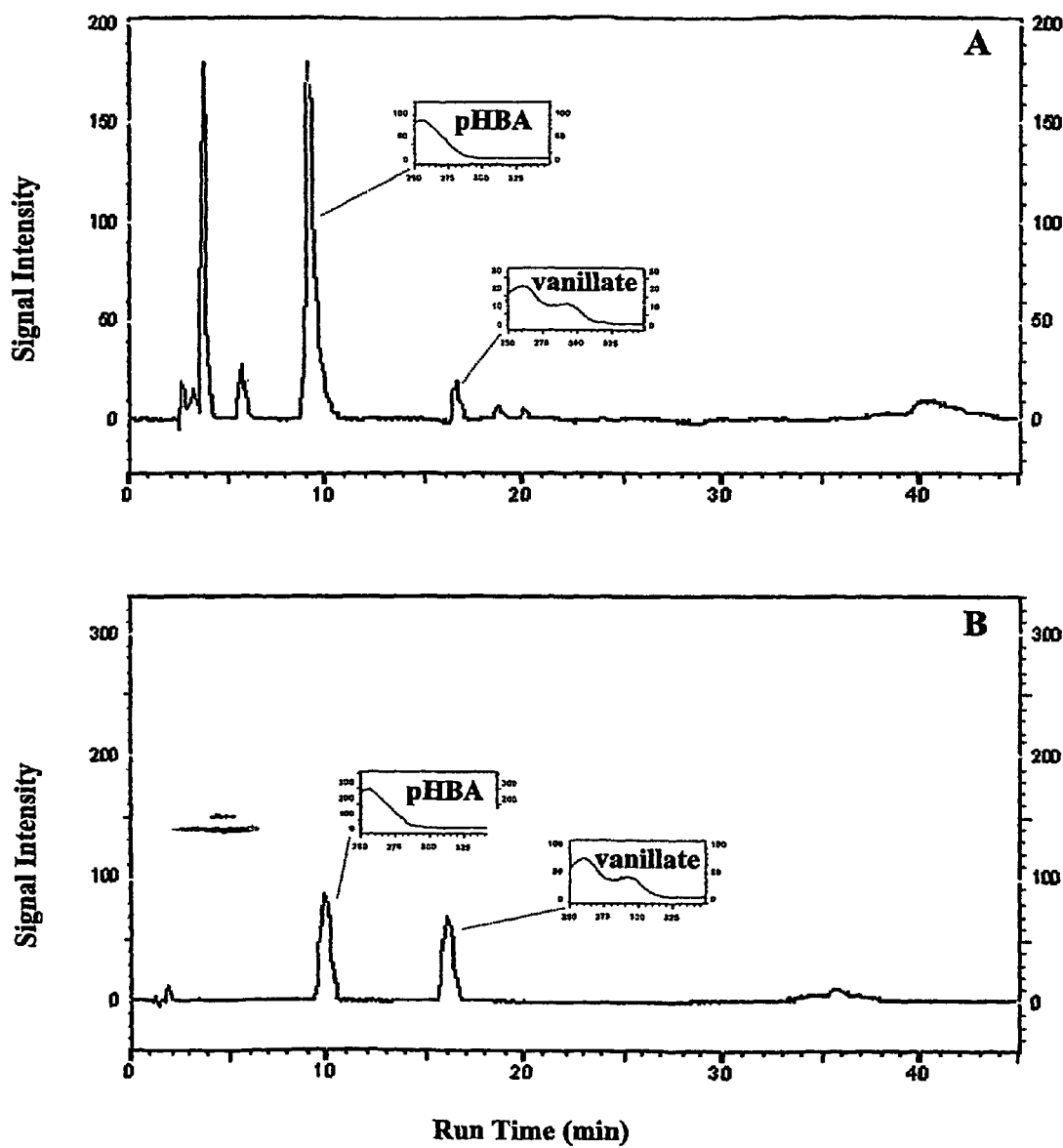
FIG. 13 is a graphical representation depicting the detection of pHBA and vanillate by HPLC in acid hydrolysed leaf samples taken from sugarcane leaves expressing the HCHL transgene. A: Indicated peaks show the presence of pHBA and vanillate in the leaf extract. Insets show the characteristic spectrum profiles for the respective compounds. B: Peaks produced by pHBA and vanillate synthetic standards.

A biological pathway for the biosynthesis of 2-PE is presented in FIG. 11.

Sugarcane has a productive phenylpropanoid pathway and should adapt readily to increased demands placed on it for synthesis of 2-PE.

Accordingly, in another aspect, the present invention further contemplates a method for producing 2-phenylethanol in a C4 grass, said method comprising expressing one or more genetic sequences which encode enzymes required for the production of 2-phenylethanol, or a homolog or precursor thereof in a cell of a C4 grass such that the 2-phenylethanol accumulates in the cytosol, storage vacuole, plastid or non-plastid organelle, or is secreted extra-cellularly.

Any of the disclosed biosynthetic steps, or a combination of these, may be adapted to provide suitable genetic sequences for use in the production of 2-phenylethanol, or precursors thereof, a C4 grass such as in sugarcane. Consequently, genetic sequences which "encode enzymes required for the production of 2-phenylethalol" as used herein in the context of the present invention may comprise a combination of one or more of any sequence wherein the enzyme or enzymes thereby encoded usually operate in vivo singly or together to effect the biosynthesis of 2-phenylethanol or a precursor thereof.

Another aspect of the present invention contemplates a method for producing 2-phenylethanol in a C4 grass, said method comprising expressing one or more genetic sequences encoding aromatic-L-amino acid decarboxylase, 2-phenylethylamine oxidase and aryl-alcohol dehydrogenase in cells of a C4 grass such that 2-phenylethanol accumulates anywhere in the cell or extracellular matrix of the plant.

Accordingly, reference herein to aromatic-L-amino acid decarboxylase, 2-phenylethylamine oxidase and aryl-alcohol dehydrogenase includes all homologs thereof.

In another embodiment, the present invention contemplates a method for generating a plant which produces 2-phenylethanol or a precursor thereof, said method comprising introducing into cells of said plant a genetic sequence comprising at least one of the following:
 (i) a nucleotide sequence encoding a aromatic-L-amino acid decarboxylase and/or;
 (ii) a nucleotide sequence encoding 2-phenylethylamine oxidase;
 (iii) a nucleotide sequence encoding aryl-alcohol dehydrogenase; and/or
 (iv) a nucleotide sequence encoding a homolog of any one of (i) through (iii)

and then regenerating a plant from said cells.

Preferably, the plant is a C4 grass and, in a particularly preferred embodiment, sugarcane.

In order that 2-phenylethanol may be produced in cells of a C4 grass, suitable sequences such as those encoding one or more 2-phenylethanol biosynthetic enzymes must be introduced into and expressed in the cells. That is, the plant needs to undergo genetic modification so that the metabolites and/or metabolic and/or biosynthetic pathways can be harnessed for the production of the 2-phenylethanol or a precursor thereof. This may conveniently be achieved through the use of genetic constructs, engineered to comprise nucleotide sequences required to effect 2-phenylethanol production.

Clearly, the genetic sequences may be modified to insert any leader, tail or signal sequence to direct the enzyme to an appropriate location in the cell.

In another preferred embodiment of the present invention, the plant selected is a C4 grass and the product of interest is pHBA.

Figure 14:
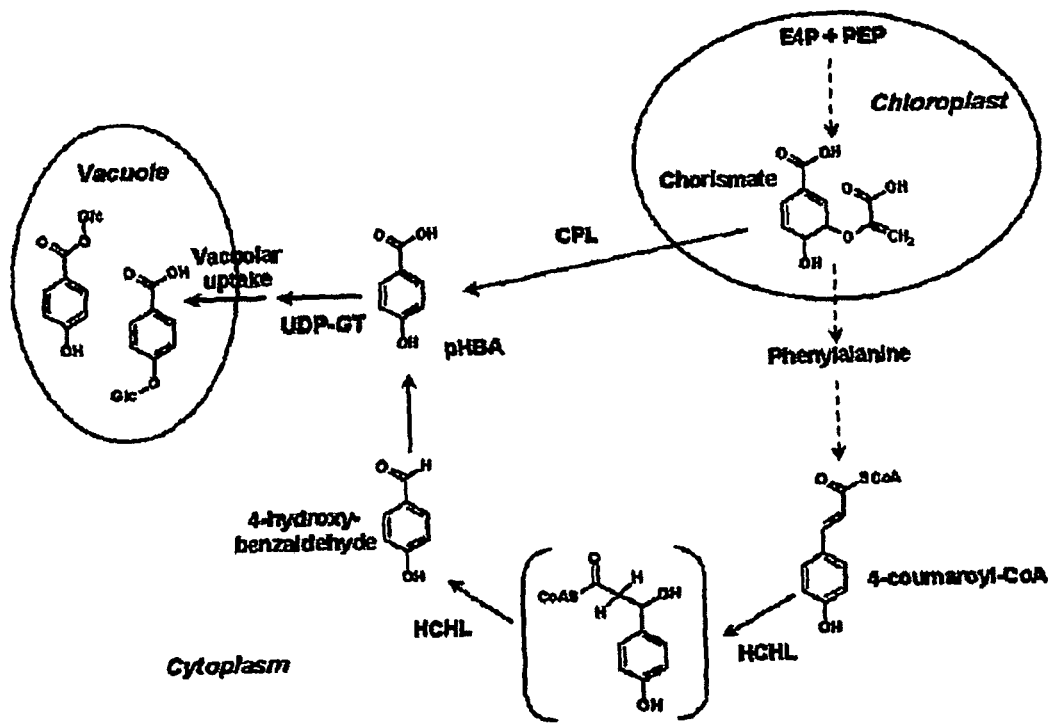
FIG. 14 is a graphical representation of p-hydroxybenzoic acid (pHBA) synthesis in planta can be accomplished by the introduction of E. coli chorismate pyruvate-lyase (CPL) or P. fluorescens 4-hydroxycinnamoyl-CoA hydratase/lyase (HCHL). CPL converts plastidal chorismate into pHBA whilst HCHL converts cytosolic 4-coumaroyl-CoA into 4-hydroxybenzaldehyde via a â-hydroxy thioester intermediate which is subsequently oxidized to pHBA by endogenous NAD+-linked dehydrogenases. In both instances, the majority of the resultant free acid is glucosylated and transported into vacuoles. Abbreviations: E4P, erythrose-4-phosphate; PEP, phosphoenolpyruvate; UDP-GT, UDP-glucosyltransferase.

A schematic depicting the pHBA biosynthetic pathway is shown in FIG. 14.

In order to effect pHBA production in sugarcane, a chloroplast targeted version of *E. coli* situated between the maize ubi-1 promoter and nos terminator of the expression construct pU3z-mcs-nos, was co-bombarded with a plasmid containing a selectable marker (pUKN) into embryogenic sugarcane callus to yield the UC series of transgenic lines. The UH series of plants was generated in the same manner using an analogous expression construct that contained the ORF of the *P. fluorescens* HCHL gene. The regenerated plants were grown in a greenhouse for four weeks and were then analyzed for pHBA accumulation in leaf tissue using HPLC.

pHBA accumulated in the transformed plants as two glucose conjugates, ie, a phenolic glucoside and a glucose ester. Both compounds contained a single glucose molecule that was attached by a 1-O-□-D linkage to the hydroxyl or carboxyl group of pHBA. The predominant product in all of the plants examined was the phenolic glucoside, which accounted for at least 90% of the pHBA.

The mean value for the population was 0.41%±0.04% of dry weight (DW), which is almost 30-fold-higher than the mean value for the non-transgenic control plants 0.014%±0.01% DW. More important, the pHBA glucoside content of the best plant was 1.5% DW, which is equivalent to 0.69% DW free pHBA after correcting for the attached glucose molecule. This value is three times higher than the highest value obtained with transgenic tobacco plants expressing a different chloroplast-targeted version of CPL. The HCHL-expressing sugarcane plants accumulated even higher levels of pHBA. The mean value for total pHBA glucose conjugates in the UH lines was 0.70%±0.07% DW, and the highest level observed at this stage of development was 2.6% DW.

Based on the results obtained with the 4-week-old plants, a subset of the primary transformants was selected for further evaluation; and leaf levels of pHBA were determined after 16 weeks additional growth. Included in this analysis were the two CPL-expressing plants that previously exhibited the highest levels of product accumulation (UC63 and UC65) and five HCHL-expressing plants. The methanol-extracted samples were subjected to acid hydrolysis, which quantitatively hydrolyzes both pHBA glucose conjugates, and free pHBA was determined by HPLC.

Figure 3:
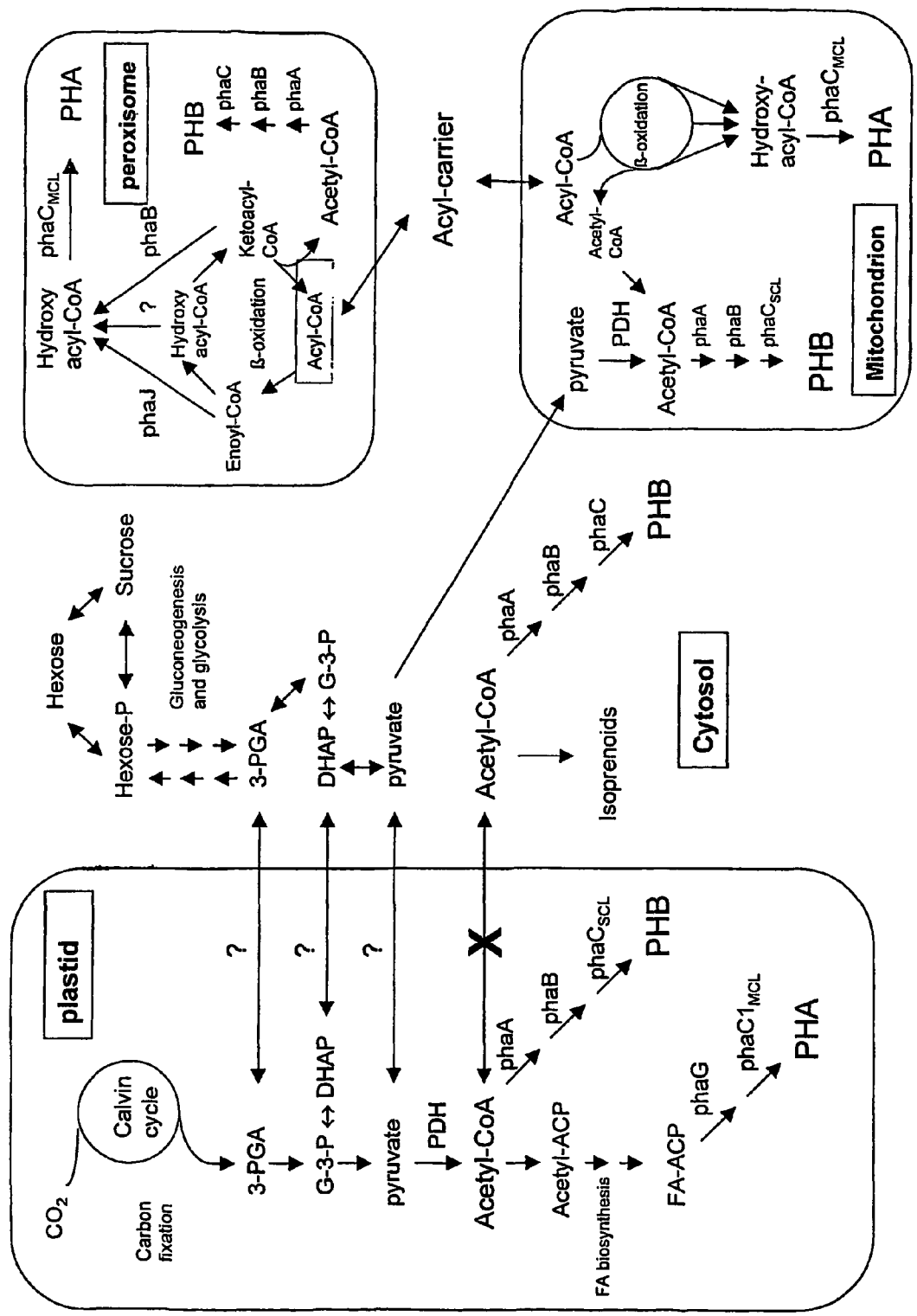
FIG. 3 is a diagrammatic representation of the flow of carbon in sub-cellular compartments within a sugarcane cell.

It was anticipated that pHBA production would continue throughout development and that the 20-week-old plants would have higher levels of pHBA glucosides than the 4-week-old plants. However, the increase in pHBA content with age was not very dramatic nor was it universally observed when product accumulation was expressed on a dry weight basis (FIG. 3A). Part of the explanation for this is the lower water content of the older plant leaf tissue. For example, the average dry weight to wet weight ratio for the 20-week-old plants was 0.23, while the corresponding value for the 4-week-old plants was 0.15. When this phenomenon is taken into account and product accumulation is expressed on a fresh weight basis it becomes far more apparent that pHBA levels did increase as the plants continued to grow (FIG. 3B), except for the two CPL-expressing plants.

The 20-week-old primary transformants were large enough to screen for stalk levels of pHBA without damaging the plants. At this stage of development, the oldest stem tissue is semi-mature and new tillers emerge. Since the stalk is the only part of the sugarcane plant that is normally harvested in the existing sugar mill infrastructure, pHBA accumulation in this tissue is the most important gauge for technical success. Leaf and stem samples were taken from 20-week-old plants, and total pHBA was determined by HPLC after methanol extraction and acid hydrolysis. The third internode from the bottom of the plant was the source of stem tissue for this analysis, and the leaf samples were obtained from the third fully unfurled leaf from the top of the plant. Generally speaking, leaf levels of pHBA were considerably higher than stalk levels.

However, the difference was much more pronounced for the CPL-expressing plants. For example, the average stalk to leaf ratio of pHBA for the five UH lines that were examined was 0.324±0.031, and the highest stalk level of pHBA was 0.24% DW, which is equivalent to 0.52% pHBA glucose conjugates. In marked contrast, the corresponding ratios for UC63 and UC65 were 0.135 and 0.133, respectively, and product accumulation in the stalk of the best plant (UC63) was only 0.06% DW. Since there are no reported values in the literature for pHBA levels in stem tissue for transgenic plants expressing CPL or HCHL, it will be very interesting to see if these observations will extend to other plant systems. Nevertheless, taken together the above results suggest that HCHL is a better catalyst for pHBA production in sugarcane than CPL, and subsequent studies focused on the UH series of plants.

To gain a better understanding of pHBA accumulation in different parts the plant, leaf and stem segments were sampled from the primary shoot of 20-week-old UH1. The first leaf at the top with a fully visible dewlap was designated "leaf 1" and consecutive leaves down the stalk were numbered in ascending order. The stem segments were numbered similarly with "internode 1" corresponding to the internode immediately above the point of attachment of leaf 1. Note that the values shown refer to total pHBA after acid hydrolysis. Except for the youngest leaf examined, product accumulation in leaves was relatively uniform along the length of the plant achieving a maximum value of ~1.0% DW. Product accumulation also varied along the length of the leaf, with the tip of the leaf having about twice as much pHBA as the base of leaf. A similar trend was observed in the stalk, but there was a much larger discrepancy between young stem tissue and old stem tissue. In agreement with the results described above, pHBA levels in mature stem tissue were about 3-fold lower than mature leaf tissue. These results add additional support to the notion that pHBA accumulation in HCHL-expressing sugarcane plants increases as a function of time.

Figure 5:
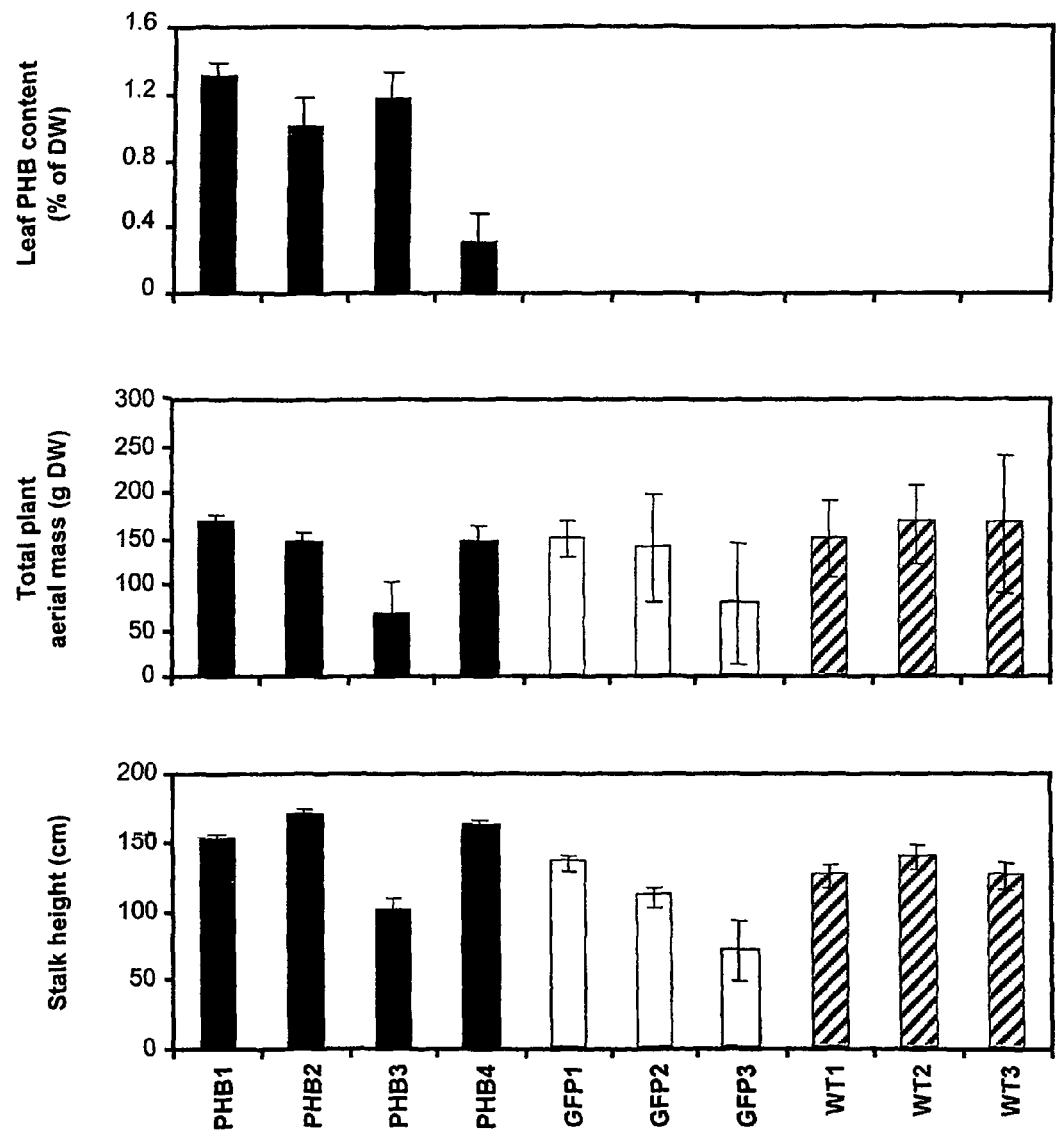
FIG. 5 illustrates the agronomic performance of PHB-producing sugarcane lines. Four transgenic sugarcane lines expressing the PHB biosynthesis genes of $R.$ $eutropha$ (filled bars) were grown for 3 months in a randomised glasshouse plot, together with GFP expressing (open bars) and tissue-culture-regenerated WT hatched bars) plants as controls. PHB content in lamina from the tips of mature leaves was quantified by HPLC analysis. Data are the mean±SE (n=3). DW=dry-weight.

Additional insight on pHBA distribution was obtained from dissection experiments. Three different compartments of the stalk were examined: rind, pith, and vascular bundles. The most pHBA was found in the rind (1% DW), while the pith and vascular bundles had 3- to 4-fold-lower levels. Indeed, pHBA levels in the rind were very similar to values obtained from the leaf midrib and leaf laming Of all of the HCHL-expressing primary transformants monitored, UH98 consistently had the highest levels of pHBA in both leaf and stem tissue. When this plant was 20 weeks old pHBA accumulation in leaf tissue was 2.8% DW (leaf lamina, 3.35% DW; leaf midrib, 1.61% DW). The corresponding value for mature stem tissue was 0.67% DW (rind, 0.96% DW; pith, 0.65% DW). Despite these very high levels of pHBA glucose conjugates, UH98 was morphologically indistinguishable from the non-transformed control line TC1 (FIG. 5).

The present invention contemplates a method for producing pHBA in a C4 grass, the method comprising expressing one or more genetic sequences encoding one or more pHBA biosynthetic enzymes in cells of a C4 grass such that pHBA accumulates anywhere in the cell or extra-cellular matrix of the plant.

Accordingly, reference herein to hydroxycinnamoyl-CoA hydratase/lyase or chorismate pyruvate lyase includes all homologs thereof.

In a preferred embodiment, the present invention contemplates a method for generating a plant which produces pHBA or a precursor thereof, said method comprising introducing into cells of said plant a genetic sequence comprising at least one of the following:
(i) a nucleotide sequence encoding hydroxycinnamoyl-CoA hydratase/lyase;
(ii) a nucleotide sequence encoding chorismate pyruvate lyase;
(iii) a nucleotide sequence comprising the ubiC gene from *E. coli*, or a homolg thereof; and/or
(iv) a nucleotide sequence comprising the HCHL gene from *Pseudomonas fluorescens* or homolg thereof;

and then regenerating a plant from said cells.

Preferably; the plant is a C4 grass and, in a particularly preferred embodiment, sugarcane.

In order that pHBA may be produced in cells of a C4 grass, suitable sequences such as those encoding one or more pHBA biosynthetic enzymes must be introduced into and expressed in the cells. That is, the plant needs to undergo genetic modification so that the metabolites and/or metabolic and/or biosynthetic pathways can be harnessed for the production of the pHBA or a precursor thereof. This may conveniently be achieved through the use of genetic constructs, engineered to comprise nucleotide sequences required to effect pHBA production.

Clearly, the genetic sequences may be modified to insert any leader, tail or signal sequence to direct the enzyme to an appropriate location in the cell. In a preferred embodiment, the pHBA biosynthetic enzymes are targetted to the plastid.

To effect expression of the nucleotide sequence of the present invention, it may conveniently be incorporated into a chimeric genetic construct comprising inter alia one or more of the following: a promoter sequence, a 5' non-coding region, a cis-regulatory region such as a functional binding site for transcriptional regulatory protein or translational regulatory protein, an upstream activator sequence, an enhancer element, a silencer element, a TATA box motif, a CCAAT box motif, an upstream open reading frame, transcriptional start site, translational start site, and/or nucleotide sequence which encodes a leader sequence, and a 3' non-translated region. Preferable the chimeric genetic construct is designed for transformation of plants as hereinafter described.

The term "5' non-coding region" is used herein in its broadest context to include all nucleotide sequences which are derived from the upstream region of an expressible gene, other than those sequences which encode amino acid residues which comprise the polypeptide product of said gene, wherein 5' non-coding region confers or activates or otherwise facilitates, at least in part, expression of the gene.

The term "gene" is used in its broadest context to include both a genomic DNA region corresponding to the gene as well as a cDNA sequence corresponding to exons or a recombinant molecule engineered to encode a functional form of a product.

As used herein, the term "cis-acting sequence" or "cis-regulatory region" or similar term shall be taken to mean any sequence of nucleotides which is derived from an expressible genetic sequence wherein the expression of the first genetic sequence is regulated, at least in part, by said sequence of nucleotides. Those skilled in the art will be aware that a cis-regulatory region may be capable of activating, silencing, enhancing, repressing or otherwise altering the level of expression and/or cell-type-specificity and/or developmental specificity of any structural gene sequence.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kilobase pairs (kb) of the start site of transcription of the gene.

In the present context, the term "promoter" is also used to describe a synthetic or fusion molecule, or derivative which confers, activates or enhances expression of a structural gene or other nucleic acid molecule, in a plant cell. Preferred promoters according to the invention may contain additional copies of one or more specific regulatory elements to further enhance expression in a cell, and/or to alter the timing of expression of a gene to which it is operably connected.

The term "operably connected" or "operably linked" in the present context means placing a gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting, i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting, i.e. the genes from which it is derived.

Promoter sequences contemplated by the present invention may be native to the host plant to be transformed or may be derived from an alternative source, where the region is functional in the host plant Other sources include the *Agrobacterium* T-DNA genes, such as the promoters for the biosynthesis of nopaline, octapine, mannopine, or other opine promoters; promoters from plants, such as the ubiquitin promoter; tissue specific promoters (see, e.g. U.S. Pat. No. 5,459, 252; International Patent Publication No. WO 91/13992); promoters from viruses (including host specific viruses), or partially or wholly synthetic promoters. Numerous promoters that are functional in mono- and dicotyledonous plants are well known in the art (see, for example, Greve, *J. Mol. Appl. Genet.* 1: 499-511, 1983; Salomon et al., *EMBO J.* 3: 141- 146, 1984; Garfinkel et al., *Cell* 27: 143-153, 1983; Barker et al., *Plant Mol. Biol.* 2: 235-350, 1983); including various promoters isolated from plants (such as the Ubi promoter from the maize ubi-1 gene, e.g. U.S. Pat. No. 4,962,028) and viruses (such as the cauliflower mosaic virus promoter, CaMV 35S).

In the context of the present invention, a particularly useful tissue-specific promoter is one which drives expression specifically in the stems of sugarcane plants. Such a stem-specific promoter is, for example, that described in International Patent Publication No. WO 01/18211.

The promoter sequences may include regions which regulate transcription, where the regulation involves, for example, chemical or physical repression or induction (e.g. regulation based on metabolites, light, or other physicochemical factors; see, e.g. International Patent Publication No. WO 93/06710 disclosing a nematode responsive promoter) or regulation based on cell differentiation (such as associated with leaves, roots, seed, or the like in plants; see, e.g. U.S. Pat. No. 5,459, 252 disclosing a root-specific promoter). Thus, the promoter region, or the regulatory portion of such region, is obtained from an appropriate gene that is so regulated. For example, the ribulose 1,5-bisphosphate carboxylase gene is light-induced and may be used for transcriptional initiation. Other genes are known which are induced by stress, temperature, wounding, pathogen effects, etc.

The chimeric genetic construct of the present invention may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon.

The 3' non-translated regulatory DNA sequence preferably includes from about 50 to 1,000 nucleotide base pairs and may contain plant transcriptional and translational termination sequences in addition to a polyadenylation signal and any other regulatory signals capable of effecting mRNA processing or gene expression. Examples of suitable 3' non-translated sequences are the 3' transcribed non-translated regions containing a polyadenylation signal from the nopaline synthase (nos) gene of *Agrobacterium tumefaciens* (Bevan et al., *Nucl. Acid. Res.* 11: 369, 1983) and the terminator for the 17 transcript from the octopine synthase gene of *Agrobacterium tumefaciens*. Alternatively, suitable 3' non-translated sequences may be derived from plant genes such as the 3' end of the protease inhibitor I or II genes from potato or tomato, the soybean storage protein genes and the pea E9 small subunit of the ribulose-1,5-bisphosphate carboxylase (ss-RUBISCO) gene, although other 3' elements known to those of skill in the art can also be employed. Alternatively, 3' non-translated regulatory sequences can be obtained de novo as, for example described by An (*Methods of Enzymology* 153: 292, 1987), which is incorporated herein by reference.

A genetic construct can also be introduced into a vector, such as a plasmid. Plasmid vectors include additional DNA sequences that provide for easy selection, amplification, and transformation of the expression cassette in prokaryotic and eukaryotic cells, e.g. pUC-derived vectors, pSK-derived vectors, pGEM-derived vectors, pSP-derived vectors, or pBS-derived vectors. Additional DNA sequences include origins of replication to provide for autonomous replication of the vector, selectable marker genes, preferably encoding for example, antibiotic or herbicide resistance or green fluorescent protein or other visible markers, unique multiple cloning sites providing for multiple sites to insert DNA sequences or genes encoded in the chimeric genetic construct, and sequences that enhance transformation of prokaryotic and eukaryotic cells.

The vector preferably contains an element(s) that permits either stable integration of the vector or a chimeric genetic construct contained therein into the host cell genome, or autonomous replication of the vector in the cell independent of the genome of the cell. The vector, or a construct contained therein, may be integrated into the host cell genome when introduced into a host cell. For integration, the vector may rely on a foreign or endogenous DNA sequence present therein or any other element of the vector for stable integration of the vector into the genome by homologous recombination. Alternatively, the vector may contain additional nucleic acid sequences for directing integration by homologous recombination into the genome of the host cell. The additional nucleic acid sequences enable the vector or a construct contained therein to be integrated into the host cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

For cloning and sub-cloning purposes, the vector may further comprise an origin of replication enabling the vector to replicate autonomously in a host cell such as a bacterial cell. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. The origin of replication may be one having a mutation to make its function temperature-sensitive in a *Bacillus* cell (see, e.g. Ehrlich, *Proc. Natl. Acad. Sci. USA* 75; 1433, 1978).

To facilitate identification of transformed cells, the vector desirably comprises a further genetic construct comprising a selectable or screenable marker gene. The actual choice of a marker is not crucial as long as it is functional (i.e. selective) in combination with the plant cells of choice. The marker gene and the nucleotide sequence of interest do not have to be linked, since co-transformation of unlinked genes as, for example, described in U.S. Pat. No. 4,399,216 is also an efficient process in plant transformation.

Included within the terms selectable or screenable marker genes are genes that encode a "secretable marker" whose secretion can be detected as a means of identifying or selecting for transformed cells. Examples include markers that encode a secretable antigen that can be identified by antibody interaction, or secretable enzymes that can be detected by their catalytic activity. Secretable proteins include, but are not restricted to, proteins that are inserted or trapped in the cell wall (e.g. proteins that include a leader sequence such as that found in the expression unit of extensin or tobacco PR-S); small, diffusible proteins detectable, for example, by ELISA; and small active enzymes detectable in extracellular solution such as, for example, α-amylase, β-lactamase, phosphinothricin acetyltransferase).

Examples of bacterial selectable markers are the dal genes from *Bacillus subtilis* or *Bacillus licheniformis*, or markers that confer antibiotic resistance such as ampicillin, kanamycin, erythromycin, chloramphenicol or tetracycline resistance. Exemplary selectable markers for selection of plant transformants include, but are not limited to, a hyg gene which encodes hygromycin B resistance; a neomycin phosphotransferase (npt) gene conferring resistance to kanamycin, paromomycin, G418 and the like as, for example, described by Potrykus et al. (*Mol. Gene. Genet.* 199: 183, 1985); a glutathione-S-transferase gene from rat liver conferring resistance to glutathione derived herbicides as, for example, described in EP-A 256 223; a glutamine synthetase gene conferring, upon overexpression, resistance to glutamine synthetase inhibitors such as phosphinothricin as, for example, described International Patent Publication No. WO 87/05327, an acetyl transferase gene from *Streptomyces viridochromogenes* conferring resistance to the selective agent phosphinothricin as, for example, described in European Patent Application No. EP-A 275 957, a gene encoding a 5-enolshikimate-3-phosphate synthase (EPSPS) conferring tolerance to N-phosphonomethylglycine as, for example, described by Hinchee et al. (*Biotech* 6: 915, 1988), a bar gene conferring resistance against bialaphos as, for example, described in International Patent Publication No. WO 91/02071; a nitrilase gene such as bxn from *Klebsiella ozaenae* which confers resistance to bromoxynil; a dihydrofolate reductase (DHFR) gene conferring resistance to methotrexate (Thillet et al., *J. Biol. Chem.* 263: 12500, 1988); a mutant acetolactate synthase gene (ALS), which confers resistance to imidazolinone, sulfonylurea or other ALS-inhibiting chemicals (European Patent Application No. EP-A-154 204) or a mutated anthranilate synthase gene that confers resistance to 5-methyl tryptophan.

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., *Biochem. Biophys. Res. Comm.* 126: 1259, 1985), which may be employed in calcium-sensitive bioluminescence detection; a green fluorescent protein gene (Niedz et al., *Plant Cell Reports* 14: 403, 1995); a luciferase (luc) gene (Ow et al., *Science* 234: 856, 1986), which allows for bioluminescence detection; a β-lactamase gene (Sutcliffe, *Proc. Natl. Acad. Sci. USA* 75: 3737, 1978), which encodes an enzyme for which various chromogenic substrates are known (e.g. PADAC, a chromogenic cephalosporin); an R-locus gene, encoding a product that regulates the production of anthocyanin pigments (red colour) in plant tissues (Dellaporta et al., in *Chromosome Structure and Function* pp. 263-282, 1988); an α-amylase gene (Ikuta et al., *Biotech* 8: 241, 1990); a tyrosinase gene (Katz et al, *J. Gen. Microbiol.* 129: 2703, 1983) which encodes an enzyme capable of oxidizing tyrosine to dopa and dopaquinone which in turn condenses to form the easily detectable compound melanin; or a xylE gene (Zukowsky et al., *Proc. Natl. Acad. Sci. USA* 80: 1101, 1983), which encodes a catechol dioxygenase that can convert chromogenic catechols.

A further aspect of the present invention provides a transfected or transformed cell, tissue, or organ from a C4 grass, which comprises a nucleotide sequence encoding one or more enzymes required for the production of a useful product.

The vectors and chimeric genetic construct(s) of the present invention may be introduced into a cell by various techniques known to those skilled in the art. The technique used may vary depending on the known successful techniques for that particular organism.

Techniques for introducing vectors, chimeric genetic constructs and the like into cells include, but are not limited to, transformation using $CaCl_2$ and variations thereof, direct DNA uptake into protoplasts, PEG-mediated uptake to protoplasts, microparticle bombardment, electroporation, microinjection of DNA, microparticle bombardment of tissue explants or cells, vacuum-infiltration of tissue with nucleic acid, and T-DNA-mediated transfer from *Agrobacterium* to the plant tissue.

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the genetic construct may incorporate a plasmid capable of replicating in the cell to be transformed.

Examples of microparticles suitable for use in such systems include 0.1 to 10 μm and more particularly 0.5 to 5 μm tungsten particles or gold spheres. The DNA construct may be deposited on the microparticle by any suitable technique, such as by precipitation.

Plant tissue capable of subsequent clonal propagation, whether by organogenesis or embryogenesis, may be transformed with a chimeric genetic construct of the present invention and a whole plant generated therefrom. The particular tissue chosen will vary depending on the clonal propagation systems available for, and best suited to, the particular species being transformed. Exemplary tissue targets include leaf disks, embryos, cotyledons, hypocotyls, megagametophytes, callus tissue, existing meristematic tissue (e.g. apical meristem, axillary buds, and root meristems), and induced meristem tissue (e.g. cotyledon meristem and hypocotyl meristem).

The regenerated transformed plants may be propagated by a variety of means, such as by clonal propagation or classical breeding techniques. For example, a first generation (or T1) transformed plant may be selfed to give a homozygous second generation (or T2) transformant, and the T2 plants further propagated through classical breeding techniques.

Even more particularly, the present invention provides a plant cell or multicellular plant or progeny thereof wherein said cell, plant, progeny or part thereof exhibits an activity to manufacture PHAs.

The term "genetically modified" is used in its broadest sense and includes introducing gene(s) into cells, mutating gene(s) in cells and altering or modulating the regulation of gene(s) in cells. In the context of the present invention, a transgenic cell or plant line may also be considered as a mutant cell or plant line when compared with its non-transgenic counterpart. In essence, a selected plant is first genetically modified to introduce a genetic sequence encoding a desired product or intermediate.

Where genetic sequences for more than one gene are to be used in the performance of the present invention, they may be introduced simultaneously or sequentially, separately or together, into the target cells that are to be transformed. For example, a singe genetic construct may comprise all the required genetic sequences for the practice of the subject invention, and this single construct may be introduced into the cells via any number of different means, as discussed below. Moreover, each genetic sequence may be operable linked to and under the control of its own promoter, or may be comprised within a single polycistronic unit. Alternatively, separate genetic constructs may be utilized, each comprising one of the needed genetic sequences. In this event, more than one construct may be introduced into the target cells simultaneously or sequentially. Here and elsewhere throughout the subject specification, the terms "target cells" and "cells to be transformed" should be regarded as being synonymous and refer to cells of a C4 grass that are to be used in accordance with the present invention as a bioreactor.

The one or more genetic sequences, introduced into a C4 grass plant cell, need to be expressed in order to enable the manufacture and accumulation of a product. The term "expression" is to be construed in its broadest sense and includes and encompasses transcription and translation of a genetic sequence to a translation product.

Some plant cells may already comprise a homolog of one or more of the genetic sequences encoding enzymes needed for the production of a given product. In instances where a target plant cell, such as a sugarcane cell, already comprises one or more suitable genetic sequences, capable of directing sufficiently high expression, only those enzymes missing in a given pathway need be provided through via a genetic construct as described above.

The present invention extends to homologs and derivatives of any suitable sequences, whether found naturally in a target cell or provided exogenously having been derived from another plant, animal, protist, fungal, archeal or bacterial source, inter alia. The derivatives may be at the protein or nucleic acid level.

By "derivative" in relation to a polypeptide is meant a polypeptide that has been derived from the basic sequence by modification, for example, by conjugation or complexing with other chemical moieties or by post-translational modification techniques as would be understood in the art The term "derivative" also includes within its scope alterations that have been made to a parent sequence including additions, or deletions that provide for functionally-equivalent molecules. Accordingly, the term "derivative" encompasses molecules that affect a plant's phenotype in the same way as does the parent an amino acid sequence from which it was generated. Also encompassed are polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

"Polypeptide", "peptide" and "an amino acid sequence" are used interchangeably herein to refer to a polymer of amino acid residues and to variants and synthetic analogues thereof. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers.

The term "derivative" also encompasses fragments. A "fragment", as used herein, means a portion or a part of a full-length parent polypeptide, which retains the activity of the parent polypeptide. As used herein, the term "biologically-active fragment" includes deletion mutants and small peptides, for example, of at least 10, preferably at least 20 and more preferably at least 30 contiguous amino acids, which comprise the above activity. Peptides of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of an amino acid sequence of the invention with proteinases such as endoLys-C, endoArg-C, endoGlu-C and *staphylococcus* V8-protease. The digested fragments can be purified by, for example, high performance liquid chromatographic (HPLC) techniques. Any such fragment, irrespective of its means of generation, is to be understood to be encompassed by the term "derivative" as used herein.

The terms "variant" and "homolog" refer to nucleotide sequences displaying substantial sequence identity with a reference nucleotide sequences or polynucleotides that hybridize with a reference sequence under stringency conditions that are defined hereinafter. The terms "nucleotide sequence", "polynucleotide" and "nucleic acid molecule" may be used herein interchangeably and encompass polynucleotides in which one or more nucleotides have been added or deleted, or replaced with different nucleotides. In this regard, it is well understood in the art that certain alterations inclusive of mutations, additions, deletions and substitutions can be made to a reference nucleotide sequence whereby the altered polynucleotide retains the biological function or activity of the reference polynucleotide. The term "variant" also includes naturally-occurring allelic variants.

The extent of homology may be determined using sequence comparison programs such as GAP. In this way, sequences of a similar or substantially different length to those cited herein might be compared by insertion of gaps into the alignment, such gaps being determined, for example, by the comparison algorithm used by GAP, as is further discussed below.

Homologous sequences will generally hybridize under particular specified conditions. The term "hybridization" denotes the pairing of complementary nucleotide sequences to produce a DNA-DNA hybrid or a DNA-RNA hybrid. Complementary base sequences are those sequences that are related by the base-pairing rules. In DNA-DNA hybridization, A pairs with T and C pairs with G. In DNA-RNA hybridization, U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

The extent of hybridization that may be displayed by homologous sequences depends on the conditions of, for example, temperature, ionic strength presence or absence of certain organic solvents, under which hybridization and washing procedures are carried out. The higher the stringency, the higher will be the degree of complementarity between immobilised target nucleotide sequences and the labelled probe polynucleotide sequences that remain hybridized to the target after washing. "High stringency conditions" refers to temperature and ionic conditions under which only nucleotide sequences having a high frequency of complementary bases will hybridize. The stringency required is nucleotide-sequence dependent, and further depends upon the various components present during hybridization and subsequent washes, and the time allowed for these processes. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$, allowing a high level of mismatching between hybridized sequences. Those skilled in the art will recognize that other physical and chemical parameters in the hybridization and wash stages can also be altered to affect the outcome of a detectable hybridization signal from a specific level of homology between target and probe sequences.

Reference herein to "low stringency conditions" is generally determined at 42° C. and includes and encompasses from at least about 0% v/v to at least about 15% v/v formamide, and from at least about 1 M to at least about 2 M salt for hybridization, and at least about 1 M to at least about 2 M for washing conditions. Alternative stringency conditions may be applied where necessary, such as: medium stringency, which includes and encompasses from at least about 16% v/v to at least about 30% v/v formamide, and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide, and from at least about 0.01 M to least about 0.15 M salt for hybridization, and at least about 0.01 M to at least about 0.15 M salt for washing conditions.

Terms used to describe sequence relationships between two or more nucleotide sequences or amino acid sequences include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al., *Nucl. Acids Res.* 25: 3389, 1997. A detailed discussion of sequence analysis can be found in Unit 19.3 of Ausubel et al., "Current Protocols in Molecular Biology" John Wiley & Sons Inc, 1994-1998, Chapter 15.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e. the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

The one or more constructs may be introduced into a plant cell by any number of well-recognized means such as discussed above.

Preferably, the genetic constructs of the present invention are introduced via the use of biolistics.

Accordingly, another aspect of the present invention provides a transgenic C4 grass, cells of which have been transformed with one or more genetic sequences such that one of the following products in the cytosol, storage vacuole, non-plastid organelle or extra-cellular matrix of said cells:

(i) polyhydroxyalkanoates
(ii) vanillin
(iii) sorbitol
(iv) indigo
(v) fructans
(vi) lactic acid
(vii) adipic acid
(viii) 1,3-propanediol (ix) 2-phenylethanol (x) pHBA The present invention extends to parts of plants tissue including leaves, stems, vascular bundles, bark, reproductive material, roots and any extracted liquid ("juice") from said plant.

While the present invention is exemplified using the compounds hereinbefore described, it is to be understood that the invention extends to and encompasses the use of any suitable genetic sequence capable of effecting the production of any product in the cells or extracellular matrix of a C4 grass:

The term "gene" is used in its broadest sense and includes cDNA corresponding to the exons of a gene. Accordingly, reference herein to a "gene" is to be taken to include:

(i) a classical genomic gene consisting of transcriptional and/or translational regulatory sequences and/or a coding region and/or non-translated sequences (i.e. introns, 5'- and 3'-untranslated sequences); or (ii) mRNA or cDNA corresponding to the coding regions (i.e. exons) and 5'- and 3'-untranslated sequences of the gene.

The term "gene" is also used to describe synthetic or fusion molecules encoding all or part of an expression product. In particular embodiments, the term "nucleic acid molecule" and "gene" may be used interchangeably.

In order to improve the efficiency and accumulation rate of a product, a suitable genetic sequence or sequences may be more specifically targeted so as to facilitate generation of expression products in particular sub-cellular areas or organelles within the plant. These include, for example, the cytosol, a storage vacuole or a plastid or non-plastid organelle.

The usefulness of a given sub-cellular compartment for a given product depends on the nature and potential toxicity of the product to the plant. For example, PHA production is dependent on both the types of polymer produced and the metabolic pathways being engineered.

One particularly useful sub-cellular area for the production of products such as PHB, 1,3-propanediol and sorbitol, is the cytosol, wherein sucrose is both synthesized via gluconeogenesis and degraded via glycolysis, leading to the production of pyruvate. In the cytosol, PHB is the preferred polymer, as moderate amounts of acetyl-CoA are available for phaA, phaB and phaC. A particularly useful sub-cellular organelle is the mitochondrion, wherein acetyl-CoA, which may be produced from pyruvate via mitochondrial pyruvate dehydrogenase, and/or perhaps from fatty acids via β-oxidation, is used to fuel the TCA cycle. A second useful sub-cellular organelle, with moderate to high acetyl-CoA, is the peroxisome, the site of fatty acid degradation via β-oxidation. These pathways involve the utilization of substantial amounts of acetyl-CoA, depleting reserves and rendering it unavailable for use in manufacture of a product. However, the pyruvate needed for acetyl-CoA production is generated via glycolysis, which, in a sink tissue such as sugarcane stems, is fuelled by sucrose. Hence, the carbon drain that usually results from effecting the production of a product, such as a PHA, vanillin and the like, in a plant cell, is able to be overcome by the sucrose-accumulating plant cell's ability to mobilise its substantial sucrose stores. The deleterious effects resulting from product accumulation observed in non-sucrose-accumulating plant species does not occur in sugarcane, as a concomitant state of general starvation is precluded by the mobilization of sucrose from storage vacuoles, which replenishes the reduction of cellular acetyl-CoA pools caused by the introduced genetic sequences.

Accumulation of PHAs, and other products (particularly products such as pHBA, adipic acid and indigo) may also be targeted to a plastid, such as a chloroplast, where large amounts of acetyl-CoA are used for fatty acid biosynthesis. For example, for the production of PHAs other than PHB, plastids and peroxisomes are the preferred sub-cellular compartment, as PhaG (plastid) and PhaJ (peroxisome) provide monomers suitable for MCL-PHA polymerases such as PhaC1 from intermediates in fatty acid biosynthesis and β-oxidation. In addition, particular biosynthetic pathways from which a particular product may be derived may exist only in the plastid. For example, the shikimate pathway is locatized in the plastid in plants. Products such as indigo and adipic acid may be derived from intermediates of the shikimate pathway via the addition of new biosynthetic enzymes. For these new enzymes to produce the product of interest, they must be localised to the particular organelles where their substrates would be found.

In order to direct product accumulation to a desired sub-cellular location, particular specific "target sequences" may be incorporated into the genetic constructs described above.

A target sequence includes a signal sequence such as a signal sequence to direct the protein to a plastid, vacuole, mitochondrion or other appropriate organ or tissue.

Preferably, accumulation of PHA is in the cytosol or mitochondrion, assisted via mobilization of sucrose reserves located in the storage vacuoles of sugarcane stem cells.

Preferably, accumulation of adipic acid and indigo is in the plastid, wherein the introduced biosynthetic enzymes have access to intermediates of the shikimate pathway.

The plants of the present invention may also be further "tagged" with a reporter that identifies the plant as a plant bioreactor. Any number of physiological or genetic tags would be suitable, and readily identified by one of skill in the art. Examples of physiological "tags" that could be introduced include marker genes such as the green fluorescent protein gene, the firefly luciferase gene and the GUS gene.

Marker genes that alter the physical appearance of the plant may also be used as identifying tags. Examples include increased or decreased length of stems and/or alterations to color. Furthermore, a number of resistance phenotypes may also be used to identify the plant bioreactors. Genes encoding resistance to pests such as bacterial, fungal or nematode pests have been identified in the art, and would be suitable as "tags".

In addition, a genetic sequence itself may comprise the tag, referred to herein as "DNA barcoding". Tagging in this manner is done by introducing a known non-coding polynucleotide sequence into the plant. The tag may then be amplified from the plant using known PCR primers. Plants may then be identified as bioreactors according to the present invention by the presence of a particular size amplicon after the PCR reaction. Further discrimination, for example between types of plant bioreactor, may be achieved by altering the polynucleotide sequence of the DNA barcode in the region between the PCR primers. In this way, the sequence of the bacrocode may be elucidated using automated sequencing techniques to determine the exact identity of the plant. This technique allows for a generic test to identify all plant bioreactors, and allows further discrimination to identify the type of bioreactor based on the sequence of the DNA barcode.

The genetic sequences comprising or encoding the "tag" may be introduced to the plant using the methods hereinbefore described. The tag may be introduced on the same construct as the biosynthetic gene, or may be independently introduced. If introduced independently, the tage may be introduced on a different construct at the same time as transformation with the biosynthetic gene, or introduced to the plant before or after the biosynthetic gene.

Accordingly, the present invention contemplates a plant suitable for use as a bioreactor that has been tagged with a genetic sequence which encodes or comprises a genotypic or phenotypic feature that allows differentiation of the plant bioreactor from a wild-type plant.

Preferably the plant is a C4 grass, and more preferrably, the plant is sugarcane.

The plant-based bioreactor system of the present invention is useful in enabling the production of molecules such as PHAs, pHBA, vanillin, sorbitol, indigo, fructans, lactic acid, adipic acid, 1,3-propanediol, 2-phenylethanol, inter alia, by a number of different parties such as different commercial entities. The present invention extends, therefore, to a data processing system to monitor the use of the plants and/or the production of target molecules.

Accordingly, another aspect of the present invention contemplates a method for generating a target molecule in a sucrose-accumulating plant, said method comprising:
(i) providing a plant or cells of a plant to a party; and
(ii) permitting the party to generate and harvest molecules from said plant or cells of said plant receiving and processing data from said party.

The data received from the party includes, for example, numbers of plants grown and/or harvested, the types of genetic constructs introduced into the cells and/or income received from sale of the products.

The present invention is further described by the following non-limiting Examples.

EXAMPLE 1

Materials

Restriction digests, DNA ligations and all other DNA manipulations were performed as described in Sambrook, et al., Molecular Cloning, A Laboratory Manual, $2^{nd}$ edition, Cold Spring Harbor Press, 1989.

EXAMPLE 2

Cloning of the phaC1 Gene from P. aeruginosa

The phaC1 gene targeted to plant peroxisomes inserted into pART27 as an EcoRI/XbaI fragment, was obtained from Y. Poirier (University of Lausanne, Switzerland). In order to express the gene in sugarcane, it was excised with the said enzymes, end-filled with T4 DNA polymerase (Promega) and inserted into the SmaI site of pUBI-MCS-Nos. To achieve targeting of the phaC1 gene product to mitochondria and plastids, the gene is modified as described below.

EXAMPLE 3

Generation of Genetic Constructs (a) Constructs Comprising Sequences Encoding PHB-synthesizing Enzymes Constructs containing the phaA, phaB and phaC genes from *Ralstonia eutropha* targeted to plastids and cloned in pUC18 as XbaI-SacI fragments were obtained from Y. Poirier (University of Lausanne, Switzerland).

The phaA, phaB and phaC genes derived from *Ralstonia eutropha* were cloned into the vector pU3z. This vector is a derivative of pGEM3 (Promega) containing the maize polyubiquitin promoter and nos terminator from *A. tumefaciens*, and works well as an expression vector in sugarcane. All genes were amplified/modified using the polymerase chain reaction (PCR) prior to insertion into pU3z except phaC1, which was blunt-end cloned into the same vector. All constructs used for plant transformation are listed below. Where inserts are modified, they are sequenced in full to ensure quality.

PCR modifications were performed as follows. Platinum Pfx (registered trademark) DNA polymerase, 10× buffer and PCR-enhancer were obtained from Invitrogen. Final concentrations were one unit of polymerase per reaction, 1× buffer and enhancer, 2 mM $Mg^{2+}$, 0.2 mM dNTP, 0.4 μM of each primer. All primers were purchased from Geneworks, Australia. Reactions were performed in a MJC PTC-100 thermal cycler. The profile was initial denaturation at 96° C. for 5 min, followed by 35 cycles of 94° C. for 30 seconds, 42° C. for 30 sec and 72° C. for 2.5 min. a final extension step of 72° C. for 10 min preceded a final hold at 4° C. Table 1 lists primers used in PCR reactions.

TABLE 1

| NAME | SEQUENCE | | POSITION, GENE, TARGET |
|------|----------|---|------------------------|
| TphaF | $N_6$ggatccatggcttctatgatatcct | [SEQ ID NO:34] | 5', phaA-C, plastid |
| PhaF | $N_6$GGATCCATGACTGACGTTGTCATC | [SEQ ID NO:35] | 5', phaA, cytosol |
| PhbF | $N_6$GGATCCATGACTCAGCGCATTGCG | [SEQ ID NO:36] | 5', phaB, cytosol |
| PhcF | $N_6$GGATCCATGGCGACCGGCAAAGGC | [SEQ ID NO:37] | 5', phaC, cytosol |
| PhaR | CTGAGTCATGTCCACTCC | [SEQ ID NO:38] | 3', phaA, cytosol and plastid |
| PhbR | CTGCCGACTGGTGGAACC | [SEQ ID NO:39] | 3', phaB, cytosol and plastid |
| PhcR | GAAGCGTCATGCCTTGGC | [SEQ ID NO:40] | 3', phaC, cytosol and plastid |
| PhaC1CF | $N_6$GGATCCATGAGCCAGAAGAAC | [SEQ ID NO:41] | 5', phaC1, cytosol and mitochondia |

TABLE 1-continued

| NAME | SEQUENCE | | POSITION, GENE, TARGET |
|---|---|---|---|
| PhaC1CR | N₆GGTACCTCATCGTTCATGCACG | [SEQ ID NO:42] | 3', phaC1, cytosol and plastid |
| PhaC1PF | N₆CCCGGGTGAGCCAGAAGAACAATAAC | [SEQ ID NO:43] | 5', phaC1, plastid |
| PhaJF | GGATCCATGAGCGCACAATCCCTGG | [SEQ ID NO:44] | 5', phaJ, peroxisome |
| PhaJR | AAGCTTTTGAAGGCAGCTTGACCACGGC | [SEQ ID NO:45] | 3', phaJ, peroxisome |
| PhaGF | CCCGGGTGAGGCCAGAAATCGCTGTAC | [SEQ ID NO:46] | 5', phaG, plastid |
| PhaGR | GGTACCTCAGATGGCAAATGCATGC | [SEQ ID NO:47] | 3', phaG, plastid |
| SSP-F | NNGAGCTCGATGGGAGGTGCTCGAAGACATATTACC | [SEQ ID NO:48] | 5', stem-specific promoter |
| SSP-R | NNGGATCCTGTACTAGATATGGCAGC | [SEQ ID NO:49] | 3', stem-specific promoter |

Approximately 10 ng of construct was used as template in each reaction.

Following PCR, fragments were gel purified and cloned into the BamHI and SmaI sites of pUSN in the correct orientation between the maize polyubiquitin promoter and the nos-terminator from *A. tumefaciens*. Plasmid constructs were fully sequenced and purified by anion-exchange chromatography (Qiagen, Australia) prior to transformation into callus tissue.

(b) Constructs Comprising Marker Sequences

Two plasmids were obtained from the CSIRO, Brisbane, Australia. The first comprised the <pUbi-gfp-nos> construct, which carries the green fluorescent protein (GFP) from *Aquorea victoria* under the control of the same promoter as above. The second plasmid, designated "pEmuKn", harbours an aphA gene (neomycin phosphotransferase) under the control of the Emu promoter. These plasmids were used without any further modification.

EXAMPLE 4

Sugarcane Transformation (a) Generation of Embryogenic Callus Tissue

Embryogenic callus of the sugarcane variety Q117 was established, as described in Bower et al., *Molec. Breeding* 2: 239-249, 1996. Briefly, embryogenic callus was established by excision of inner leaf whorls from cane tops 2-5 cm above the apical meristem. Disks of approximately 2 mm thickness were placed on MSC₃ medium that contains 3 µg/ml 2,4-Dichlorophenoxy-acetic acid (2,4-D) and incubated at 28° C. in the dark for 2-5 months, with fortnightly subculturing. In order to avoid problems associated with stress arising from the tissue culture process, such as somaclonal variation, unused callus tissue was discarded after 6 months in culture.

Prior to transformation, embryogenic callus was transferred to osmotic MSC₃, as previously described (Bower et al., 1996, supra)

(b) Bombardment of Callus Tissue

DNA was coated onto tungsten particles (Sylvania M-10) and embryogenic callus bombarded as described by Bower et al. (1996, supra).

Callus tissue was co-transformed with up to five individual constructs, plasmid solutions being mixed to give equimolar concentrations to facilitate co-integration and expression of genes required for PHB production. There is a strong correlation between co-transformation and co-integration of constructs into the genome of plant hosts. The combinations of constructs introduced into Q117 callus and the target for products of each pha gene are shown in the following Table 2, wherein "cyt"=cytosol, "pla"=plastid, "mito"=mitochondrion and "perox"=peroxisome:

TABLE 2

COMBINATION AND TARGETING OF pha GENE PRODUCTS phaA (cyt), phaB (cyt), phaC (cyt), Ubi-GFP, Emu-Kn phaA (pla), phaB (pla), phaC (pla), Ubi-GFP, Emu-Kn phaA (cyt), phaB (cyt), phaC1 (cyt), Ubi-GFP, Emu-Kn phaC1 (perox), Ub-GFP, Emu-Kn phaA (cyt), phaB (cyt), phaC (cyt), phaC1 (perox),
phaA (pla), phaB (pla), phaC (pla), phaG (pla),
phaC1 (pla), Ubi-GFP, Emu-Kn phaC1 (perox), phaA (pla), phaB (pla), phaC (pla),
phaG (pla), phaC1 (pla), Ubi-GFP, Emu-Kn phaA (pla), phaB (pla), phaC (pla), phaG (pla),
phaC1 (pla), Ubi-GFP, Emu-Kn phaG (pla), phaC1 (pla), Ubi-GFP, Emu-Kn phaA (mito), phaB (mito), phaC (mito), Ubi-GFP, Emu-Kn Microprojectile bombardment was performed as described in Bower et al. (supra), except that, to improve transformation efficiencies, the vacuum chamber was evacuated to −100 kPa atmospheric pressure and particles accelerated by a helium pulse of 3000 kPa for 100 ms.

(c) Selection of Transformed Material

Following bombardment, callus was allowed to recover for one hour, before being placed onto MSC₃ medium supplemented with 50 µg/ml Geneticin (registered trademark) (Invitrogen).

Putatively transformed tissue was screened for the expression of GFP and resistance to the antibiotic geneticin. Bombarded callus was examined for the presence of cells expressing GFP 7 days after transformation and stained in vivo with Nile Red, a sensitive in vivo stain specific for intracellular lipids, as previously described (Taguchi et al., *FEMS Microbiol. Lett.* 198: 65-71, 2001; Greenspan, et al., 1985, supra). For both techniques, an Olympus SZX 12 stereomicroscope equipped with GFP excitation and emission filters was used.

Dump

Antibiotic selection was continued for 3 months in the dark at 28° C. and continued during plant regeneration. Only calli expressing both selectable markers were allowed to regenerate into plantlets.

(d) Regeneration of Transformed Sugarcane Plantlets

For plant regeneration, callus was transferred to medium without 2,4-D and incubated at 24-26° C. under illumination. Plantlets appeared after 2-4 months and were transferred to potting mix and kept in mini-glasshouse (Yates, Australia) for one week prior to transfer to glasshouse facilities.

EXAMPLE 5

Determination of Quantity and Composition of PHA Produced

If the desired PHA is PHB, quantification in transgenic sugarcane is conducted by HPLC, as described by Karr et al., *Applied and Environmental Microbiology* 46: 1339-1344, 1983. This method allows for the analysis of plant extracts with minimal handling. This technique is illustrated in Figure *.

For other PHAs, molecular characterization and quantification of PHA content in transgenic plants is carried out using gas chromatography analysis.

For GC analysis, PHA was separated from homogenized leaf samples by chloroform extraction, followed by methanol extraction, to remove lipids other than PHA. The polymer was then purified further by acetone extraction.

Transesterification of plant extracts was performed as described in Braunegg et al., *Eur. J. Appl. Microbiol. Biotechnol.* 6: 29-37, 1978 modified by using boron trifluoride rather than sulfuric acid as catalyst and decreased incubation time to 1 hr. Gas chromatography analysis was performed using a Varian 3300 chromatograph, as described by Slater et al., in *J. Bacteriol.* 180: 667-73, 1998. Purified PHB (Coparsucar, Brazil) and methyl-3-hydroxybutyrate (Sigma) were used as positive controls either pure or spiked into negative control plant extracts. Modifications to this method, namely using Boron trifluoride rather than sulfuric acid as catalyst and decreasing incubation times to 1 hour, in addition to minor modifications to instrument parameters, were found to improve peak resolution.

Millenium software (Waters Corp., Milford, Mass.) is used to quantify amounts of PHAs produced, by comparison of peak areas from plant extracts with those from standards of known concentration. GC-MS is used to determine the composition of PHAs produced in transgenic sugarcane, as different hydroxy-alkanoates have different mass-spectrum signatures.

EXAMPLE 6

Production of PHB in Transgenic Sugarcane Leaves

In plants accumulating high amounts of PHA, gene copy number, transcription levels and amount of protein are determined using standard molecular biology techniques. Gene copy numbers are determined by Southern blot analysis of genomic DNA from transformed plants producing PHAs. Transcription levels will be evaluated by northern blot analysis of RNA from transgenic plants and gene product levels examined by western blot analysis of protein extracts using antibodies against the gene products. The antisera were obtained from Prof Y. Poirier (University of Lausanne, Switzerland).

EXAMPLE 7

Targeting of PHB Production to Non-plastid Sugarcane Organelles

The constructs pUbi-phaA, pUbi-phaB and pUbi-phaC comprising the phaA, B and C genes, respectively, transcriptionally fused to the aforementioned maize polyubiquitin promoter were digested with BamHI and dephosphorylated with shrimp alkaline phosphatase (Promega, Maddison, USA). A BglII/BamHI fragment of the plasmid sB-pma4-35S-β-del-GFP, containing the leader sequence and first 12 amino acid residues of the β subunit of the *Nicotiana plumbaginifolia* mitochondrial F1-ATPase (Chaumont et al., *PMB* 24: 631-664, 1994), was ligated with pUbi-phaA, B or C cut with BamHI. These constructs target PhaA, B or C to the mitochondria with high efficiency. For targeting of pha gene products to other organelles, the genes were modified and ligated into plasmids already containing the required DNA targeting sequences.

Sugarcane was transformed with these constructs, using the aforementioned methods.

Transgenic plants thereby generated are screened for PHB production, using the aforementioned techniques.

EXAMPLE 8

Production of PHB in Transgenic Sugarcane Stems

Plasmids pUbi-phaA, pUbi-phaB, pUbi-phaC, pUi-TP-phaA, pUbi-TP-phaB and pUbi-TP-phaC were digested with BamHI/EcoRI to release the pha genes with or without the aforementioned plastid leader sequence at the 5' end, and with the aforementioned NOS terminator at the 3' end. These fragments were ligated into the vector pSSP cut with BamHI/EcoRI. pSSP is a derivative of the vector p67G420 (supplied by Prof. R Birch, University of Queensland). p67G-420 houses, immediately upstream of a unique BamHI site, a stem-specific promoter isolated from sugarcane. To obtain pSSP, a consensus ribosome binding site was removed from the 3' end of the promoter in the following way.

The promoter was PCR amplified, using the aforementioned technique, with the primers SPP-F and SPP-R (see Table 1), incorporating BamHI and SacI sites into the 5' and 3' ends of the promoter, repectively. The PCR product was digested with BamHI and SacI and then religated into the backbone of p67G_420 digested with the same enzymes. The promoter was fully sequenced to confirm quality. The resulting constructs, which were fully sequenced to confirm quality, drive gene expression in the stems and target the gene products to either the cytosol or the plastids. pSSP was linearized with BamHI and dephosphorylated with shrimp alkaline phosphatase, and ligated with the aforementioned BglII/BamHI fragment of the plasmid sB-pma4-35S-β-del-GFP, giving the intermediate vector pSSP-Tm. BamHI/EcoRI fragments of pUbi-phaA, pUbi-phaB and pUbi-phaC were ligated into pSSP-Tm. The resulting constructs, which were fully sequenced to confirm quality, drive gene expression in the stems and target the gene products to the mitochondria Sugarcane was tranformed with these constructs using the aforementioned methods.

Transgenic plants thereby generated are screened for PHB production, using the aforementioned techniques.

EXAMPLE 9

Detection of PHB in Chloroplasts of Transgenic Sugarcane

Transgenic plants expressing PHB biosynthetic genes were produced according to the methods described herein. Accumulation of PHB in the plastid was assessed using both HPLC and transmission electron microscopy.

Figure * shows a graphical representation of the detection of PHB in chloroplasts of transgenic sugarcane. Panels A-C indicate detection of PHB using HPLC. Panel A is a wild-type sugarcane control; Panel B is the plant in A spiked with PHB Panel C depicts a transgenic sugarcane line accumulating PHB in the plastids. Arrows point to the elution point of crotonic acid, which is the product of acid-hydrolsis of PHB. The insert in Panel C shows that the peak at 30 min in C has the same spectrum as crotonic acid.

Figure 4:
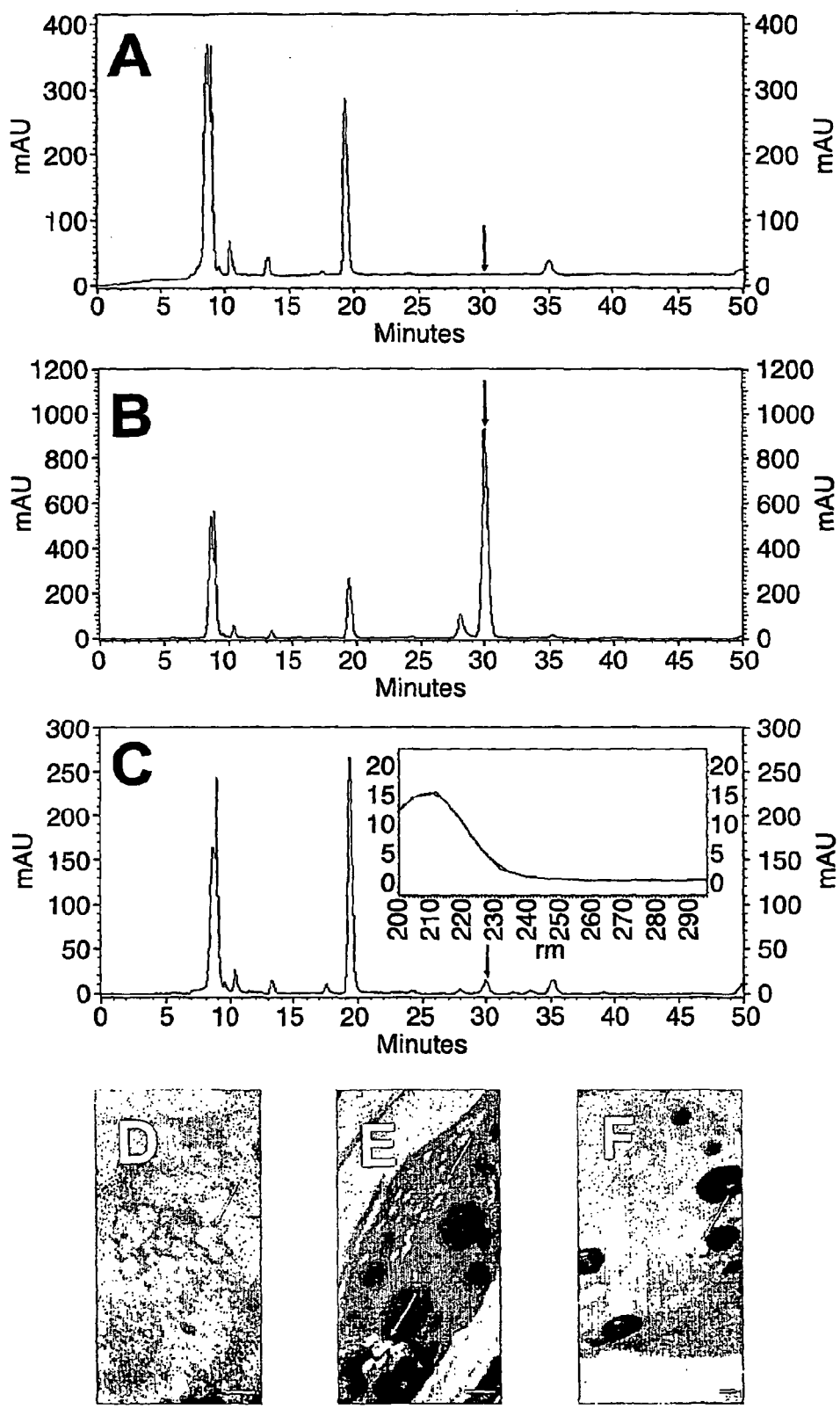
FIG. 4 shows a graphical representation of the detection of PHB in chloroplasts of transgenic sugarcane. A-C: Detection of PHB by HPLC. A: WT sugarcane (s/c) −ve control; B: sample in A spiked with PHB; C: plastid-targeted, PHB +ve s/c line. Arrows: elution point of crotonic acid (PHB breakdown product). Insert in C shows that the peak at 30 min in C has the same spectrum as crotonic acid. D-F: Detection of PHB granules by transmission electron microscopy. D: Chloroplast (c/p) of mesophyll cell of PHB +ve $Arabidopsis$ control; E: c/p of mesophyll cell of PHB +ve s/c line; F: c/p of bundle-sheath cell of same line in E. Scale bars=200 nm.

Panels D-F in FIG. 4 show the detection of PHB granules in plants by transmission electron microscopy. Panel D shows a positive control comprising a chloroplast from a mesophyll cell in a PHB +ve *Arabidopsis* plant (Bohmert et al. 2000). Panel E is a electron-micrograph showing PHB granules in a chloroplast of a mesophyll cell from a PHB-producing sugarcane plant. Panel F shows PHB granules in a chloroplast of a bundle-sheath cell from the same plant line in E. Scale bars=200 µm.

EXAMPLE 10

Agronomic Performance of PHB-producing Sugarcane Lines

Four transgenic sugarcane lines expressing the PHB biosynthesis genes of *Ralstonia eutropha* were grown for 3 months in a randomised glasshouse plot. Control plants comprised GFP-expressing and tissue-culture-regenerated wild-type plants. PHB content was assessed in lamina from the tips of mature leaves and quantified by HPLC analysis.

The results are show in FIG. 5. The production of PHB in sugarcane at up to 1.6% of leaf dry-weight did not reduce agronomic performance compared with GFP-expressing and wild-type control plants. Data are the mean±SE (n=3). DW=dry-weight.

EXAMPLE 11

Affect of PHB Production on Sugarcane Sugar Accumulation

The plants assessed in Example 10, ie. PHB producing, GFP expressing and wild-type sugarcane, were further examined for their sucrose, glucose and fructose concentrations to determine the effect of PHB production on sugar content.

Figure 6:
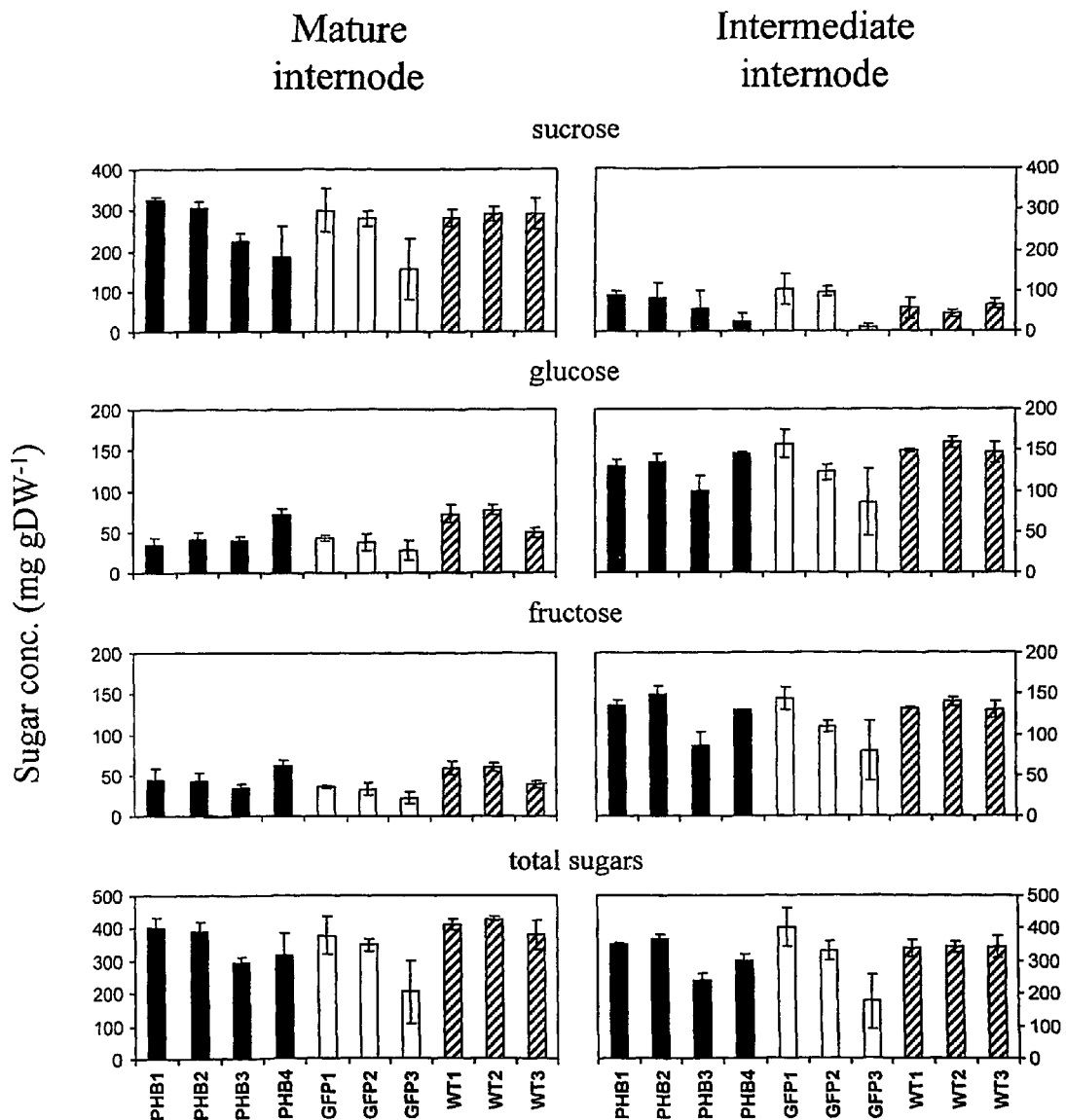
FIG. 6 shows the affect of PHB production on sugarcane sugar accumulation. Mature-(A-D) and intermediate-aged (E-H) stem internodes from the PHB producing (solid bars), GFP expressing (open bars) and WT (hatched bars) sugarcane plants in FIG. 5 were assayed for sucrose, glucose and fructose concentrations. Data are the mean±SE (n=3). DW=dry-weight.
Figure 7:
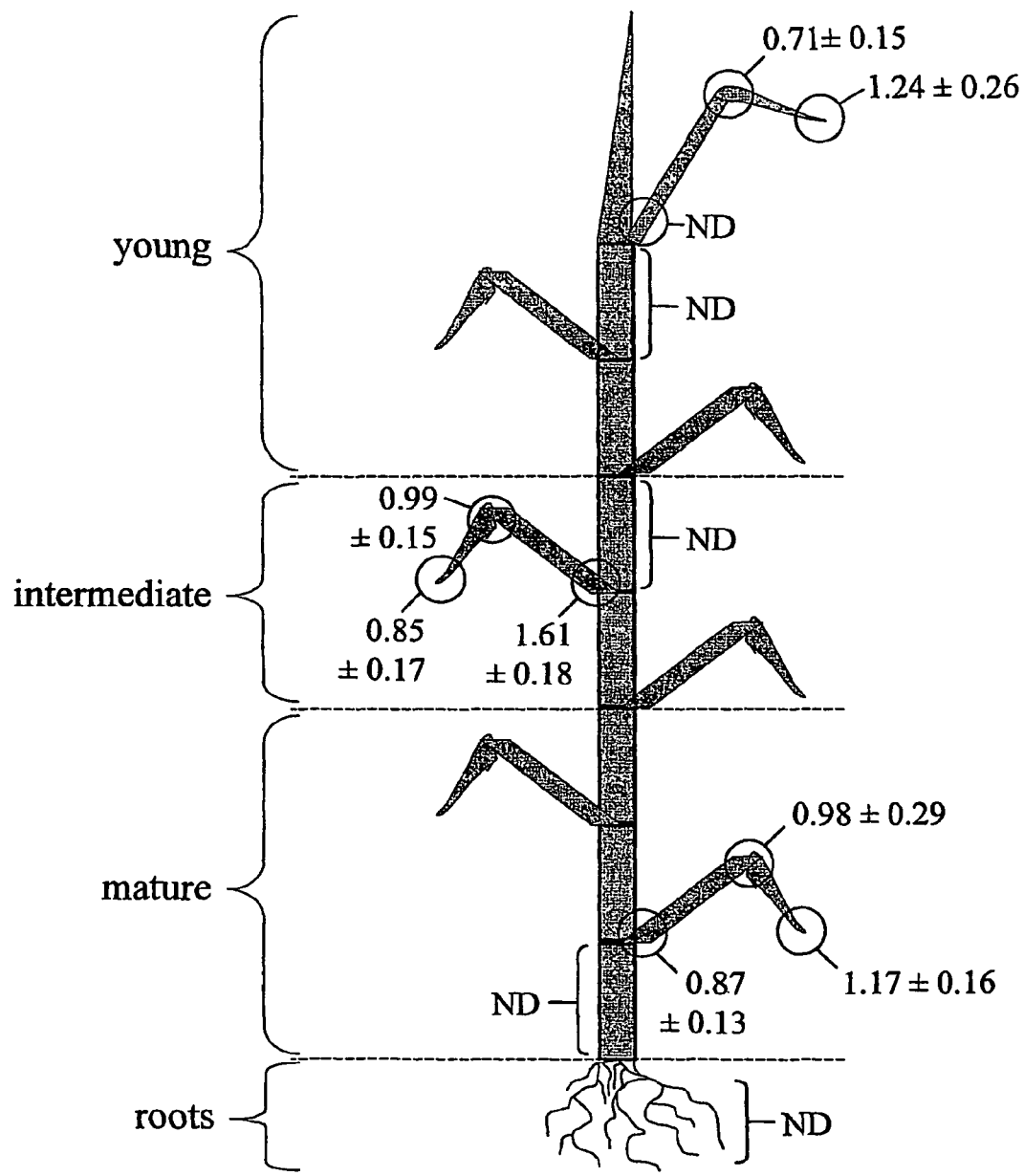
FIG. 7 is a graphical representation showing the distribution of PHB throughout a PHB-producing sugarcane line. The distribution of PHB throughout transgenic sugarcane line PHB3 in FIG. 5 was determined by HPLC analysis. Samples were taken from: lamina of the tip, midpoint and base of young, intermediate and mature leaves; rind+pith of young, intermediate and mature stem internodes; and roots. Data are the mean % of leaf DW as PHB±SE (n=3). ND=not detected.

The results are shown in FIG. 6. It was observed that PHB accumulation of up to 1.6% of leaf dry-weight did not reduce sucrose, glucose, fructose or total sugar content in PHB producing (solid bars) plants compared to GFP-expressing (open bars) and wild-type (hatched bars) controls. Data are the mean±SE (n=3). DW=dry-weight.

EXAMPLE 12

Distribution of PHB in PHB-producing Sugarcane

The distribution of PHB throughout transgenic sugarcane line PHB3 was determined by HPLC analysis. Samples were taken from:
 (i) lamina of the tip, midpoint and base of young, intermediate and mature leaves;
 (ii) combined rind and pith of young, intermediate and mature stem internodes; and
 (iii) roots.

The PHB content data are presented as the mean percentage of leaf dry-weight±SE (n=3). ND=not detected.

EXAMPLE 13

Production of Vanillin in Sugarcane

Vanillin (4-hydroxy-3-methoxybenzaldehyde) would be produced as a co-product with sucrose. Sucrose yield is expected to decrease in direct proportion to the amount of vanillin produced.

Initially, genes for the vanillin biosynthetic pathway from a known source are cloned. These genes are then expressed in sugarcane, including any tailoring of the expression pattern as required. The product is produced as a glucose conjugate, which is stable.

A number of biological pathways have been discovered for the biosynthesis/biodegradation of vanillin. At least 2 of these have substrates which are available in plants.
1) 3-Dehydroshikimic acid is produced as an intermediate in the shikimate pathway. A pathway has been identified which converts this substrate via 3-Dehydroshikimate dehydratase to protocatechuic acid then to vanillic acid via Catechol-o-methyltransferase and finally to vanillin via Aryl aldehyde dehydrogenase.
2) Ferulic acid is a secondary metabolite of the phenylpropanoid pathway involved in lignin synthesis. It is converted in planta to feruloyl-CoA by feruloyl-CoA synthetase which in turn is converted to vanillin by enoyl-CoA hydratase/aldolase.

Glucosylation of the product in vivo is expected to detoxify the product Accordingly, inducible expression should not be required. The maxiumum level of production is determined by the flux through the phenylpropanoid pathway. However, Sugarcane has a productive phenylpropanoid pathway and should adapt readily to increased demands placed on it for synthesis of vanillin.

EXAMPLE 14

Production of Sorbitol in Sugarcane

*Zymomonas mobilis* is able to produce sorbitol from sucrose or a mixture of glucose and fructose in a one-step reaction catalysed by the glucose-fructose oxidoreductase GFOR (Genbank accession no. Z80356, M97379). The glucose is oxidized to gluconolactone while the fructose is reduced to sorbitol.

Sorbitol production in sugarcane could be achieved by using GFOR This involves constructing an expression cassette by fusing GFOR to the maize polyubiquitin promoter and nopaline synthase terminator and introducing the cassette into sugarcane callus by biolistic transformaton. The *Z. mobilis* GFOR is not membrane-bound and resides in the periplasm and should work equally well as a cytosolic enzyme in sugarcane.

Sorbitol production is unlikely to be toxic in sugarcane since sorbitol is found in numerous fruits (apples, pears, plums, berries, cherries). Sorbitol functions physiologically to regulate osmotic stress hence extremely high levels may be detrimental. Vacuolar storage may circumvent this problem.

The threshold level at which sorbitol is deleterious to the host may be determined by growing sugarcane callus on solid medium containing sorbitol.

A potential large-scale system for the recovery of sorbitol from sugarcane involves adding an aqueous organic salt solution, mixing and then separating a salt water phase from a polyol-rich phase (see international patent application WO210252).

EXAMPLE 15

Indigo Production in Sugarcane

The chief incentive to use sugarcane as an indigo biofactory is to provide a manufacturing route that will produce relatively inexpensive indigo from a renewable feedstock.

Indigo production by microbial fermentation has been demonstrated by expressing the genes that mediate indigo formation in *E. coli* (Drewlo 2001, Berry 2002). The pigment is derived by converting endogenous tryptophan to indole using the *Enterobacter aerogenes* tryptophanase or L-tryptophan indole lyase EC 4.1.99.1 (Genbank accession no. D14297). Subsequently the indole is converted to indigo via two possible reactions.

Route A: *Pseudomonas putida* napthalene dioxygenase (Genbank accession no. M83949)

Route B: *Ralstonia eutropha* bec gene (Genbank accession no. AF306552)

Indigo production in sugarcane would involve constructing an expression cassette by fusing the aforementioned genes to the maize polyubiquitin promoter and nopaline synthase terminator and introducing the cassette into sugarcane callus by biolistic transformaton. Both route A and B should be tested if possible. Tryptophan is a product of the plant shikimate pathway, which is responsible for synthesizing lignin precursors. The cloned genes will need to be plastid-targeted since the shikimate pathway reactions reside in this compartment. The available metabolic flux in this pathway is expected to be significant.

EXAMPLE 16

Production of Fructans in Sugarcane

Naturally occurring fructans may contain 10 to 100,000 fructose residues. Bacteria produce the larger fructans whilst those occurring in plants are smaller. The larger polymers are desirable beause they are less soluble in water and consequently easier to extract. Larger fructans will not affect the osmotic pressure in the cell to the same degree as smaller molecules. Therefore it is possible to store greater quantities of fructan before the cell is affected.

Numerous bacterial fructosyltransferases or levansucrases have been characterized (Genbank accession no. AY150365, *Bacillus subtilis*). These enzymes catalyze the transfer of the D-fructosyl residue from sucrose to the β-2,6-linked residues of fructan.

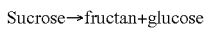

Sucrose→fructan+glucose

Fructan production in sugarcane would be achieved by constructing an expression cassette containing levansucrase, the maize polyubiquitin promoter and nopaline synthase terminator and introducing the cassette into sugarcane callus by biolistic transformaton.

Levansucrase will probably require apoplastic or vacuolar targeting to maximize access to substrate for conversion.

Fructan may then be recovered from sugarcane juice by ethanol precipitation followed by vacuum drying.

EXAMPLE 17

Lactic Acid Production in Sugarcane

The production of Lactic acid (2-Hydroxypropanoic acid) in sugarcane proceeds with the following steps:
  (i) Obtain or clone lactate dehydrogenase (LDH) from a number of sources, such a *Lactobacillus* spp. bacterium.
  (ii) Expression of the gene in sugarcane, with any necessary changes to the sequence such as codon preference. It is preferred that the introduced gene is expressed in the cytosol, therefore no targeting is required.
  (iii) Regenerate plants and evaluate for lactate (or derivative) production.

Lactic acid build-up may cause deleterious effect on cells. There are several ways by which cells can deal with this. One is to remove the acid either by diffusion or transport. The other is modification of the offending chemical and export into the vacuole. Glycosylation is a major signal for this process and lactic acid possesses two potential glycosylation sites.

Traditionally, lactic acid purification has been a complex chemical process. However, recent advances have simplified this process and made it significantly cheaper. It is anticipated that lactic acid can be removed from the post-crushing millstream without great difficulty or extensive modification of existing structures. It is anticipated that the extraction process will be product dependent.

EXAMPLE 18

Adipic Acid Production in Sugarcane

Adipic acid may be produced in sugarcane by one of two approaches.

I. Synthesis from Cis, Cis-Muconic Acid

Adipic acid has been produced in transgenic *E. coli* using the metabolic pathway illustrated below. Three genes were introduced into *E. coli* to produce cis, cis-muconic acid that was subsequently purified from the fermentation broth and converted to adipic acid by catalytic hydrogenation (step g, 10% Pt/C, $H_2$, 3400 kPa, 25° C.). This final step has a 97% conversion efficiency.

The synthesis of cis, cis-muconic acid in sugarcane involves making use of the shikimate pathway. In order to use the shikimate pathway to produce cis, cis-muconic acid the following biosynthetic enzymes, or homologs thereof are introduced into sugarcane:

*Klebsiella pneumoniae* 3-dehydroshikimate dehydratase (aroZ)-enzyme d

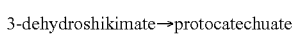

3-dehydroshikimate→protocatechuate

*Klebsiella pneumoniae* protocatechuate decarboxylase (aroY)-enzyme e

Protocatechuate→catechol

*Acinetobacter calcoaceticus* catechol 1,2-dioxygenase (catA)-enzyme f

Catechol+$O_2$→cis, cis-muconic acid

Introduction of these genes into sugarcane involves constructing an expression cassette by fusing the genes described above to the maize polyubiquitin promoter and nopaline synthase terminator and introducing the cassette into sugarcane callus by biolistic transformation. Catechol is probably produced in most plants, and therefore, it may be unnecessary to clone additional copies of 3-dehydroshikimate dehydratase or protocatechuate decarboxylase. The cloned gene(s) are plastid-targeted since the shikimate pathway reactions reside in this compartment.

The shikimate pathway executes a central role in plant secondary metabolism. This is one of the most active pathways in plants in terms of carbon flux owing to the fact that it is the source of lignin precursors. This makes it an attractive candidate for metabolic engineering.

II. Synthesis from Petroselinic Acid

Bio-based adipic acid can be obtained through ozonolysis ($O_3$) of petroselinic acid (18:1 $\Delta^{6\ cis}$), as shown in FIG. 10. The coproduct lauric acid is also a potential source of feedstock for detergent manufacture.

The seed oil of the coriander spice plant contains 80-90% petroselinic acid. A 36 kDa putative acyl-ACP desaturase (Genbank accession no. M93115) has been identified from coriander seed extracts and the corresponding cDNA was able to confer the ability to produce petroselinic acid in tobacco callus (Cahoon 1992). Petroselinic acid was quantified from extracted calli by gas chromatography and GC-MS (to determine double bond position). Tobacco does not normally produce petroselinic acid hence the successful expression of the cDNA in tobacco suggested that this desaturase was sufficient for petroselinic acid formation. This also infers that it may be feasible in sugarcane.

The metabolic pathway for producing petroselinic acid is unclear, however, evidence suggests that it is formed by the desaturation of palmitoyl-ACP by the 36 kDa desaturase followed by elongation to form petroselinic acid (Cahoon 1994).

16:0-ACP→16:1 $\Delta^4$-ACP→18:1 $\Delta^6$-ACP

Recent studies have identified a 3-ketoacyl-ACP synthase (Genbank accession no. AF263992) associated with the two-carbon elongation of 16:1 $\Delta^4$-ACP.

Cis, cis-muconic acid in sugarcane juice would be converted to adipic acid by catalytic hydrogenation. The adipic acid in the resultant solution can be recovered by solvent extraction. The solution is contacted with chloroform or methylene chloride and the adipic acid recovered in the aqueous fraction. The aqueous fraction would then be evaporated to yield crystalline adipic acid.

EXAMPLE 19

Production of 1,3-propanediol (1,3-PD) in Sugarcane 1,3-PD is a natural product of glycerol fermentation in a few enterobacteria and clostridia. Fermentation-derived 1,3-PD was not commercially viable for many years due to the high cost of the glycerol feedstock.

The metabolic reactions that convert glycerol to 1,3-PD have been established from *Klebsiella pneumoniae*.

*Klebsiella pneumoniae* glycerol dehydratase (dhaB)

glycerol→3-hydroxypropionaldehyde+$H_2O$

*Klebsiella pneumoniae* 1,3-propanediol oxidoreductase (dhaT)

3-hydroxypropionaldehyde+NADH→1,3-propanediol+NAD

Sugarcane does not naturally produce glycerol therefore the reactions that convert triose phosphates to glycerol must also be engineered into sugarcane.

*Saccharomyces cerevisiae* glycerol-3-phosphate dehydrogenase dihydroxyacetone phosphate+NADH→glycerol-3-phosphate+NAD

*Saccharomyces cerevisiae* glycerol-3-phosphatase glycerol-3-phosphate+ADP→glycerol+ATP Effectively, all four new genes must be cloned into sugarcane to convert it into a 1,3-PD biofactory. These genes will be assembled into an expression cassette containing the maize polyubiquitin promoter and nopaline synthase terminator. The cassette will be introduced into sugarcane callus by biolistic transformation and expression will be targeted to the cytosol. The accumulation of 1,3-PD in plant tissue will be assayed from plant extracts by conventional HPLC.

1,3-PD can be recovered from sugarcane juice by extraction with cyclohexane followed by vaporization of the residual solvent. Alternatively, distillation may be employed. Use of cyclohexane is environmentally unsound and distillation is energy intensive. Consequently, a method has been patented that describes the use of ion exclusion resins to recover 1,3-PD (see international patent application WO 01/73097).

EXAMPLE 20

Production of 2-phenylethanol (2-PE) in Sugarcane

The production of 2-PE in sugarcane would be achieved in a similar way to previous examples. Briefly, cloned genes for the 2-PE biosynthetic pathway, which has previously been determined, would be obtained. Second, these genes would then be expressed in sugarcane, tailoring the expression pattern and codon usage if required. Finally, a stable product, as a glucose conjugate, is expected.

A biological pathway for the biosynthesis of 2-PE is presented in FIG. 11.

The product is produced naturally in roses and hence should not be toxic. Glucosylation of the active group is likely to occur in sugarcane to reduce potential toxicity.

2-PE would be recovered by crushing the cane and refining from juice as for sucrose, and standard production processes for the synthetic form are well established.

2-PE is water-soluble and should be stable for the time normally taken to process sugarcane for sucrose. If sugarcane stores 2-PE as a glucose conjugate then alkaline hydrolysis may be required.

EXAMPLE 21

Characterization of CPL-Expressing and HCHL-Expressing Sugarcane Plants

A chloroplast-targeted version of E. CPL situated between the maize ubi-1 promoter and nos terminator of the expression construct pU3z-mcs-nos, was co-bombarded with a plasmid containing a selectable marker (pUKN) into embryogenic sugarcane callus to yield the UC series of transgenic lines. The UH series of plants was generated in the same manner using an analogous expression construct that contained the ORF of the *P. fluorescens* HCHL gene. To serve as controls for the experiments described below, four non-transgenic lines (TC1-TC4) were also regenerated from the same callus material omitting the transformation and selection steps. The regenerated plants were grown in a greenhouse for four weeks and were then analyzed for pHBA accumulation in leaf tissue using HPLC. Only plants that had higher levels than the control plants (46% and 48% of the population for the UC lines and UH lines, respectively) were included in the analysis shown in FIG. 2.

Not surprisingly, none of the transgenic plants had significantly higher levels of "free" pHBA than the control plants. Similar to the situation reported for tobacco plants expressing CPL (Siebert et al., *Plant Physiol.* 112: 811-819, 1996) or HCHL (Mayer et al., *Plant Cell* 13:1669-1682, 2001), the only two compounds that accumulated were pHBA glucose conjugates, a phenolic glucoside and a glucose ester. Both compounds contained a single glucose molecule that was attached by a 1-O-☐-D linkage to the hydroxyl or carboxyl group of pHBA. The predominant product in all of the plants examined was the phenolic glucoside, which accounted for at least 90% of the pHBA (see below). The mean value for the population was 0.41%+0.04% of dry weight (DW), which is almost 30-fold higher than the mean value for the non-transgenic control plants 0.014%±0.01% DW. More important, the pHBA glucoside content of the best plant was 1.5% DW, which is equivalent to 0.69%-DW-free-pHBA after correcting for the attached glucose molecule. This value is three times higher than the highest value obtained with transgenic tobacco plants expressing a different chloroplast-targeted version of CPL (Siebert et al., supra). The HCHL-expressing sugarcane plants accumulated even higher levels of pHBA. The mean value for total pHBA glucose conjugates in the UH lines was 0.70%+0.07% DW, and the highest level observed at this stage of development was 2.6% DW, which is very similar to the best value reported for transgenic tobacco plants expressing the same enzyme (Mayer et al., supra).

Figure 15:
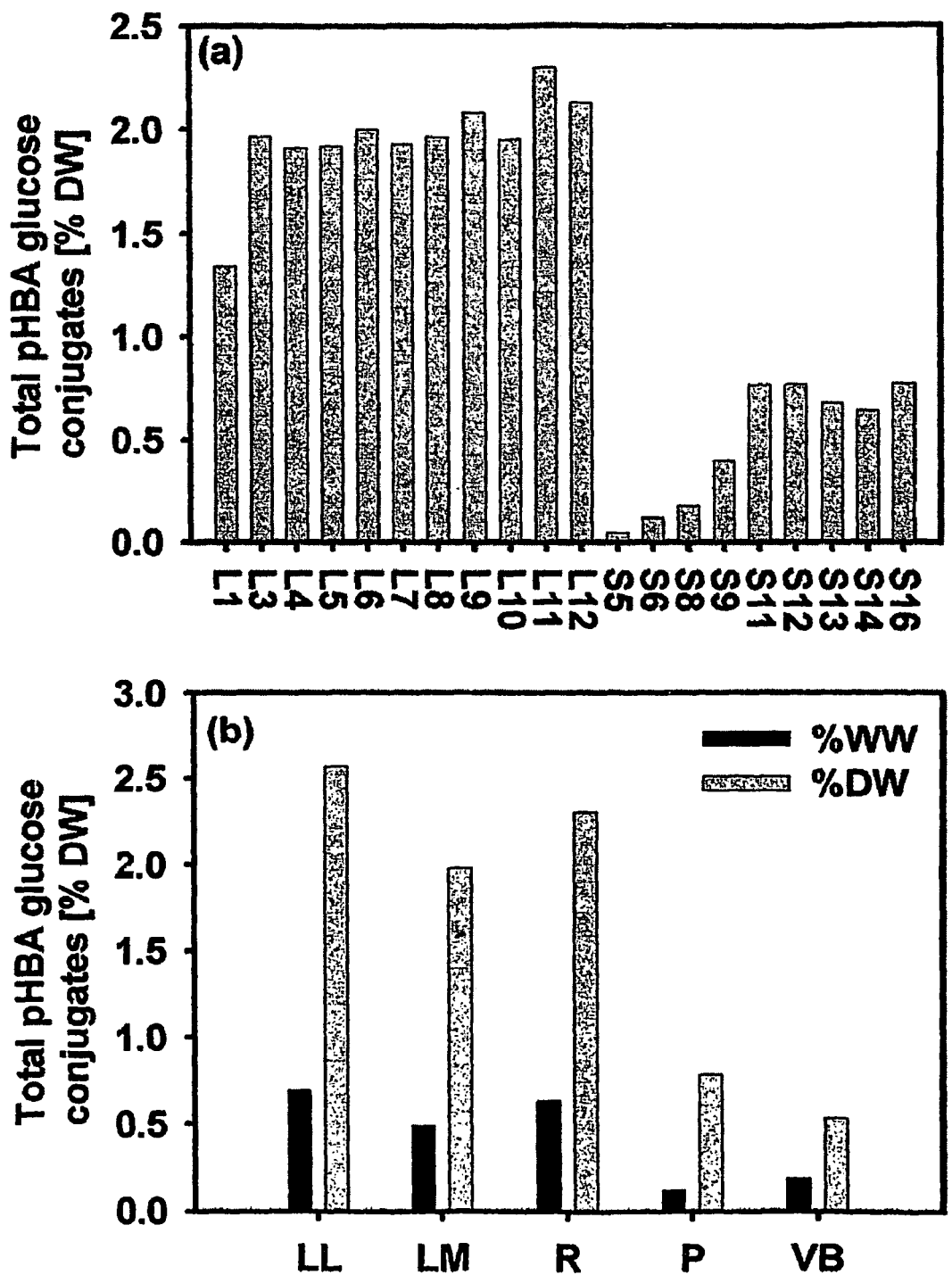
FIG. 15 is a graphical representation showing the distribution pattern of p-hydroxybenozic acid (pHBA) in UH1 at 20 weeks. (a) Leaf and internode pHBA levels are compared. There is generally more pHBA in the leaf than the stalk and the content in older tissue is generally higher than younger tissue. (b) pHBA levels at specific locations in the tissue are compared. The largest quantities of pHBA are found in the leaf lamina and the rind tissue of the stem. (LL=leaf lamina; LM=leaf midrib; R=rind; P=pith; VB=vascular bundles of stem tissue).
Figure 16:
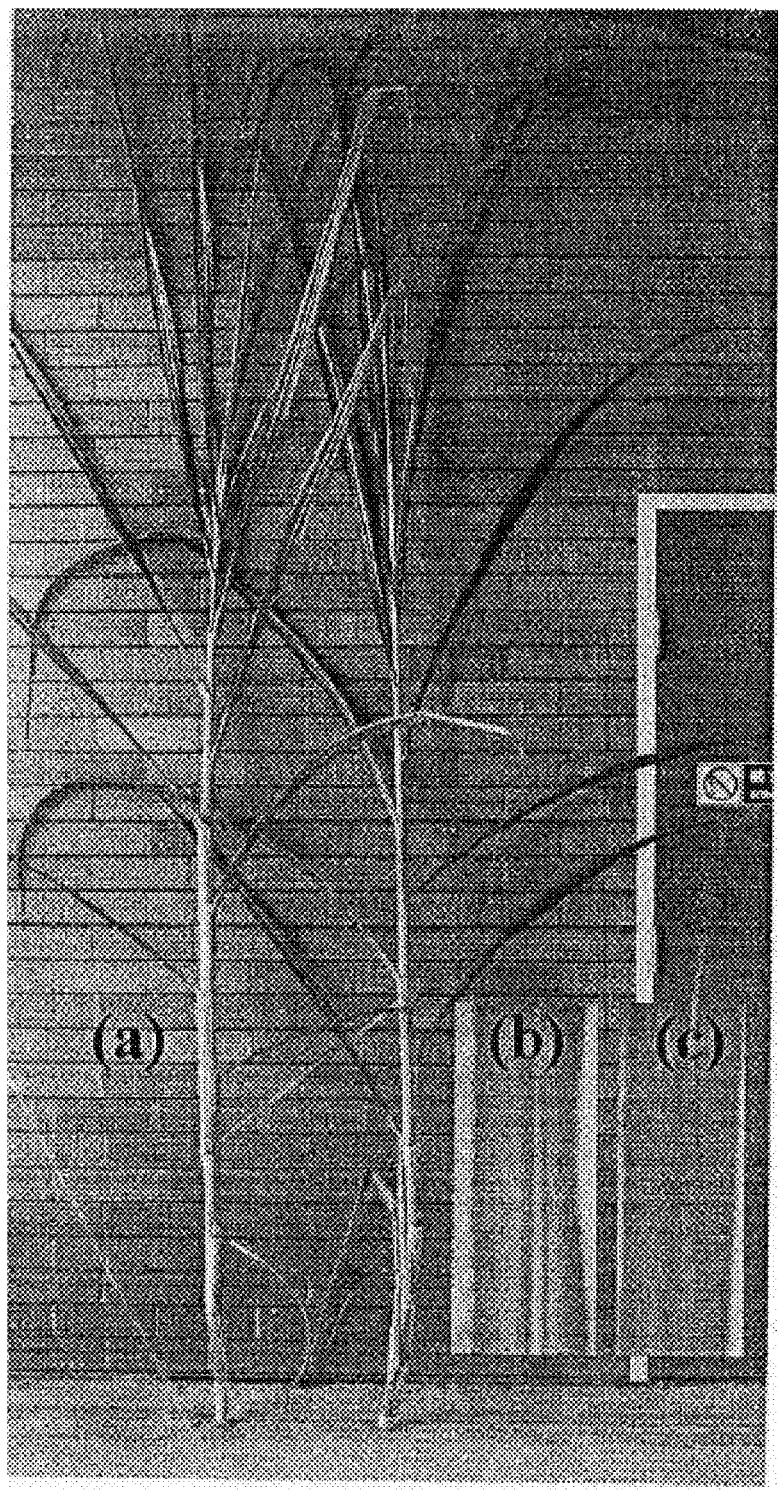
FIG. 16 is a photographic representation showing a comparison of the growth phenotype between the highest pHBA producer, UH98 and the control line TC1 reveals no obvious differences. (a) Plants of approximately equivalent age were compared. TC1, (left), UH98, (right). Inset: A close-up view of the under surface of a leaf is shown for TC1 (b) and UH98 (c).

Based on the results obtained with the 4-week-old plants, a subset of the primary transformants was selected for further evaluation, and leaf levels of pHBA were determined after 16 weeks additional growth (FIG. 15). Included in this analysis were the two CPL-expressing plants that previously exhibited the highest levels of product accumulation (UC63 and UC65) and five HCHL-expressing plants. The methanol-extracted samples were subjected to acid hydrolysis, which quantitatively hydrolyzes both pHBA glucose conjugates, and free pHBA was determined by HPLC.

It was anticipated that pHBA production would continue throughout development and that the 20-week-old plants would have higher levels of pHBA glucosides than the 4-week-old plants. However, the increase in pHBA content with age was not very dramatic nor was it universally observed when product accumulation was expressed on a dry weight basis. Part of the explanation for this is the lower water content of the older plant leaf tissue. For example, the average dry weight to wet weight ratio for the 20-week-old plants was 0.23, while the corresponding value for the 4-week-old plants was 0.15. When this phenomenon is taken into account and product accumulation is expressed on a fresh weight basis it becomes far more apparent that pHBA levels did increase as the plants continued to grow, except for the two CPL-expressing plants.

The 20-week-old primary transformants were large enough to screen for stalk levels of pHBA without damaging the plants. At this stage of development, the oldest stem tissue is semi-mature and new tillers emerge. Since the stalk is the only part of the sugarcane plant that is normally harvested in the existing sugar mill infrastructure, pHBA accumulation in this tissue is the most important gauge for technical success. Leaf and stem samples were taken from 20-week-old plants, and total pHBA was determined by HPLC after methanol extraction and acid hydrolysis. The third internode from the bottom of the plant was the source of stem tissue for this analysis, and the leaf samples were obtained from the third fully unfurled leaf from the top of the plant. Generally speaking, leaf levels of pHBA were considerably higher than stalk levels.

However, the difference was much more pronounced for the CPL-expressing plants. For example, the average stalk to leaf ratio of pHBA for the five UH lines that were examined was 0.324±0.031, and the highest stalk level of pHBA was 0.24% DW, which is equivalent to 0.52% pHBA glucose conjugates. In marked contrast, the corresponding ratios for UC63 and UC65 were 0.135 and 0.133, respectively, and product accumulation in the stalk of the best plant (UC63) was only 0.06% DW. Since there are no reported values in the literature for pHBA levels in stem tissue for transgenic plants expressing CPL or HCHL, it will be very interesting to see if these observations will extend to other plant systems. Nevertheless, taken together the above results suggest that HCHL is a better catalyst for pHBA production in sugarcane than CPL, and subsequent studies focused on the UH series of plants.

EXAMPLE 22

Localization of pHBA in Sugarcane Tissue

To gain a better understanding of pHBA accumulation in different parts the plant, leaf and stem segments were sampled from the primary shoot of 20-week-old UH1. The first leaf at the top with a fully visible dewlap was designated "leaf 1" and consecutive leaves down the stalk were numbered in ascending order. The stem segments were numbered similarly with "internode 1" corresponding to the internode immediately above the point of attachment of leaf 1. The results from this analysis are summarized in FIG. 15. Note that the values shown refer to total pHBA after acid hydrolysis. Except for the youngest leaf examined, product accumulation in leaves was relatively uniform along the length of the plant achieving a maximum value of ~1.0% DW. Product accumulation also varied along the length of the leaf, with the tip of the leaf having about twice as much pHBA as the base of leaf (data not shown). A similar trend was observed in the stalk, but there was a much larger discrepancy between young stem tissue and old stem tissue. In agreement with the results described above, pHBA levels in mature stem tissue were about 3-fold lower than mature leaf tissue. These results add additional support to the notion that pHBA accumulation in HCHL-expressing sugarcane plants increases as a function of time.

Additional insight on pHBA distribution was obtained from dissection experiments similar to the one shown in FIG. 15. The plant that was used for this analysis was 20-week-old UH1. Three different compartments of the stalk were examined: rind, pith, and vascular bundles. The most pHBA was found in the rind (1% DW), while the pith and vascular bundles had 3- to 4-fold lower levels. Indeed, pHBA levels in the rind were very similar to values obtained from the leaf midrib and leaf lamina.

Of all of the HCHL-expressing primary transformants monitored, UH98 (FIG. 2B) consistently had the highest levels of pHBA in both leaf and stem tissue. When this plant was 20 weeks old pHBA accumulation in leaf tissue was 2.8% DW (leaf lamina, 3.35% DW; leaf midrib, 1.61% DW). The corresponding value for mature stem tissue was 0.67% DW (rind, 0.96% DW; pith, 0.65% DW). Despite these very high levels of pHBA glucose conjugates, UH98 was morphologically indistinguishable from the non-transformed control line TC1 (FIG. 5).

EXAMPLE 23

Construction of cTP-CPL

PCR was used to generate the monocot chloroplast-targeting sequence that was fused to the N-terminus of *E. coli* CPL. The target for amplification was the maizerbcS gene (GenBank accession number Y00322), which codes for the Rubisco small subunit precursor. Primer 1 (5'-CTA CTC ATA ACC ATG GCG CCC ACC GTG-3') (SEQ ID NO:54) hybridized to nucleotides 489-505 and introduced aNcoI site at the start codon of the transit peptide.

Primer 2 (5'-CAT CTT ACT CAT ATG CCG CAC CTG CAT GCA CCG GAT CCT TCC G-3') (SEQ ID NO:55)hybridized to nucleotides 616-639 and introduced anNdeI site five amino acid residues downstream from the chloroplast cleavage site. The PCR product was cut with NcoI and NdeI and inserted into pET24a-tTP-CPL (manuscript in preparation), after the latter was cleaved with the same enzymes. pET24a-tTP-CPL contains the gene for a chimeric protein that consists of the tomato Rubisco small subunit transit peptide plus the first four amino acid residues of the 'mature' Rubisco small subunit, fused to the N-terminus of *E. coli* CPL. The plasmid DNA was cut with NcoI and NdeI to remove the tomato chloroplast-targeting sequence, and this was replaced with PCR-generated maize chloroplast-targeting sequence. The ligation mixture was introduced into *E. coli* DH10B, and growth was selected on LB media containing kanamycin (50g mL−1). A representative plasmid (pET24a-cTP-CPL) was sequenced and no PCR errors were found. The predicted chloroplast cleavage product of the cTP-CPL fusion protein is a CPL variant with five extra N-terminal amino acid residues (i.e. MQVRH-CPL) (SEQ ID NO:56).

EXAMPLE 24

Generation of CPL and HCHL Expression Constructs Used for Sugarcane Transformation The antibiotic selection plasmid pUKN contains the ubi-1 promoter, the neomycin phosphotransferase gene and the nos terminator. The plasmid pU3z-mcs-nos was used for cTP-CPL and HCHL expression in sugarcane. This plasmid is a modification of pAHC20 and contains the maize ubi-1 promoter and nos terminator. Both genes were inserted in the SpeI and KpnI sites of the multicloning region that immediately follows the maize ubi-1 intron. The gene coding for cTP-CPL was amplified from pET24a-cTP-CPL using primers 3 and 4. Primer 3 (5'-CTA CTC ATT TAC TAG TCA CCA TGG CGC CCA CCG TGA TG-3') (SEQ ID NO: 50) hybridized to the first 18 nucleotides of the ORF of cTP-CPL and introduced a SpeI site upstream from the start codon. Primer 3 also contained a consensus monocot ribosomal binding site, CACC, which is situated between the SpeI site and the initiator Met codon. Primer 4 (5'-CAT CTT ACT GGT ACC TTT AGT ACA ACG GTG ACG CC-3') (SEQ ID NO: 51) hybridized to the other end of the insert and introduced a KpnI site just after the cTP-CPL stop codon. The PCR product was cut with SpeI and KpnI, and ligated into similarly digested pU3z-mcs-nos. The ligation reaction mixture was used to transform *E. coli* DH10B and growth was selected on LB media containing ampicillin (100 μg mL−1). A representative plasmid (pU3z-mcs-nos-cTP-CPL) was sequenced to confirm the absence of PCR errors.

Primers 5 and 6 were used to amplify the *Pseudomenas fluorescens* strain AN103 HCHL gene (GenBank accession number Y13067) from plasmid pFI039. Primer 5 (5'-CTA CTC ATT TAC TAG TCA CCA TGA GCA CAT ACG AAG GTC G-3') (SEQ ID NO: 52) hybridized to the first 20 nucleotides of the ORF for HCHL and introduced a unique SpeI site upstream from the start codon. Primer 5 also contained a consensus monocot ribosomal binding site (CACC) that is situated between the SpeI site and the initiator Met codon. Primer 6 (5'-CAT CTT ACT GGT ACC TTC AGC GTT TAT ACG CTT GCA-3') (SEQ ID NO: 53) hybridized to the other end of the insert and introduced a KpnI site just after the HCHL stop codon. The PCR product was cut with SpeI and KpnI, and ligated into similarly digested pU3z-mcs-nos. The ligation reaction mixture was used to transform *E. coli* DH10B and growth was selected on LB media containing ampicllin (100 μg mL−1). A representative plasmid (pU3z-mcs-nos-HCHL) was sequenced to confirm the absence of PCR errors.

EXAMPLE 25

Plant Transformation

Embryogenic callus from sugarcane cultivar Q117 was prepared essentially as described, and grown in the dark at 27° C. on MS media supplemented with 3 mg L−1; of 2,4-dichlorophenoxy acetic acid (2,4-D). The calli were co-transformed with the antibiotic selection plasmid pUKN by microprojectile bombardment. Following bombardment and a recovery phase of 2 weeks in the dark, transformants were placed on MS-2,4D selection media supplemented with 60 mg L−1 geneticin. Individual callus clumps were maintained separately throughout the selection process. After 6 weeks, antibiotic-resistant calli were transferred to MS media supplemented with geneticin and incubated in the light to initiate plantlet regeneration. At least four plantlets per callus clump were transferred to pots in a glasshouse certified for the physical containment of transgenic plants for further analysis.

EXAMPLE 26

Measurement of Accumulated Soluble Phenolics by HPLC

Soluble phenolics were extracted from 100-200 mg of leaf or stem tissue. The tissue samples was resuspended in 1 mL of 50% v/v methanol and homogenized in a bead beater (Bio101/Savant, Fastprep FP120, Holbrook, N.Y.). The sample were then agitated in an orbital shaker (200 rpm) for 1 hour at 37° C., and clarified by centrifugation. A 550-μL aliquot of extract was transferred to a fresh tube and dried under vacuum, and the dry residue was dissolved in. 200 μL.

When the goal was to convert pHBA and vanillic acid glucose conjugates to free pHBA and vanillic acid an acid hydrolysis step was included. A 200-μL aliquot of the extract was transferred to a fresh tube and dried under vacuum. After adding 200 µL of 1 N HCl to the dry residue and vortexing, the sample was incubated for 2 hours at 95° C. The sample was then neutralized by adding 200 µL of 1.2 N NaOH.

Soluble phenolics were detected by HPLC at 32° C. using the Novapak C18 column described above. Samples were filtered through 0.2 µm syringe filters and 20 µL of filtrate was injected for each analysis. Mobile phases were the same as previously described. Solvent was pumped at 1 mL min$^{-1}$ using the following gradient conditions: 0 min, 0% B; 80 min, 80% B; 81 min, 100% B; 85 min, 100% B; 86 min, 0% B. Total run time was 90 minutes. An optimized gradient was applied to separate p-hydroxybenzoic acid and vanillic acid (0 min, 10% B; 20 min, 50% B; 21 min, 100% B; 24 min, 100% B; 25 min, 10% B; total runtime was 35 minutes). Identified peaks were quantified using authentic standards (Sigma-Aldrich Co.).

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of said steps or features.

BIBLIOGRAPHY

Altschul et al., *Nucl. Acids Res.* 25: 3389-3402. 1997;
An, *Methods of Enzymology* 153: 292, 1987;
Ausubel et al., "Current Protocols in Molecular Biology" John Wiley & Sons Inc, 1994-1998, Chapter 15.
Barker et al., *Plant Mol. Biol.* 2: 235-350, 1983;
Bevan et al., *Nucl. Acid Res.* 11: 369, 1983;
Biebl et al., *Appl. Microbiol Biotechnol.* 52: 289-297, 1999;
Bohmert et al., *Planta* 211: 841-845, 2000;
Bower et al., *Molec. Breeding* 2: 239-249, 1996;
Braunegg et al., *Eur. J. Appl. Microbiol. Biotechnol.* 6: 29-37, 1978;
Cahoon and Ohlrogge, *Plant physiol.* 104: 827-837, 1994;
Cahoon et al., *Proc. Natl. Acad. Sci. USA* 89: 11184-11188, 1992
Chaumont et al., *PMB* 24: 631-664, 1994;
De Koning, *Can. J. Micro.* 41(1: 303-309, 1995;
Dellaporta et al., in *Chromosome Structure and Function* pp. 263-282, 1988;
Ehrlich, *Proc. Natl. Acad. Sci. USA* 75: 1433, 1978;
Etschmann et al., *Appl. Microbiol. Biotechnol.* 59: 1-8, 2002;
Fang and Hirsch, *Plant Physiol.* 115:53-68, 1998;
Garfinkel et al., *Cell* 27: 143-153, 1983;
Gemgross, *Nature Biotech.* 17: 541-544, 1999;
Greenspan et al., *J. Cell Biol.*, 100: 965-73, 1985;
Greve, *J. Mol. Appl. Genet.* 1: 499-511, 1983;
Ikuta et al., *Biotech* 8: 241, 1990;
Jendrossek et al., *App. Micro. Biotech.* 46: 451-463, 1996;
Karr et al., *Applied and Environmental Microbioilogy* 46: 1339-1344, 1983;
Katz et al, *J. Gen. Microbiol.* 129: 2703, 1983;
Kim et al., *Plant Cell Physiol.* 44(4): 412-414;
Knight et al., *Plant Cell* 11(5): 875-886, 1999;
Lee, *Trends Biotech.* 14: 431-438, 1996;
Mayer et al., *Plant Cell* 13:1669-1682, 2001;
Mekhedov et al., *Plant Mol. Biol.* 47: 507-518, 2001;
Mergaert and Swings, *Indust. Micro. Biotech.* 17: 463-469, 1996;
Niedz et al., *Plant Cell Reports* 14: 403, 1995;
Niu et al., *Biotechnol. Prog.* 18: 201-211, 2002;
Ostle et al., *Appl. Environ. Microbiol.* 44: 238-41, 1982;
Ow et al., *Science* 234: 856, 1986;
Poirier et al., *Science* 256: 520-523, 1992;
Potrykus et al., *Mol. Gene. Genet.* 199: 183, 1985;
Prasad et al., *Appl. Environ. Microbiol.* 69(2): 917-925, 2003;
Prasher et al., *Biochem. Biophys. Res. Comm.* 126: 1259, 1985;
Salomon et al., *EMBO. J.* 3: 141-146, 1984;
Sambrook et al., Molecular Cloning, A Laboratory Manual, 2$^{nd}$ Edition, Cold Spring Harbor Press, 1989
Siebert et al., *Plant Physiol.* 112: 811-819, 1996,
Slater et al., *J. Bacteriol.* 180: 667-673, 1998;
Steinbüchel and Schlegel, *Mol. Micro.* 5: 535-542, 1991;
Sticher et al., *Annu. Rev. Phytopathol.* 35: 235-270, 1997;
Sutcliffe, *Proc. Natl. Acad. Sci. USA* 75: 3737, 1978;
Taguchi et al., *FEMS Microbiol. Lett.* 198: 65-71, 2001;
Thillet et al., *J. Biol. Chem.* 263: 12500, 1988;
Veerpoorte and Memelink, *Curr. Opin. Biotech.* 13: 181-187;
Zukowsky et al., *Proc. Natl. Acad. Sci. USA* 80: 1101, 1983;

---

We claim:

1. A method for producing polyhydroxyalkanoates (PHAs) in a species of *Saccharum*, said method comprising expressing nucleotide sequences comprising SEQ ID NO:1, SEQ ID NO:4 and SEQ ID NO:7 or nucleotide sequences capable of hybridizing to the complement of SEQ ID NO:1, SEQ ID NO:4 or SEQ ID NO:7 under stringent conditions, wherein the *Saccharum* accumulates PHA at about 1.6% of leaf dry-weight, and wherein PHA accumulation does not reduce total sugar content in PHA producing plants as compared to control plants.

2. The method of claim 1 wherein the species of the *Saccharum* genus is sugarcane.

3. The method of claim 1 wherein the polyhydroxyalkanoate is polyhydroxybutryate.

4. The method of claim 1 wherein the nucleotide sequences further comprises SEQ ID NO:19 or a nucleotide sequence capable of hybridizing to the complement of SEQ ID NO:19 under stringent conditions.

5. A genetically modified *Saccharum* sp. cell comprising a genetic sequence comprising SEQ ID NO:1, SEQ ID NO:4 and SEQ ID NO: 7 or nucleotide sequences capable of hybridizing to the complement of SEQ ID NO:1, SEQ ID NO:4 or SEQ ID NO:7 under stringent conditions, wherein a *Saccharum* plant comprising said cell accumulates PHA at about 1.6% of leaf dry-weight, and wherein PHA accumulation does not reduce total sugar content in PHA producing plants as compared to control plants.

6. The *Saccharum* sp. cell of claim 5, wherein said *Saccharum* sp. is sugarcane.

7. The *Saccharum* sp. cell of claim 5, wherein the polyhydroxyalkanoate is polyhydroxybutyrate.

8. A genetically modified *Saccharum* sp. plant comprising one or more cells of claim 5.

9. Genetically modified seeds or other reproductive material, or genetically modified propagation material from the plant of claim 8.

10. A plant based bioreactor system used for the production of a polyhydroxyalkanoate, said bioreactor comprising one or more genetically modified cells of claim 5.

11. A plant based bioreactor system used for the production of a polyhydroxyalkanoate, said bioreactor comprising one or more genetically modified cells of claim 8.

12. The method of claim 1 wherein the nucleotide sequences further comprises SEQ ID NO:28 or a nucleotide sequence capable of hybridizing to the complement of SEQ ID NO:28 under stringent conditions.

13. The method of claim 1 wherein the nucleotide sequences further comprises SEQ ID NO:31 or a nucleotide sequence capable of hybridizing to the complement of SEQ ID NO:31 under stringent conditions.

14. The genetically modified *Saccharum* sp cell of claim 5 which further comprises SEQ ID NO:19 or a nucleotide sequence capable of hybridizing to the complement of SEQ ID NO:19 under stringent conditions.

15. The genetically modified *Saccharum* sp cell of claim 5 which further comprises SEQ ID NO:28 or a nucleotide sequence capable of hybridizing to the complement of SEQ ID NO:28 under stringent conditions.

16. The genetically modified *Saccharum* sp cell of claim 5 which further comprises SEQ ID NO:31 or a nucleotide sequence capable of hybridizing to the complement of SEQ ID NO:31 under stringent conditions.

17. A method for producing polyhydroxyalkanoates (PHAs) in a species of *Saccharum*, said method comprising expressing nucleotide sequences comprising SEQ ID NO:1, SEQ ID NO:4 and SEQ ID NO:7 or nucleotide sequences capable of hybridizing to the complement of SEQ ID NO:1, SEQ ID NO:4 or SEQ ID NO:7 under stringent conditions, wherein at least one of the nucleotide sequences is operably linked to a maize polyubiquitin (Ubi) promoter.

18. A genetically modified *Saccharum* sp. cell comprising a genetic sequence comprising SEQ ID NO:1, SEQ ID NO:4 and SEQ ID NO: 7 or nucleotide sequences capable of hybridizing to the complement of SEQ ID NO: 1, SEQ ID NO:4 or SEQ ID NO:7 under stringent conditions, wherein at least one of the nucleotide sequences is operably linked to a maize polyubiquitin (Ubi) promoter.

* * * * *